(12) United States Patent
Chiu et al.

(10) Patent No.: US 10,421,070 B2
(45) Date of Patent: Sep. 24, 2019

(54) METHOD AND APPARATUS FOR THE DISCRETIZATION AND MANIPULATION OF SAMPLE VOLUMES

(71) Applicant: University of Washington, Seattle, WA (US)

(72) Inventors: Daniel T. Chiu, Seattle, WA (US); Dawn E. Cohen, Seattle, WA (US); Gavin D. M. Jeffries, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 14/869,871

(22) Filed: Sep. 29, 2015

(65) Prior Publication Data

US 2016/0096172 A1    Apr. 7, 2016

Related U.S. Application Data

(62) Division of application No. 12/510,110, filed on Jul. 27, 2009, now Pat. No. 9,180,453.

(Continued)

(51) Int. Cl.
*B01L 3/00* (2006.01)
*B01L 7/00* (2006.01)
(Continued)

(52) U.S. Cl.
CPC ......... *B01L 3/502* (2013.01); *B01L 3/502784* (2013.01); *B01L 7/52* (2013.01);
(Continued)

(58) Field of Classification Search
CPC ..... B01L 2200/0642; B01L 2200/0673; G01N 2035/1032; G01N 2035/1034; G01N 35/08
See application file for complete search history.

(56) References Cited

U.S. PATENT DOCUMENTS 4,857,453 A    8/1989    Ullman et al.
5,061,381 A    10/1991   Burd
(Continued)

FOREIGN PATENT DOCUMENTS

CN        102187216 A     9/2011
KR   10-2002-0096070 A   12/2002
(Continued)

OTHER PUBLICATIONS

Adamo, et al. Microfluidic based single cell microinjection. Lab Chip, Jul. 1, 2008, 8: 1258-1261.
(Continued)

*Primary Examiner* — Betty J Forman
(74) *Attorney, Agent, or Firm* — Christensen O'Connor Johnson Kindness PLLC

(57) ABSTRACT

Embodiments of the present invention relate to methods and apparatuses for the discretization and manipulation of sample volumes that is simple, robust, and versatile. It is a fluidic device that partitions a sample by exploiting the interplay between fluidic forces, interfacial tension, channel geometry, and the final stability of the formed droplet and/or discretized volume. These compartmentalized volumes allow for isolation of samples and partitioning into a localized array that can subsequently be manipulated and analyzed. The isolation of the discretized volumes along with the device's inherent portability render our invention versatile for use in many areas, including but not limited to PCR, digital PCR, biological assays for diagnostics and prognostics, cancer diagnosis and prognosis, high throughput screening, single molecule and single cell reactions or assays, the study crystallization and other statistical processes, protein crystallization, drug screening, environmental testing, and the coupling to a wide range of analytical detection techniques for biomedical assays and measure-
(Continued)

ments. The minimal fluid interconnects and simple flow geometry makes the device easy to use and implement, economical to fabricate and operate, and robust in its operations.

37 Claims, 78 Drawing Sheets

Related U.S. Application Data

(60) Provisional application No. 61/089,367, filed on Aug. 15, 2008.

(51) Int. Cl.
  *G01N 35/08* (2006.01)
  *G01N 35/10* (2006.01)
  G01N 35/00 (2006.01)

(52) U.S. Cl.
  CPC .............. *G01N 35/08* (2013.01); *G01N 35/10* (2013.01); *B01L 2200/0642* (2013.01); *B01L 2200/0673* (2013.01); *B01L 2300/0877* (2013.01); *B01L 2300/0883* (2013.01); *B01L 2300/165* (2013.01); *B01L 2300/1827* (2013.01); *B01L 2300/1861* (2013.01); *B01L 2400/0439* (2013.01); *B01L 2400/0633* (2013.01); *G01N 2035/00356* (2013.01); *G01N 2035/1032* (2013.01); *G01N 2035/1034* (2013.01)

(56) References Cited

U.S. PATENT DOCUMENTS

| 6,124,138 | A * | 9/2000 | Woudenberg | B01L 3/5027 435/287.2 |
|---|---|---|---|---|
| 6,499,499 | B2 | 12/2002 | Dantsker et al. | |
| 6,706,519 | B1 | 3/2004 | Kellogg et al. | |
| 7,338,760 | B2 | 3/2008 | Gong et al. | |
| 7,390,676 | B2 | 6/2008 | Seul et al. | |
| 8,062,903 | B2 | 11/2011 | Chin et al. | |
| 8,277,759 | B2 | 10/2012 | Sundberg et al. | |
| 8,926,811 | B2 | 1/2015 | Wu | |
| 8,940,147 | B1 | 1/2015 | Bartsch et al. | |
| 9,180,453 | B2 | 11/2015 | Chin et al. | |
| 2002/0187072 | A1 | 12/2002 | Karp | |
| 2003/0138941 | A1 | 7/2003 | Gong et al. | |
| 2003/0138973 | A1 | 7/2003 | Wagner et al. | |
| 2003/0152994 | A1 | 8/2003 | Woudenberg et al. | |
| 2004/0018116 | A1 | 1/2004 | Desmond et al. | |
| 2004/0163958 | A1 | 8/2004 | Kao et al. | |
| 2004/0219590 | A1 | 11/2004 | Dickinson et al. | |
| 2004/0241693 | A1 | 12/2004 | Ricoul et al. | |
| 2007/0003443 | A1 | 1/2007 | Sandell et al. | |
| 2007/0052781 | A1* | 3/2007 | Fraden | B01L 3/502784 347/96 |
| 2007/0092924 | A1 | 4/2007 | Anderson | |
| 2008/0014589 | A1 | 1/2008 | Link et al. | |
| 2009/0071833 | A1 | 3/2009 | Gorfinkel et al. | |
| 2009/0217742 | A1 | 3/2009 | Chiu et al. | |
| 2010/0015715 | A1 | 1/2010 | Cho et al. | |
| 2010/0041046 | A1 | 2/2010 | Chin et al. | |
| 2011/0053151 | A1 | 3/2011 | Hansen et al. | |
| 2013/0065280 | A1 | 3/2013 | Park et al. | |
| 2013/0309780 | A1 | 11/2013 | Meltzer et al. | |
| 2014/0087386 | A1 | 3/2014 | Chiu et al. | |
| 2014/0138312 | A1 | 5/2014 | Bunner et al. | |
| 2014/0272981 | A1 | 9/2014 | Yamana et al. | |
| 2014/0360877 | A1 | 12/2014 | Ramsey et al. | |
| 2016/0354777 | A1 | 12/2016 | Chiu et al. | |
| 2018/0364270 | A1 | 12/2018 | Chiu et al. | |

FOREIGN PATENT DOCUMENTS

| WO | WO-2007013562 A1 | 2/2007 |
|---|---|---|
| WO | WO-2007116909 A1 | 10/2007 |
| WO | WO 2008/083526 A1 | 7/2008 |
| WO | WO-2010019388 A2 | 2/2010 |
| WO | WO-2010019388 A3 | 5/2010 |
| WO | WO-2012033765 A1 | 3/2012 |
| WO | WO-2014210207 A1 | 12/2014 |
| WO | WO-2017007954 | 1/2017 |

OTHER PUBLICATIONS

Biebuyck, et al. Self-Organization of Organic Liquids on Patterned Self-Assembled Monolayers of Alkanethiolates on Gold. Langmuir, 1994, 10: 2790-2793.
European search report and opinion dated Mar. 13, 2014 for EP Application No. 09807058.4.
International search report and written opinion dated Mar. 11, 2010 for PCT/US2009/052299.
Jackman, et al. Fabricating Large Arrays of Microwells with Arbitrary Dimensions and Filling Them Using Discontinuous Dewetting. Anal. Chem., 1998, 70(11): 2280-2287.
Lorenz et al. "Microfluidic and Optical Systems for the On-Demand Generation and Manipulation of Single Femtoliter-Volume Aqueous Droplets," Anal. Chern. 2006, vol. 78, No. 18, pp. 6433-6439.
Morrison, et al. Nanoliter high through quantitative PCR. Nucleic Acids Research, 2006, 34(18), e123, pp. 1-9.
Ottesen, et al. Microfluidic digital PCR enables multigene analysis of individual environmental bacteria. Science. Dec. 1, 2006;314(5804):1464-7.
Pollack, et al. Electrowetting-based actuation of liquid droplets for microfluidic applications. Appl. Phys. Lett., 2000, 77:1725.
Sgro et al. "Thermoelectric Manipulation of Aqueous Droplets in Microfluidic Devices," Anal. Chem. 2007, vol. 79, No. 13, pp. 4848-4851.
Shi, et al. Droplet-based microfluidic system for individual Caenorhabditis elegans assay. Lab Chip, 2008, 8: 1432-1435.
Unger et al. "Monolithic microfabricated valves and pumps by multilayer soft lithography," Science, 2000, vol. 288, pp. 113-116.
Extended European search report and opinion dated Jan. 2, 2017 for EP Application No. 14817344.
International search report and written opinion dated Sep. 23, 2016 for PCT Application No. US-2016041369.
International search report and written opinion dated Oct. 20, 2014 for PCT/US2014/044167.
Rossi, et al., Tapered Microfluidic Chip for the Study of Biochemical and Mechanical Response at Subcellular Level of Endothelial Cells to Shear Flow, Lab on A Chip, 2009, 9(10):1403-11.
Wu, et al., Fabrication of microchannels using polynorbomene photosensitive sacrificial materials, J. of the electrochemical society, 2003,150(9):H205-H213.
Office action dated Sep. 14, 2017 for U.S. Appl. No. 14/900,926.
Office Action dated Nov. 6, 2017 for CN Patent Application No. 201480042392.6.
Co-pending U.S. Appl. No. 15/741,462, filed Jan. 2, 2018.
Hatch et al. 1-Million droplet array with wide-field fluorescence imaging for digital PCR, Lab on a Chip, 11(22):3838-3845 (2011).
U.S. Appl. No. 14/900,926 Office Action dated Jan. 9, 2018.
Shen et al. Digital PCR on a SlipChip. Lab Chip 10:2666-2672 (2010).
Song et al. A nanoliter self-priming compartmentalization chip for point-of-care digital PCR analysis, Biomedical Microdevices, 17:64, 8 pages (2015).
Tanaka et al. Hands-Off Prepration of Monodisperse Emulsion Droplets Using a Poly(dimethlsiloxane) Microfluidic Chip for Droplet Digital PCR, Anal. Chem. 87(8):4134-4143 (2015).
JP 2016-521913 Office Action dated May 1, 2018. (w/ English translation).

(56) References Cited

OTHER PUBLICATIONS

Chinese office action dated Aug. 1, 2018 for Chinese Application No. 201480042392.
European search report with written opinion dated Feb. 5, 2019 for EP Application No. 16821991.
Office action dated Nov. 2, 2018 for U.S. Appl. No. 14/900,926.

* cited by examiner a) Fill channel with immiscible phase b) Flow sample through channel c) Flow immiscible phase through channel b)

c)

a) Fill channel with sample b) Flow immiscible phase through channel a) Discretized samples formed with a fast immiscible phase flow rate.

b) Discretized samples formed with a slower immiscible phase flow rate.

a) Fill channel with immiscible phase b) Flow sample through channel c) Flow immiscible phase through channel a) Fill channel with immiscible phase b) Flow sample through channel c) Flow immiscible phase through channel d) Flow a more viscous immiscible phase through channel e) Remove samples from chambers

METHOD AND APPARATUS FOR THE DISCRETIZATION AND MANIPULATION OF SAMPLE VOLUMES

CROSS-REFERENCES TO RELATED APPLICATIONS

This application is a divisional of U.S. patent application Ser. No. 12/510,110, filed Jul. 27, 2009, which claims the benefit of U.S. Provisional Application No. 61/089,367, filed Aug. 15, 2008, of which are incorporated herein by reference in their entireties.

STATEMENT AS TO RIGHTS TO INVENTIONS MADE UNDER FEDERALLY SPONSORED RESEARCH OR DEVELOPMENT

This invention was made with U.S. government support under R01 EB005197 awarded by the National Institutes of Health. The U.S. Government has certain rights in the invention.

BACKGROUND OF THE INVENTION

A first step in many chemical and biological applications is the discretization of sample volumes into small individual volumes for subsequent assays and analysis, where the assay or analysis can be of the same type or different types. The diverse variety of these applications highlights a need for different sample generation techniques with distinct advantages. Towards this end, several methods exist. Traditional methods of generating small volumes of sample include the use of a nebulizer to create an aerosol and the mixing of a sample with an immisicible phase to create an emulsion. However, these methods have limiting properties. The droplets formed by a nebulizer exhibit a large range of sizes. Similarly, mixing two immisicible phases to form an emulsion does not produce monodisperse droplets. Furthermore, the droplets formed by either method are difficult to individually manipulate and analyze once formed. In addition, neither of these methods would be well suited for the continuous monitoring that is necessary for in situ assays.

A common approach to forming a discretized sample is the dispensing of small volumes into small wells or microwells. While this is a successful method of creating an array of spatially localized samples, the individual well filling can be a tedious endeavor. Furthermore, human error can get in the way of dispensing homogeneous volumes. To avoid this, researchers have developed special dispensing equipment, such as robotic pipettes. However, the need for specialized dispensing equipment limits the flexibility of these microwell platforms, as well as raising the cost. In addition, it is difficult to work with very small volumes (below 0.5 μL) because of the relatively high dispensing volumes of pipettes as well as problems with sample evaporation. (Jackman, R. J., Duffy, D. C., Ostuni, E., Willmore, N. D., and Whitesides, G. M. *Anal. Chem.* 1998, 70, 11, 2280-2287, Morrison, T., Hurley, J., Garcia, J., Yoder, K., Katz, A., Roberts, D., et. al. *Nucleic Acids Research* 2006 34, 18, 15), incorporated by reference in its entirety herein for all purposes.

Two methods of sample array generation which do not rely on manual sample dispensing are the arrangement of droplets on patterned self assembled monolayers (SAMs) (Biebuyk, H. A., Whitesides, G. M. *Langmuir* 1994, 10, 2790.), and droplet manipulation using electrowetting (Pollack, M. G., Fair, R. B., Shenderov, R. B. *Appl. Phys. Lett.* 2000, 77, 1725), incorporated by reference in its entirety herein for all purposes. In both cases, the sample is discretized by the surface properties of a substrate, inducing a more uniform droplet volume. However, electrowetting mostly works for samples that are above the nanoliter scale and require sophisticated patterns of electrodes, greatly limiting its utility. Patterned SAMs can be used to generate smaller volumes, however the preparation of these surfaces can be labor intensive. In addition, surfaces must be coated in a layer of gold, and then derivatized in order to achieve the patterned surface. This has the potential to limit the forms of analysis possible, since the substrate is often opaque.

Recently new methods of sample volume discretization have emerged. These methods include the use of microfluidic valves to separate volumes from each other (Unger, M. A., Chou, H. P., Thorsen, T., Scherer, A., and Quake, S. R. *Science* 2000 288(5463):113-116) or the generation of a droplet stream (Sgro, A., Allen, P. B., Chiu, D. T. *Anal. Chem.* 2007, 79, 4845-4851.) or individual droplets (Lorenz, R. M., Edgar, J. S., Jeffries, G. D. M., Chiu, D. T. *Anal. Chem.* 2006, 78, 6433-6439.), incorporated by reference in its entirety herein for all purposes.

These methods, however, may suffer from certain drawbacks. For example, the use of valves and pumps require complex fluidic control and fabricated devices that tend to be expensive, especially if many discrete volumes (hundreds to thousands) are involved. The use of steady state methods to generate a stream of droplets makes the subsequent manipulation and immobilization of droplets difficult, but more importantly, because it is a steady state method, it often involves loss of sample volume, that is, there is some initial waste of the sample because a steady state flow stream must be established first prior to the regular formation of droplets. Additionally, such flow methods require accurate control of flow rates, which also increases the complexity and expense of the final device or instrument.

Accordingly, there is a need in the art for novel approaches for the manipulation of sample volumes.

BRIEF SUMMARY OF THE INVENTION

Embodiments of the present invention relate to new methods to discretize sample volume that is simple, robust, and versatile. In particular embodiments, a fluidic device partitions the sample not based on a steady state method such as the formation of droplet streams, but rather based on the interplay between fluidic forces, interfacial tension, channel geometry, and the final stability of the formed droplet and/or discretized volume. These compartmentalized volumes allow for isolation of samples and partitioning into a localized array that can subsequently be manipulated and analyzed. The minimal fluid interconnects and simple flow geometry makes the device easy to use and implement, economical to fabricate and operate, and robust in its operations.

The device versatility has basis in, but is not limited to, its ease of generation and tunability, controlled by the surface properties of the channels within the device, the channel geometries, the properties of the interface, and the properties of the continuous and discontinuous phases. The isolation of the discretized volumes along with its inherent portability further expand upon the versatility for use in many areas, including but not limited to PCR, digital PCR, genotyping, single-cell gene expression analysis, determining copy number variations, biological assays for diagnostics and prognostics, cancer diagnosis and prognosis, DNA methylation assays, high throughput screening, single molecule and single cell reactions or assays, the study crystallization and statistical processes, protein crystallization, drug screening, environmental testing, and the coupling to a wide range of analytical detection techniques for biomedical assays and measurements. The unique stability of the device allows for combinations of manipulation and detection methods to be used in parallel or in series, generating an avenue for complementary detection techniques to be incorporated.

To demonstrate this device we performed experiments on droplet filling regimes, sample volume studies, the sample and immiscible phase properties, the interface properties, device geometry, flow rates, substrate property effects, and post discretization manipulation and detection.

DESCRIPTION OF THE DRAWINGS

FIGS. 19(b) and (d) are magnified view of regions 1905 and 1925 respectively.

DETAILED DESCRIPTION OF THE INVENTION

Embodiments of the present invention relate to methods and apparatuses for the analysis of species that include, but are not limited to, chemicals, biochemicals, genetic materials, or biological cells, using fluidic lattices to form fluidic packets. Potential applications for embodiments of the invention include but are not limited to, polymerase chain reaction (PCR), nucleic acid sequence-based amplification (NASBA), crystallization of proteins and small molecules, and the analysis of rare cells present in biological fluids.

Figure 1:
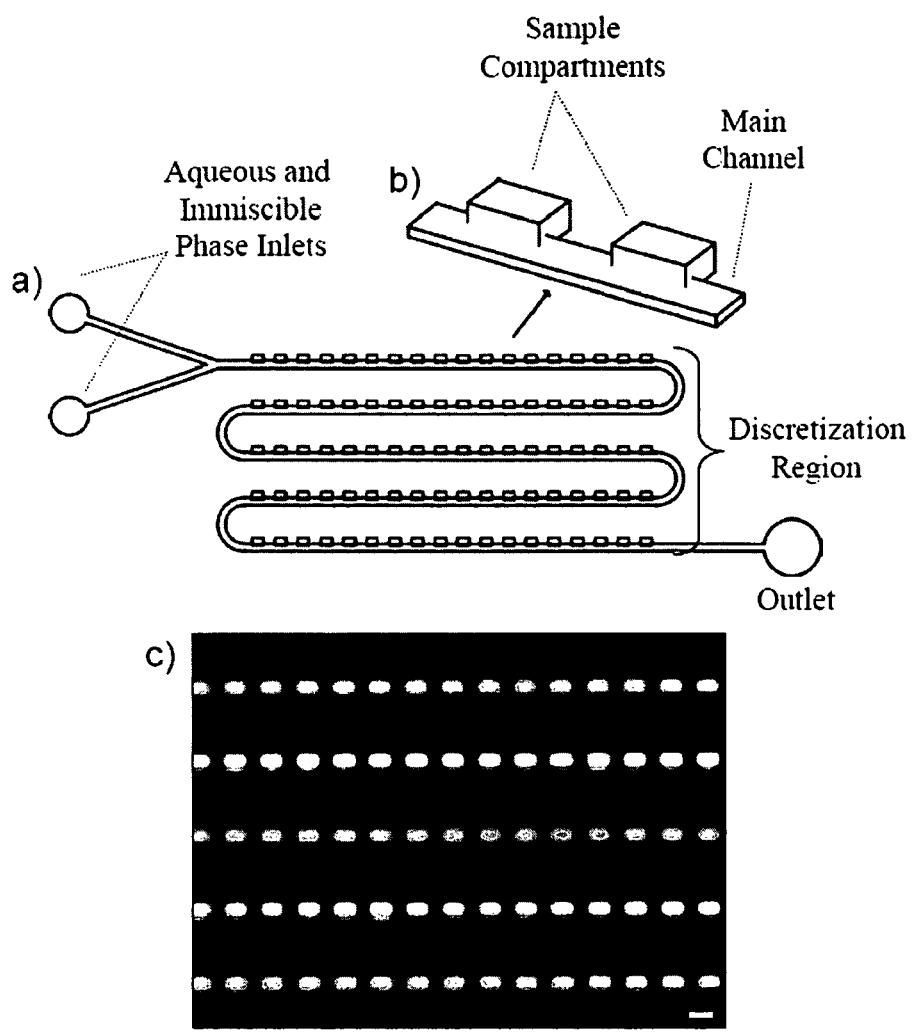
FIG. 1. a, b) Schematic of the discretization device and a pictorial definition of certain features. b) A magnified section of the discretization region depicting the sample compartments and the main channel. These features may or may not be of the same height. c) An image of the fluorescence emission from an array of sample volumes that have been discretized using our device. A 100 μM carboxyfluorescein solution was used as the sample phase. The immiscible phase is light mineral oil with 0.01% Span 80. The scale bar corresponds to 200 μm.

Described herein are devices for sample volume discretization and manipulation that can be tailored to suit a large variety of different applications and analysis methods. An overview of the device anatomy is shown in FIG. 1. In one embodiment, the device consists of a main channel studded with adjacent sample compartments (chambers) that are of a different height than the main channel. The dimensions of these two features may be varied to define the volume of the discretized sample. Once formed, the discretized volumes reside within the sample compartments. The spacing in a large array of samples is predefined by the spacing of the device sample compartments. In addition to this particular embodiment, many other designs and embodiments are also possible and will be described in more detail below.

The sample compartments or chambers that are in fluidic communication with a flow channel are hereafter also referred to as "fluidic harbors". Generally, these fluidic harbors are offset from an axis of flow through the flow channel.

A fluidic harbor is offset from an axis of flow through the flow channel, if the opening of the harbor is not oriented to accept direct impingement of the flow through the channel. In certain embodiments, flow may enter a fluid harbor at an angle not parallel to the axis of flow in the main flow channel. For example, in some embodiments, a flow may enter into an offset fluidic harbor in a direction perpendicular from an axis of flow through the flow channel. A fluidic harbor may also be said to be offset from an axis of flow through the flow channel if a line drawn between the center of harbor and the centerline of the flow channel is longer than the shortest distance between a channel wall and its centerline.

As employed herein, the term immiscible refers to fluids that do not form a homogeneous solution, or if an observable boundary separates the fluids. Such a boundary may be observable under a microscope, by optical scattering, or by detecting a preferential distribution of a molecule in one fluid over another fluid.

Embodiments of the present invention may include a method and an apparatus for conducting biochemical analysis, wherein:

(1) A first continuous fluid is flowed through a channel into a fluidic lattice, which is composed of fluidic harbors that shelter fluid against high velocity or a velocity gradient in the channel; and (2) A second continuous fluid is flowed through the fluidic lattice, unsettling the first fluid.

In certain embodiments, a third continuous fluid is flowed into the fluidic lattice following the second fluid, unsettling the second fluid.

In certain embodiments, the third fluid is chemically identical to the first fluid.

In certain embodiments, one or more fluids are flowed into the fluidic lattice following the first fluid, each fluid unsettling the previous fluid.

Certain embodiments of the present invention relate to methods or apparatuses for conducting biochemical analysis wherein a continuous fluid is transposed in order into fluidic packets residing in fluidic harbors, wherein the fluidic packets preserve a sequence of the continuous fluid.

As used herein, the term "transpose" herein refers to formulaic rearranging. In transposition, an identifiable sequence is preserved both prior and after transposition. For example, after transposition the identifiable sequence may be in the same order of the original sequence. In another example, after transposition the identifiable sequence may be in a reverse order of the original sequence. In another example, after transposition, the identifiable sequence may comprise only even number entries of the original sequence. In another example, after transposition, the identifiable sequence may comprise only odd number entries of the original sequence. In another example, after transposition, the identifiable sequence may comprise a block transposition of the original sequence, preserving packets of sequence.

In one embodiment, a sequence refers to a spatial composition distribution.

When a continuous fluid is analyzed for its composition, due to the free-flowing nature of the fluid, it may be difficult to preserve the spatial distribution of the composition profile while subjecting interrogation, heating, reaction or other manipulations intended to reveal the composition distribution. Embodiments of the invention take a continuous fluid, deconstructs it into fluidic packets residing in fluidic harbors, but in the deconstruction process also transposes the composition profile of the continuous fluid. For example, if the incoming continuous fluid includes five biological cells at the right of the fluid volume, ten cells at the middle of the fluid volume, and fifteen cells at the left of the fluid volume, the transposition process may generate a first fluidic packet residing in the leftmost fluidic harbor containing five cells, a second fluidic packet residing in the middle fluidic harbor containing ten cells, and a third fluidic packet residing in the rightmost fluidic harbor containing fifteen cells. Thus a sequence of cell numbers is preserved but in a reverse order following transposition.

An advantage offered by a transposition process is to preserve a sequence in some way while allowing manipulation. Deconstructing a continuous fluid into fluidic packets may sever the possibility of accidental mixing and hence potential destruction of spatial compositional information. Transposing allows for retention of the original sample sequence, enabling references to be traced back to the continuous fluid.

In an embodiment, each fluid that flows through a channel into a fluidic lattice may remain continuous until entering a first fluidic harbor. Droplets, bubbles, plugs, or segmented flow are dispersed discrete entities and are not considered as a continuous fluid.

In an embodiment, a continuous fluid comprises any undisrupted fluid with a volume that is equal to or greater than the volume of two fluidic harbors. In other embodiments, a continuous fluid comprises a fluid with volume that is equal or greater than the volume of 5 fluidic harbors. In yet another embodiment, a continuous fluid comprises a fluid with a volume that is equal or greater than the fluid of 20 fluidic harbors.

As used herein, "Biochemical analysis" refers to the determination of identity, concentration, proportion, reactivity, physical or molecular properties of an analyte present within a fluid. For example, a biochemical analysis can include PCR, Nucleic Acid Sequence-Based Amplification (NASBA), crystallization or precipitation of compounds, observation of single celled organisms, or identification of a cell, etc. "Biochemical analysis" can also refer to processes of interest such as reactions, crystal growth, and nanoparticle formation.

As used herein, "Analyte" refers to a species of interest that can include, but is not limited to, chemicals, biochemicals, small molecules, genetic materials, particles, or biological cells.

The term "Fluidic lattice" refers to a network of fluidic harbors interconnected by one or more channels. The arrangement of fluidic harbors may or may not be periodically repetitive on one or more sides of the connecting channel.

The term "Fluidic harbors" refer to locations along a channel that provide shelter from the flow in the channel so fluidic packets may be formed in the harbors. A fluidic packet accumulates in a harbor to substantially occupy the volume and assume substantially the shape of the harbor. For example, if a fluidic harbor is rectangular shaped, the fluidic packet contained within, should substantially assume a rectangular shape. In situations where the shape of a fluidic packet disagrees with the shape of an external enclosure, (for example, if a fluid assumes a spherical shape when an external enclosure is cubic shaped), such an enclosure is not considered as a fluidic harbor, because there exist wall forces that repel fluid away from the wall of the enclosure and fluid cannot be adequately sheltered from the velocity or velocity gradient of the flow channel.

A fluidic harbor shields a fluidic packet from the onslaught of high-velocity flow or high velocity-gradient flow. In certain embodiment, a fluidic harbor does not obstruct the flow in a flow channel it is in communication with. In certain embodiments, the flow direction at the entrance of a fluidic harbor is perpendicular to the flow direction of a flow channel it is in communication with.

In certain embodiments, "fluidic packet assuming substantially the shape of the harbor" refers to an increase in the surface area or perimeter of a fluidic volume that is 2% or greater compared its spherical state. In some embodiments "fluidic packet assuming substantially the shape of the harbor" refers to an increase in the surface area or perimeter of a fluidic volume that is 5% or greater compared its spherical state. In some embodiments, "fluidic packet assuming substantially the shape of the harbor" refers to an increase in the surface area or perimeter of a fluidic volume that is 10% or greater compared its spherical state. In yet another embodiment "fluidic packet assuming substantially the shape of the harbor" refers to an increase in the surface area or perimeter of a fluidic volume that is 25% or greater compared its spherical state.

"Main flow channel" refers to a channel which is used to sequentially connect individual fluidic harbors. The main flow channel provides fluidic communication with the fluidic harbors.

In certain embodiments, a fluidic harbor is marked by a protrusion away from the channel. A fluidic harbor connects to only one main channel, but may connect to a main channel more than once.

In certain embodiments, a fluidic harbor provides the coordinates for referencing a fluidic packet contained within the fluidic harbor or distinguishing one fluidic packet from another. For example, each fluidic harbor may be assigned a unique string of alphanumeric characters which identifies the fluidic packet contained within. In transposing a continuous fluidic specimen into a fluidic lattice, the specimen is deconstructed into physically distinct fluidic packets and each fluidic packet is uniquely identifiable according to the fluidic harbor it resides in.

The term "Fluidic packet" refers to a localized volume of fluid. A fluidic packet may be completely or substantially separated from the remainder volume of the same fluid. Separation may be accomplished with an intermediate solid (e.g. a wall), liquid (e.g. an immiscible liquid), gas, or vacuum. "Substantially separated" means that the diameter of fluid bridging between a packet and the remainder volume of the same fluid is no larger than 90% of the hydraulic diameter of the packet.

Figure 1A:
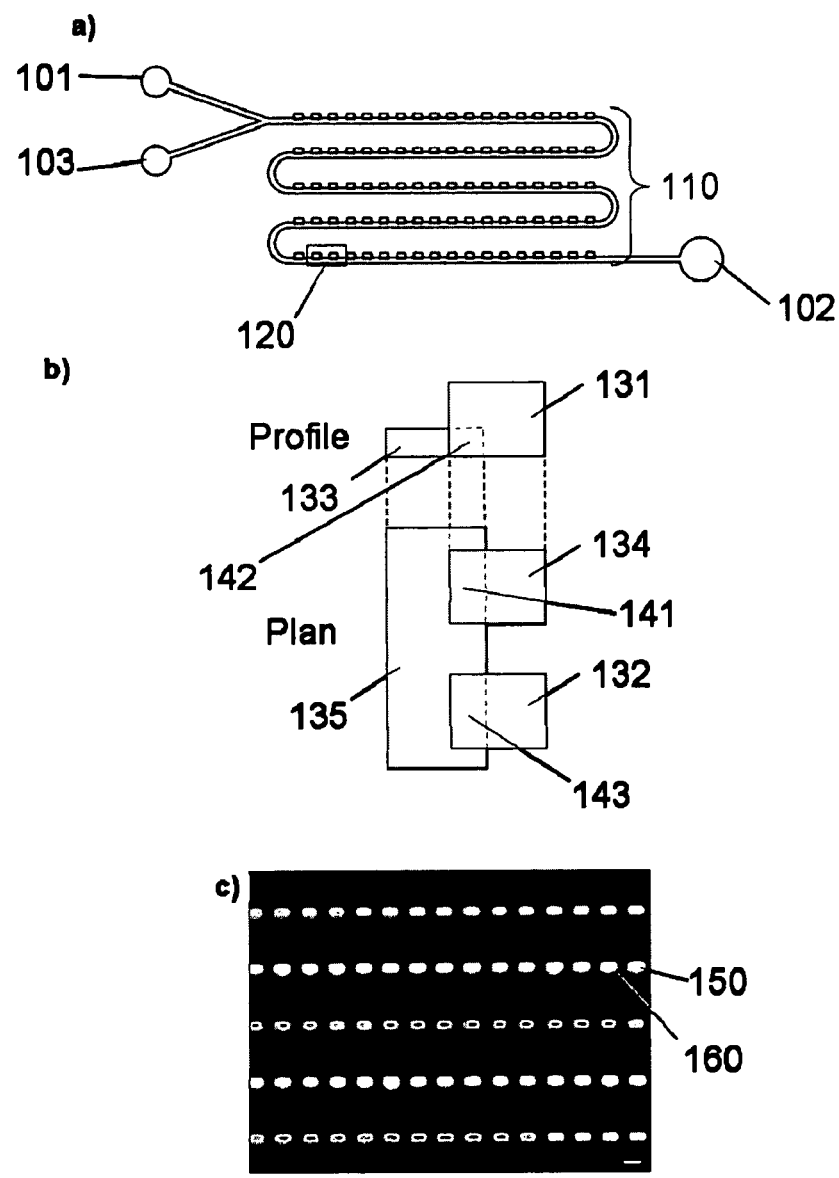
FIG. 1A. a, b) Schematics of a fluidic lattice and c) a fluorescent image of fluidic packets formed in fluidic harbors.

FIG. 1A illustrates schematics of a fluidic lattice. In FIG. 1A(a), continuous fluids were flowed into a fluidic lattice 110 with fluidic inlets 101 and 103, and a fluidic outlet 102. The fluidic lattice is composed of a flow channel with fluidic harbors 120 for generating fluidic packets. FIG. 1A(b) shows a profile view and a plan view of fluidic harbors. In profile view, fluidic harbor 131 is connected to fluidic channel 133, which may have a different height. In plane view, two fluidic harbors 134 and 132 were connected to a fluidic channel 135. FIG. 1A(c) shows a fluorescent image of fluidic packets 150 containing 150 µM carboxyfluorescein formed in fluidic harbors 160. Notice that a fluidic packet assumes substantially the shape of a fluidic harbor. The first and third fluid in this case was a light mineral oil with 0.01% Span 80. The scale bar corresponds to 200 µm.

Figure 11:
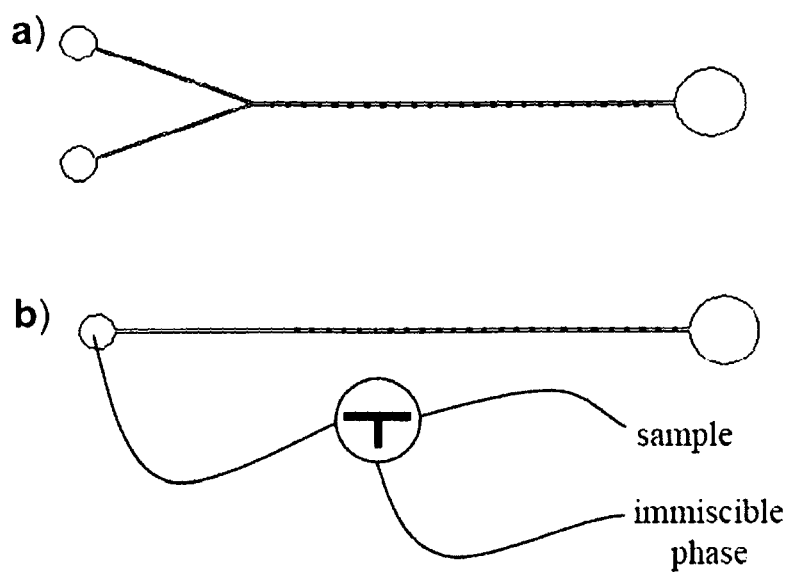
FIG. 11. Some examples of sample and immiscible phase inlet geometry. In a) two phases are introduced into the device directly. There is an inlet channel for each phase that is connected to the main channel, b) There is one inlet for the device that can be connected to a valve. The valve can be adjusted to choose the phase that is introduced to the chip. Different phases can be introduced into the device sequentially.
Figure 11A:
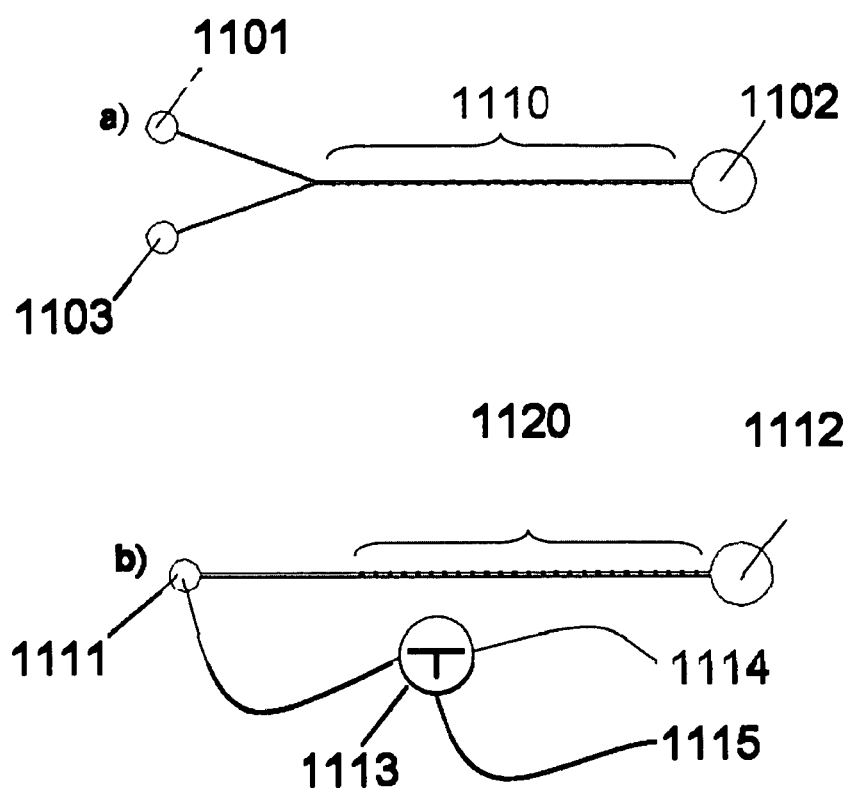
FIG. 11A. Examples of fluidic inlet configurations.

It is possible that a fluidic lattice may have a different number of fluidic inlets or outlets. For example, as illustrated in FIG. 11A, a fluidic lattice 1120 may have only a single inlet port 1111, but connected to fluidic sources 1114 and 1115 at a T-junction 1113 external to the fluidic lattice.

In certain embodiments, the first continuous fluid and the second continuous fluid may exhibit different surface affinities at the fluidic harbors or exhibit different interfacial relaxations within the fluidic harbors. Surface affinities may include contact angle, interfacial tension, capillary force, wetting, electrowetting, electrocapillarity, bonding, chemical or physical adsorption. For example, the second continuous fluid may exhibit a stronger tendency to reside within the fluidic harbors than the first fluid, thus unsettling the first fluid previously rendered stationary within the fluidic harbors.

In certain embodiments, the fluidic harbors may be modified with chemical or biological reagents to render the surfaces in contact with fluids preferential for wetting by either the first or second continuous fluid. For example, the surfaces may be modified to allow the second fluid to preferentially reside within the fluidic harbors, thus unsettling the first fluid previously rendered stationary at the fluidic harbors. The surfaces may also be modified to allow the first fluid to preferentially occupy the fluidic harbors, such that the second fluid would only unsettle a portion of first fluid.

In certain embodiments, a continuous fluid may contain a variety of analytes that include but are not limited to chemicals, biochemicals, genetic materials (DNA, RNA, etc.), expressed products of genetic materials (proteins, metabolites) crystallizing molecules, biological cells or particles.

A protrusion can be of a variety of shapes, dimensions, and offsets, both lateral and axial from the channel. For example, a protrusion could resemble a diamond, a pentagon, "L" shape, "T" shape, rectangle, or a triangle. 15. A cross-section a fluidic harbors may be T-shaped, L-shaped, triangular, rectangular, circular, elliptical, polygonal, or square. Within a fluidic lattice the fluidic harbors may be composed of more than one geometric shape and of more than one size in and in no particular repetitive motif. Other shapes for fluidic harbors are possible. The shape of the fluidic harbors may be modified such that different fluids with different interfacial tensions may exhibit different tendency to preferentially reside within the fluidic harbors.

Small fluidic packets are formed instantly in fluidic harbors rather than separate and distinct steps of droplet generation, followed by positioning of droplets in chambers. Droplet formation and positioning of droplets in a region may not be independent and distinct operations.

In certain embodiments, fluidic packets may assume the shape of the enclosing fluidic harbors.

In certain embodiments, small fluidic packets are formed by sequentially flowing continuous, rather than discontinuous (e.g. plugs, droplets or segments) fluids into a flow channel to occupy fluidic harbors.

In certain embodiments, a fluidic harbor generates fluidic packets without the need of an impedance region. Fluidic harbors are in fluidic communication with only one main flow channel.

Operation

Example 1: Generation of Packets in Fluidic Harbors with Three Fluids

There is more than one method by which samples may be discretized using our device. In Fill Method #1 (FIG. 2), the device is first filled with a fluid that is immiscible with the sample phase to be discretized. Next, the sample phase is slowly introduced into the device. Following this, the immiscible phase is flown through the device a second time. In this last step, the sample phase is displaced from the main channel yet remains in the sample compartments, discretizing the sample phase into a volume that is determined primarily by the geometric dimensions of the sample compartment. Sometimes, the discretization can occur during the initial sample phase filling step. For biological assays where the sample is in an aqueous solution, Fill Method #1 would involve filling the device first with an immiscible phase (e.g. oil or Fluorinert), followed by the sample (aqueous phase), and finally the immiscible oil phase is flown through the device a second time.

Figure 2:
FIG. 2. Schematic and sequence of images showing the use of Fill Method #1 for discretization of a sample. a) First, the chip is filled with a fluid (e.g. oil) that is immiscible with the sample phase (e.g. aqueous solution). b) Then sample phase is slowly introduced into the channel. c) Following this, immiscible phase is flown through the channel a second time. In this step, the sample phase is displaced from the main channel yet remains in the chambers, discretizing the sample phase into a volume that is defined primarily by the geometric dimensions of the chambers. The experimental time sequences (b and c) were made using 100 μM Alexa 488 as the sample phase and light mineral oil with 0.01% Span 80 as the immiscible phase. The scale bar corresponds to 200 μm.
Figure 2:
Figure 2:
Figure 2:
Figure 2:
Figure 2:
Figure 2:
Figure 2:
Figure 2:
Figure 2:
Figure 2:
Figure 2:
Figure 2:
Figure 2A:
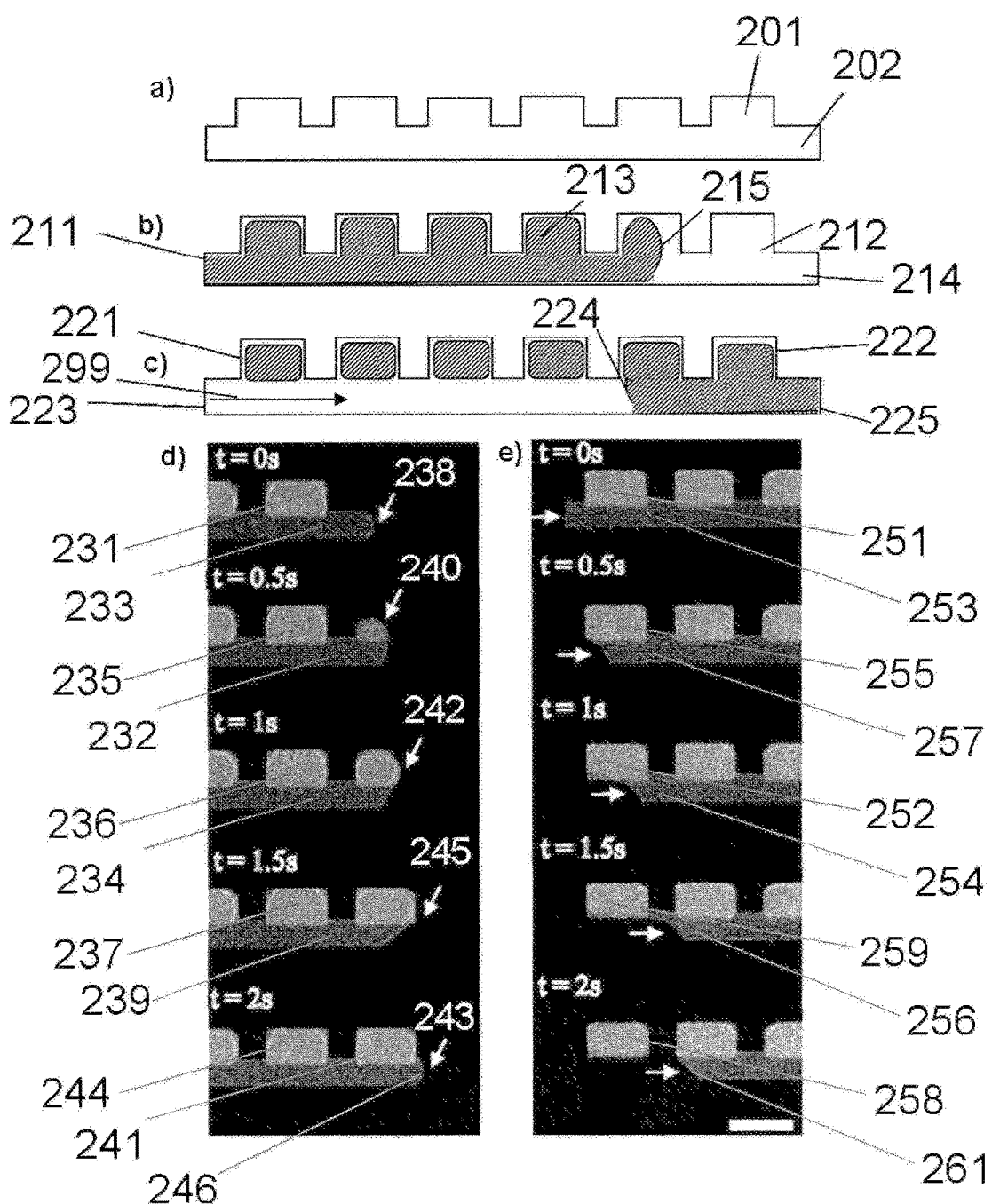
FIG. 2A. Schematic and sequence of images showing the fluidic behavior at the fluidic harbors in Example 1.

In this example, as shown in FIG. 2A(a), a primer continuous fluid 202 was flowed through a channel into a fluidic lattice containing fluidic harbors 201 that generate and shelter fluidic packets in the harbors. In FIG. 2A(b), a first continuous fluid containing analytes 211 was flowed through the fluidic lattice, unsettling the primer fluid 214. Following this, a second continuous fluid 223 was flowed through the fluidic lattice (FIG. 2A(c)), with the fluidic harbors offset from an axis 299 of flow through the channel. The fluorescent photographs in the lower section FIG. 2A(d, e) show the fluidic movements observed in the rectangular fluidic harbors.

In this example, the primer continuous fluid was light mineral oil containing 0.01% Span 80; the first continuous fluid was an aqueous solution containing 100 µM Alexa 488; and the second continuous fluid was the same as the first continuous fluid.

We note that as the rectangular fluidic harbors shelter fluidic packet 241 from the main flow 246 in channel 243, providing a relatively stress-free environment for the fluidic packet, the shape assumed by the fluidic packet was that of the fluidic harbor, rather than of a spherical droplet.

Figure 3:
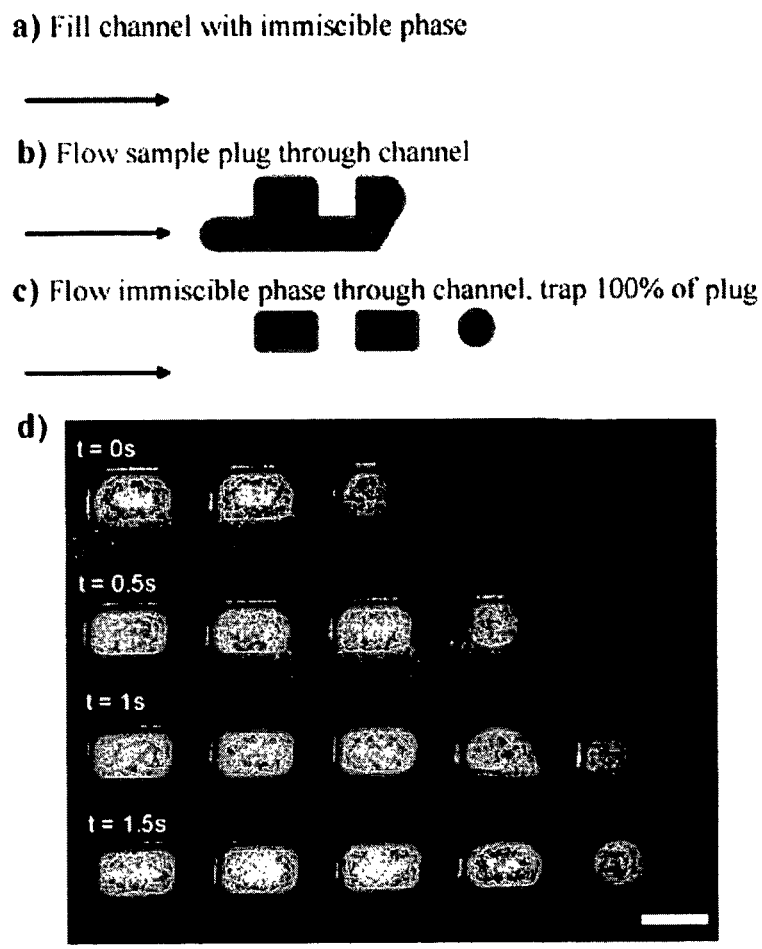
FIG. 3. A small sample volume can be introduced into the channel and completely discretized without any dead volume or loss of sample volume. a-c) Schematic depiction of the discretization and retention of 100 percent of a sample volume. d) An experimental time sequence illustrating this phenomenon. A small sample plug moving through the channel continues to fill each subsequent chamber and form droplets until the plug is gone. The images show the fluorescence of the sample phase (100 μM Alexa 488). The immiscible phase is light mineral oil with 0.01% Span 80 and the scale bar corresponds to 200 μm.

Fill Method #1 can be used to discretize 100% of a sample (FIG. 3). A small plug of sample moving through the main channel will continue to fill each subsequent chamber and divide into smaller volumes until the plug is gone. This is an important capability of our method for applications in which the amount of material to be analyzed is small, as is the case with many biological assays. Fill Method #1 is our preferred method of discretizing the sample volume for most applications.

Figure 3A:
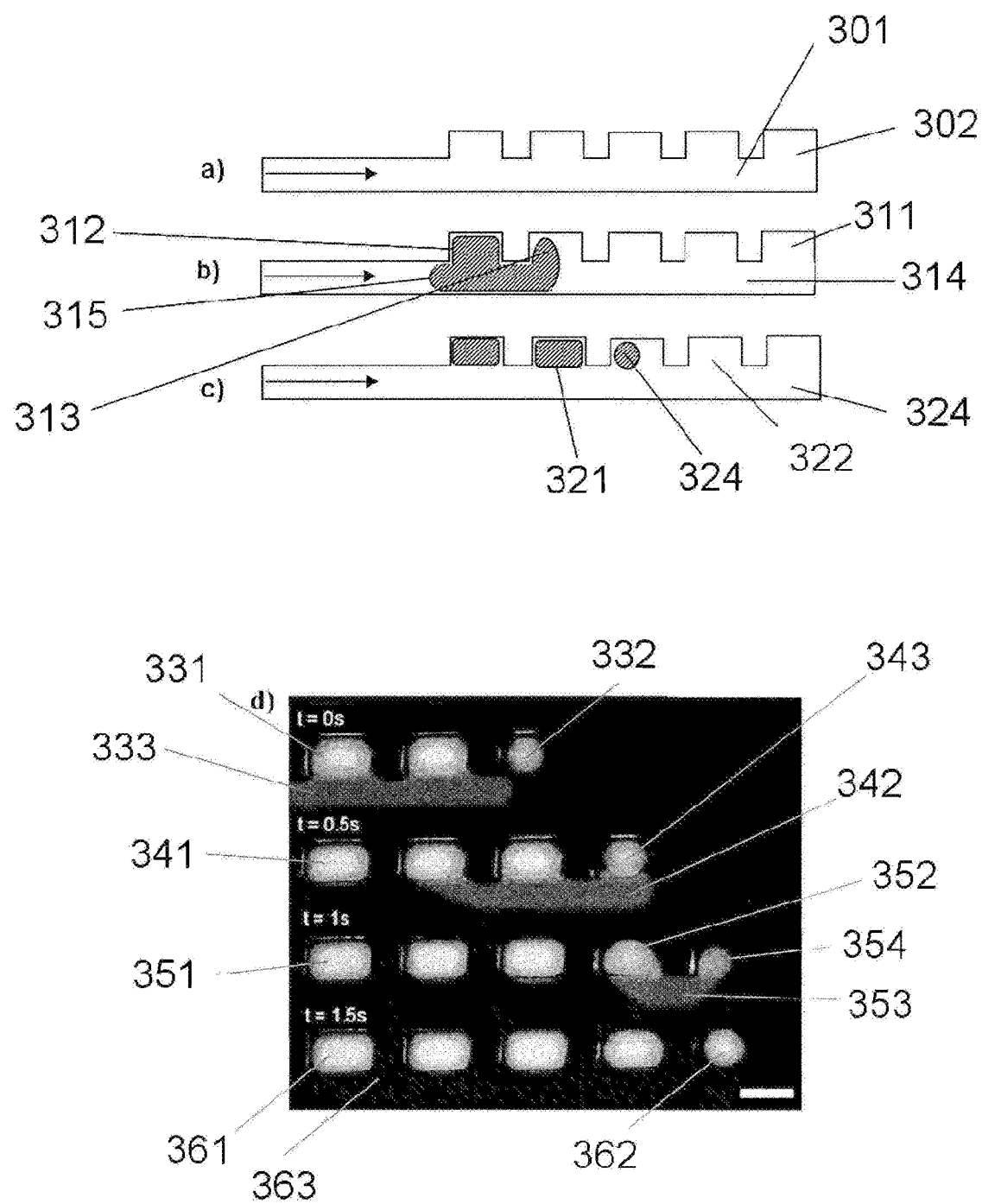
FIG. 3A. a-c) Schematic depiction of the generation of fluidic packets and the retention of 100 percent of a continuous fluid volume. d) An experimental time sequence illustrating this phenomenon.

In an embodiment the total volume of the fluidic packets generated is exactly the same as the incoming volume of the second continuous fluid. A continuous fluid volume can be introduced into the channel and completely converted into fluidic packets without any dead volume or loss of specimen. FIG. 3A(a-c) show a schematic of the packet-generation process and the resulting retention of 100 percent of a continuous fluid volume. As a channel is first filled with primer Fluid 314, followed by Fluid 315 to be transposed into fluidic packets for analysis, Fluid 315 continues to deconstruct into packets 321 until the last fluidic harbor retaining any residual continuous fluid that is less than the volume of a harbor. FIG. 3A(d) is an experimental time sequence illustrating this phenomenon. The images show the fluorescence of the fluidic packets (100 µM Alexa 488). The fluid depicted by 363 was light mineral oil with 0.01% Span 80 and the scale bar corresponds to 200 µm.

In an embodiment, the second fluid is transposed into fluidic packets in a reverse order. The rightmost portion of the second fluid is transposed into the leftmost fluidic packet, and as the left portion of the second fluid advances in the flow direction, the fluidic packets are generated to the right.

Example 2: Generation of Packets in Fluidic Harbors with Two Fluids

Figure 4:
FIG. 4. Schematic and sequence of images showing the use of Fill Method #2 for discretization of a sample. a) First, the chip is filled with the sample phase. b) Then, an immiscible phase is flown through the channel. In this step, the sample phase is displaced from the main channel yet remains in the chambers, discretizing the sample phase into a volume that is defined primarily by the geometric dimensions of the chamber. The experimental time sequence (c) was made by using 100 nM phosphate buffer as the sample phase and light mineral oil with 0.01% Span 80 as the immiscible phase. The scale bar corresponds to 200 μm.
Figure 4:
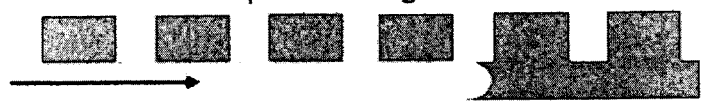
Figure 4:
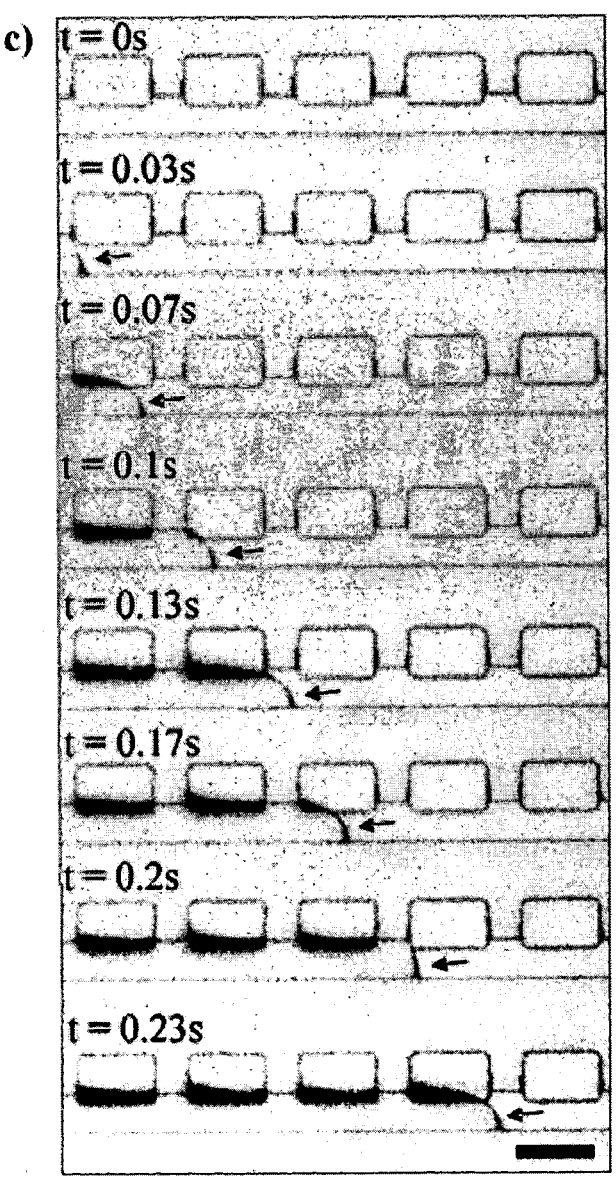

A second discretization method using our device is displayed in FIG. 4. In this method (Fill Method #2), the device is first filled with the sample phase. The sample phase is then discretized by flowing an immiscible phase through the main channel. For biological assays where the sample is in an aqueous solution, Fill Method #2 would involve filling the device first with the aqueous sample solution, followed by an immiscible phase, such as oil (e.g. mineral oil) or a fluorinated solvent (e.g. Fluorinert). Similar to Fill Method #1, as the immiscible phase flows through the device the sample phase is displaced from the main channel yet remains in the sample compartments. Again, the discretized sample volume is determined primarily by the dimensions of the sample compartment. With only two filling steps compared to the three of Fill Method #1, Fill Method #2 may be advantageous for certain applications.

Figure 4A:
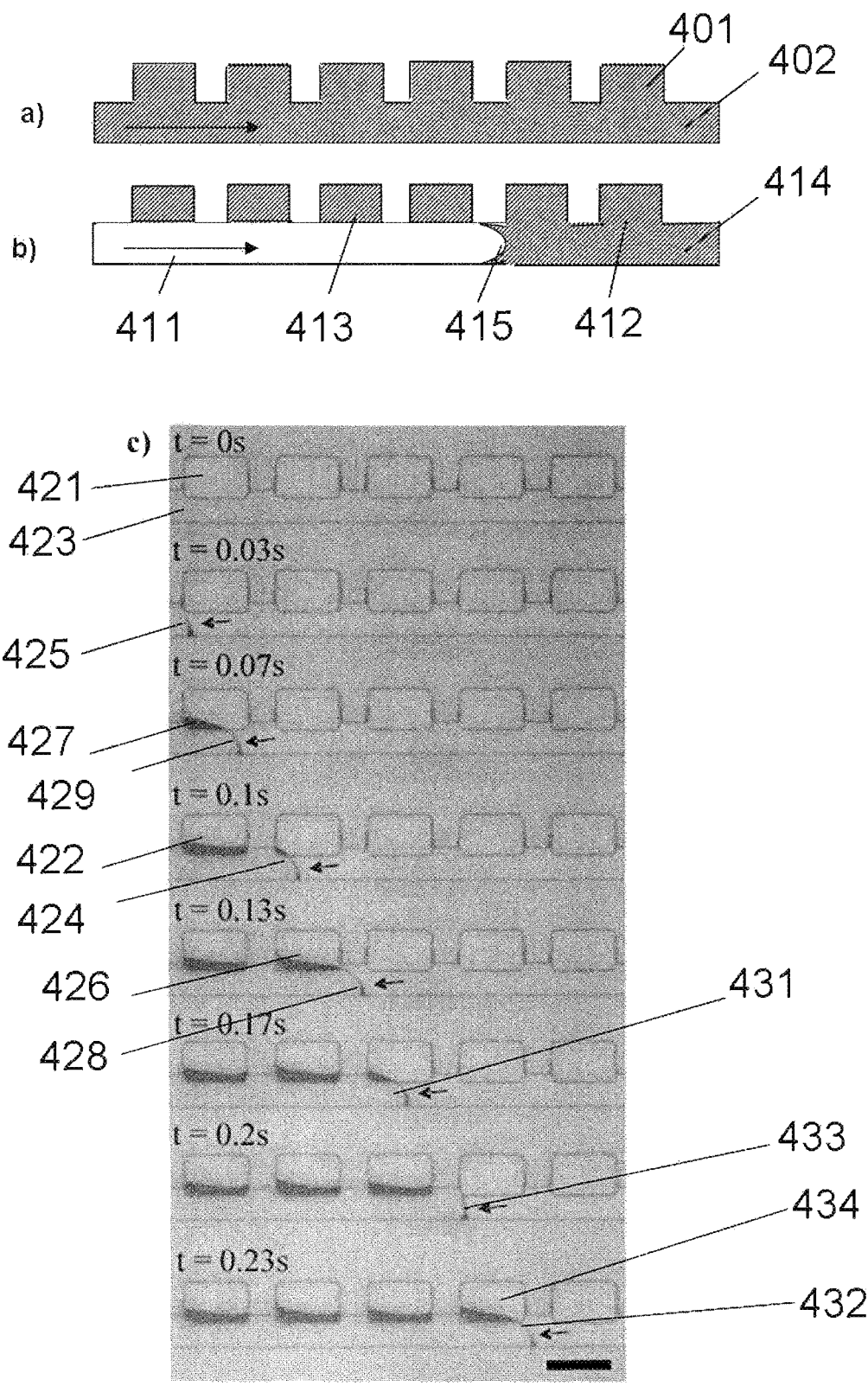
FIG. 4A. Schematic and sequence of images showing fluidic behavior at the fluidic harbors in Example 2.

In this example, as shown in FIG. 4A(a,b), only two continuous fluids were used to generate packets in fluidic harbors. A continuous first fluid 414 was flowed through a channel into a fluidic lattice containing fluidic harbors that generate and shelter the fluidic packet 413. A second continuous fluid 411 was then flowed through the fluidic lattice. FIG. 4A(c) shows sequential photographs of fluidic harbors as they generate fluidic packets of the first continuous fluid.

In the sequential images FIG. 4A(c), the first continuous fluid was an aqueous solution containing 100 nM phosphate buffer, and the second continuous fluid was a light mineral oil with 0.01% Span 80. The scale bar corresponds to 200 µm.

As the continuous first fluid is flowed through a channel into a fluidic lattice, the fluid enters fluidic harbors and is shielded from the velocity or velocity gradient of the main flow channel. The first fluid (aqueous) assumes the rectangular shape of the harbors as it accumulates. The second continuous fluid (oil) then unsettles the first fluid remaining in the main flow channel, forming rectangular-shaped fluidic packets in the fluidic harbors.

In an embodiment, the first fluid is transposed into fluidic packets in a reverse order. The rightmost portion of the first fluid is transposed into the leftmost fluidic packet, and as the left portion of the second fluid advances in the flow direction, the fluidic packets are generated to the right.

Figure 5:
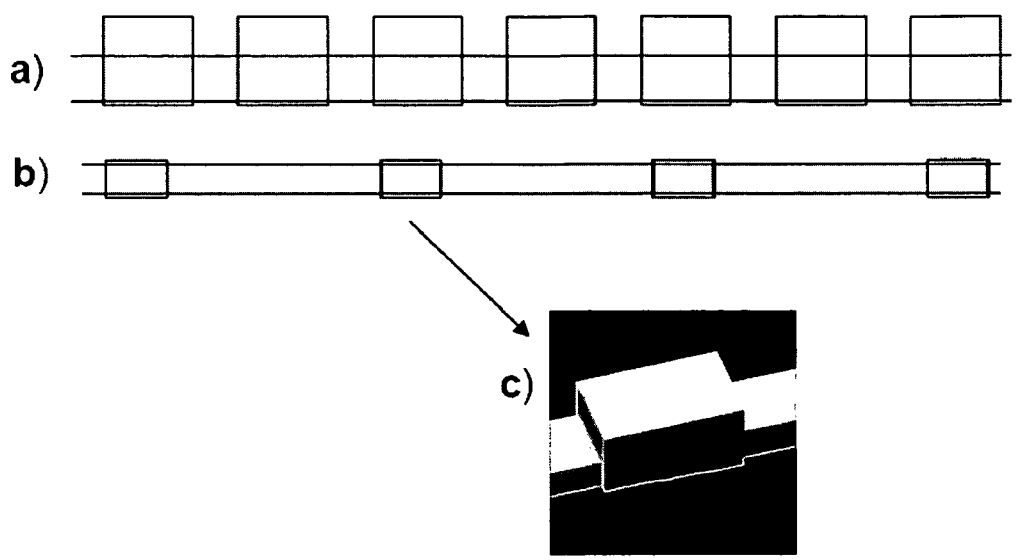
FIG. 5. A discretization device can be configured to retain species of different buoyancy. In order to discretize a sample using this method, the sample phase must be of a different buoyancy than the immiscible phase. a, b) Some examples of a design that is used to retain buoyant species, c) A three dimensional schematic of a sample compartment designed to retain buoyant species. The height of the sample compartment is greater than the height of the main channel. If the sample phase is more dense (i.e. heavier) than the immiscible phase, then a geometry that is inverted to what has been described can be used, that is, a chamber that is below the floor (rather than a chamber that is above the roof) of the channel can be used.

Example 3: Generation of Packets in Fluidic Harbors with Fluids of Different Densities An additional method that we have explored for sample discretization is based on exploiting a potential difference in the buoyancy of the sample and immiscible phases. In this method, the sample compartments reside either above or below the main channel, depending on whether the sample phase is more or less buoyant that the immiscible phase. If the sample phase is more buoyant than the immiscible phase, the compartments are placed above the main channel, if the sample phase is less buoyant than the immiscible phase, the compartments are below the main channel. FIG. 5 contains examples of potential discretization region geometries that may be used with this method. This method may be carried out by introducing either sample or immiscible phase into the device first, and then following the sequential flow outlined for Fill Methods 1 or 2. The specific flow sequence employed can be selected based on what is best suited for the particular application.

Figure 5A:
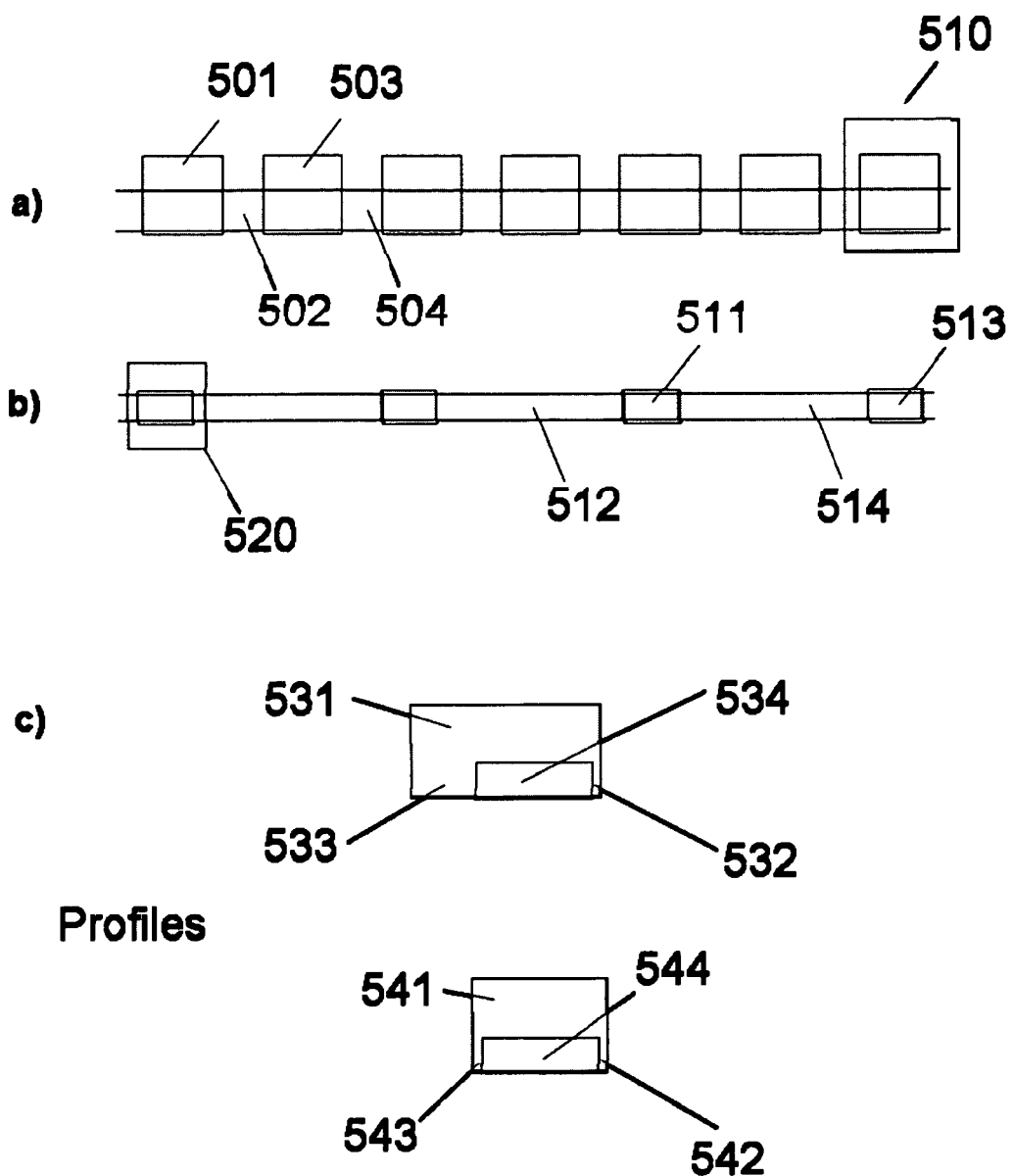
FIG. 5A. A fluidic lattice to generate fluid packets from fluids of different density or buoyancy.

In an embodiment, the fluids used in Example 1 or Example 2 may have different densities. In this example (see FIG. 5A), the fluidic harbors can reside in a plane either above or below the main flow channel, instead of in the same plane as the channel, but off the flow axis. If the fluid containing analytes is more buoyant than the other fluid(s), the fluidic harbors are placed above the main channel. If the fluid containing analytes is less buoyant than the other fluid(s), the fluidic harbors are positioned below the main channel. FIG. 5A(a,b) illustrates examples of fluidic harbors 501, 503, 511, 513 used to retain buoyant species. FIG. 5A(c) shows the corresponding profile schematics of panel a and panel b (upper refers to profile of area enclosed by outline 510, lower refers to profile of area enclosed by outline 520) showing a fluidic harbor 531 directly above a channel 534 intended to retain buoyant species. The height of the fluidic harbor is greater than the height of the channel. If the continuous fluid containing analyte is denser than the fluid that does not contain analyte, then the fluidic harbor is located below the main flow channel.

Figure 6:
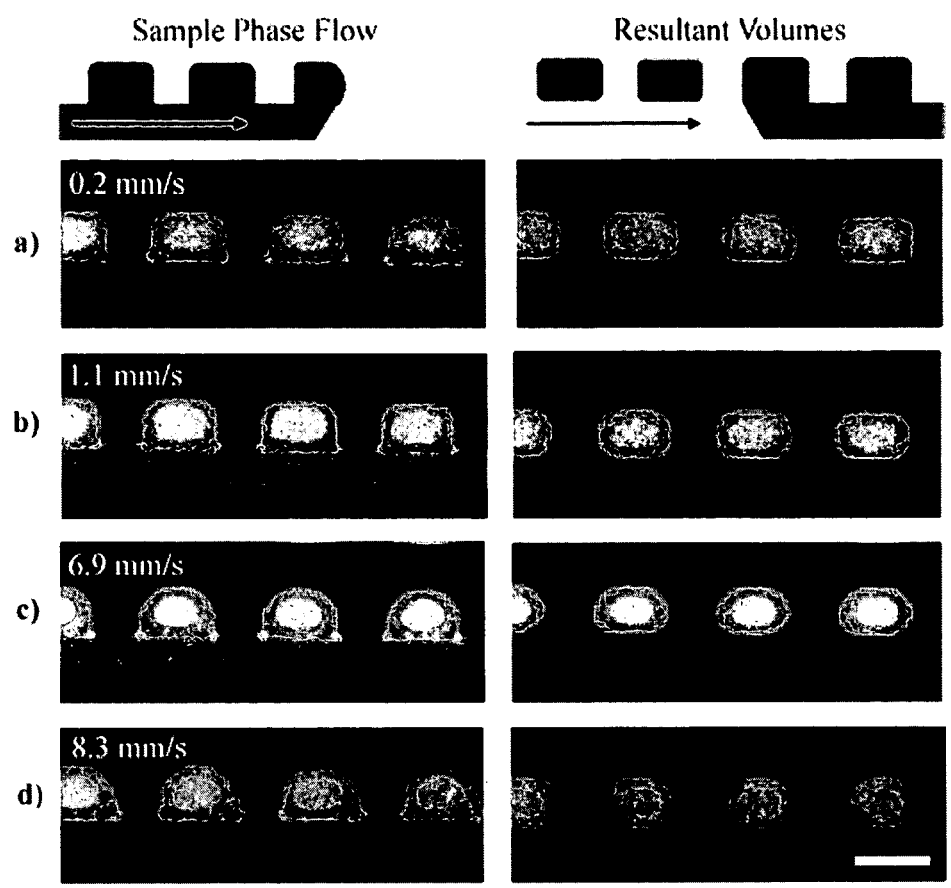
FIG. 6. Images depicting the effect of aqueous phase flow rate on discretization volume. In panels a), b), c) and d) the aqueous phase flow rates were 0.2, 1.1, 6.9 and 8.3 mm/s, respectively. The resultant droplet images that correspond to these flow rates indicate that the volume of the discretized sample is inversely proportional to the aqueous phase flow rate. The aqueous phase in these images is 100 μM 5,6-carboxyflourescein and the oil phase is light mineral oil with 0.01% Span 80. The scale bar corresponds to 200 μm.
Figure 7:
FIG. 7. Images depicting the effect of immiscible phase flow rate on discretization volume using Fill Method #2. a) Discretized samples formed with a fast immiscible phase flow rate. b) Discretized samples formed with a slower immiscible phase flow rate. The aqueous phase in these images is 100 nM phosphate buffer and the oil phase is Fluorinert. The scale bar corresponds to 200 μm.
Figure 7:

Example 4: Generation of Packets in Fluidic Harbors with Fluids at Different Flow Rates The volume of the discretized sample, while primarily determined by the sample compartment dimensions, may be more finely adjusted. One way of doing this can be achieved using Fill Method #1. As is shown in FIG. 6, a slowly flowing aqueous phase is capable of filling the sample compartment to a higher degree than a fast moving aqueous phase. This degree of filling is related to the final discretized sample volume. Therefore, the exact volume of the discretized sample may be tuned by adjusting the sample phase flow rate when using Fill Method #1. En Fill Method #2, the volume of the discretized sample can be varied by changing the immiscible phase flow rate (FIG. 7). When the immiscible phase flow rate is fast, some of the sample volume occupying each compartment is displaced, resulting in a smaller sample volume. When the immiscible flow rate is slower, the discretized sample will be larger.

In one embodiment, flow rates of the continuous fluids may be used to control the generation of fluidic packets in harbors. While the volume of the fluidic packet is primarily determined by the dimensions of the fluidic harbors, the flow rates of the continuous fluids can also be adjusted to affect the fluidic packet volume.

Figure 6A:
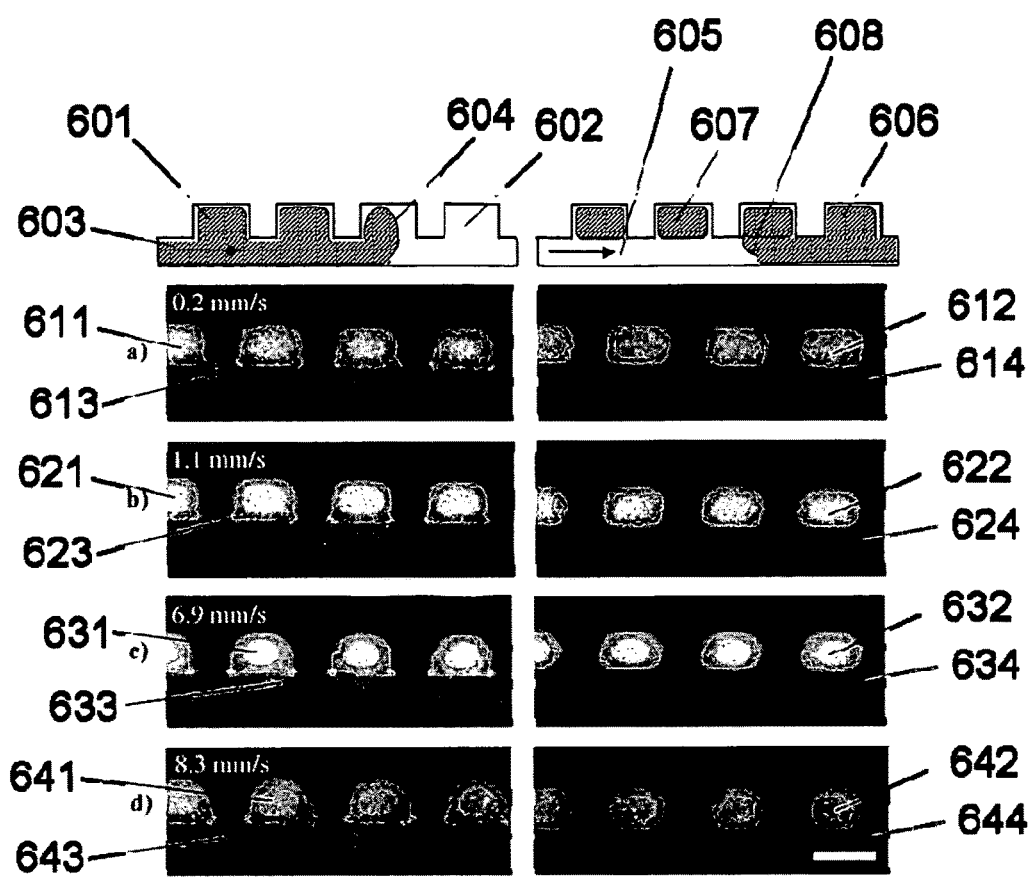
FIG. 6A. Images depicting the effect of the flow rate of the second continuous fluid on packet volume.

FIG. 6A displays a series of images showing the effect of continuous fluid flow rate on the volume of fluidic packets. Aqueous solution containing 100 μM 5,6-carboxyflourescein was used as the fluid containing analytes whereas light mineral oil with 0.01% Span 80 was the other continuous fluid(s).

As shown in FIG. 6A, a slowly flowing fluid can occupy the harbor to a higher degree than a fast moving fluid. As a result, the volume of the fluidic packets (aqueous solution of 100 μM 5,6-carboxyflourescein) is inversely proportional to the fluid flow rate, an acts as a secondary adjustment of packet volume where the primary adjustment is based on the harbor volume. The fluid velocities in FIG. 6A(a), (b), (c), and (d), were 0.2, 1.1, 6.9, and 8.3 mm/sec, respectively. The scale bar corresponds to 200 μm. Fluidic packet 642, generated at 8.3 mm/sec of the aqueous solution, was visibly smaller than Fluidic packet 612, generated at 0.2 mm/sec.

Figure 7A:
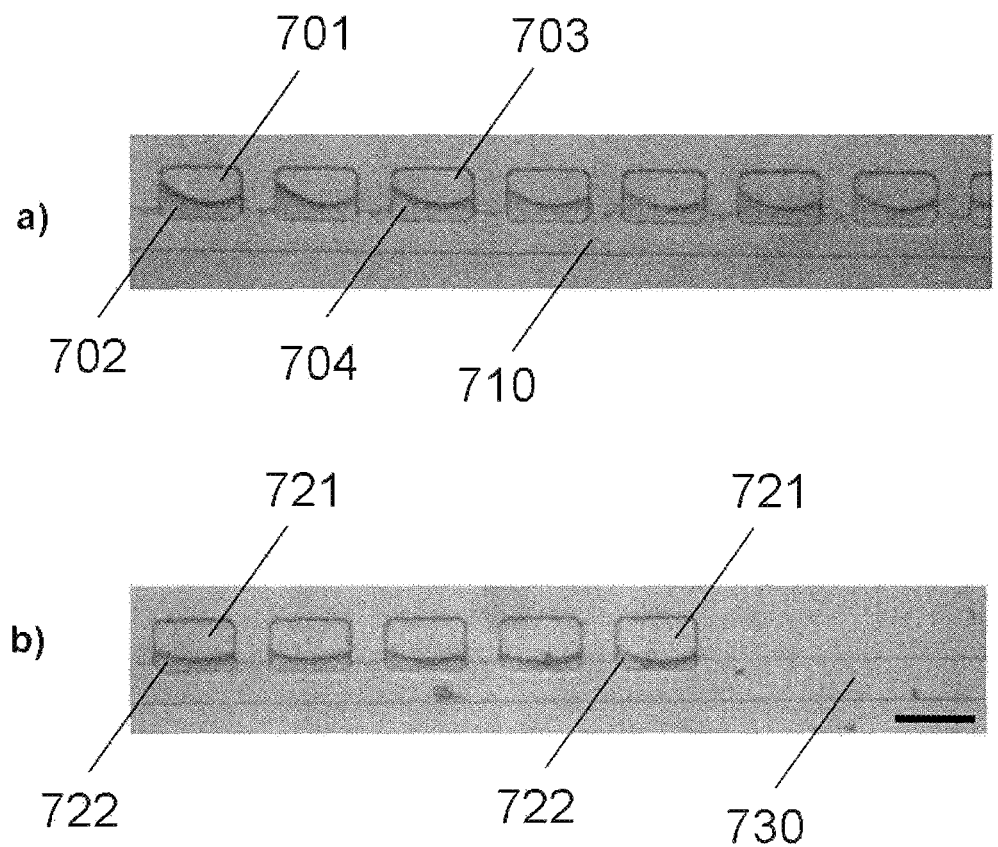
FIG. 7A. Images depicting the effect of the flow rate of other continuous fluid(s) on packet volume.

Alternatively, the flow rates of other fluid(s) can be adjusted to control the packet volume. When the flow rate of the second continuous fluid of packets that were generated using the method depicted in EXAMPLE 2 was increased, the fluidic harbors did not offer sufficient sheltering from the high velocity in the main flow channel. FIG. 7A(a) shows that more aqueous phase containing analytes were unsettled by the oil (organic) phase at a higher flow rate, resulting in smaller fluidic packets 701. When the flow rate of the oil (organic) phase was slowed down FIG. 7A(b), the fluidic harbor was occupied by a larger fluidic packet 721. The aqueous phase in these images was 100 nM phosphate buffer and the oil phase was Fluorinert. The scale bar corresponds to 200 μm.

Example 5: Generation of Packets in Fluidic Harbors with Different Fluids

Figure 8:
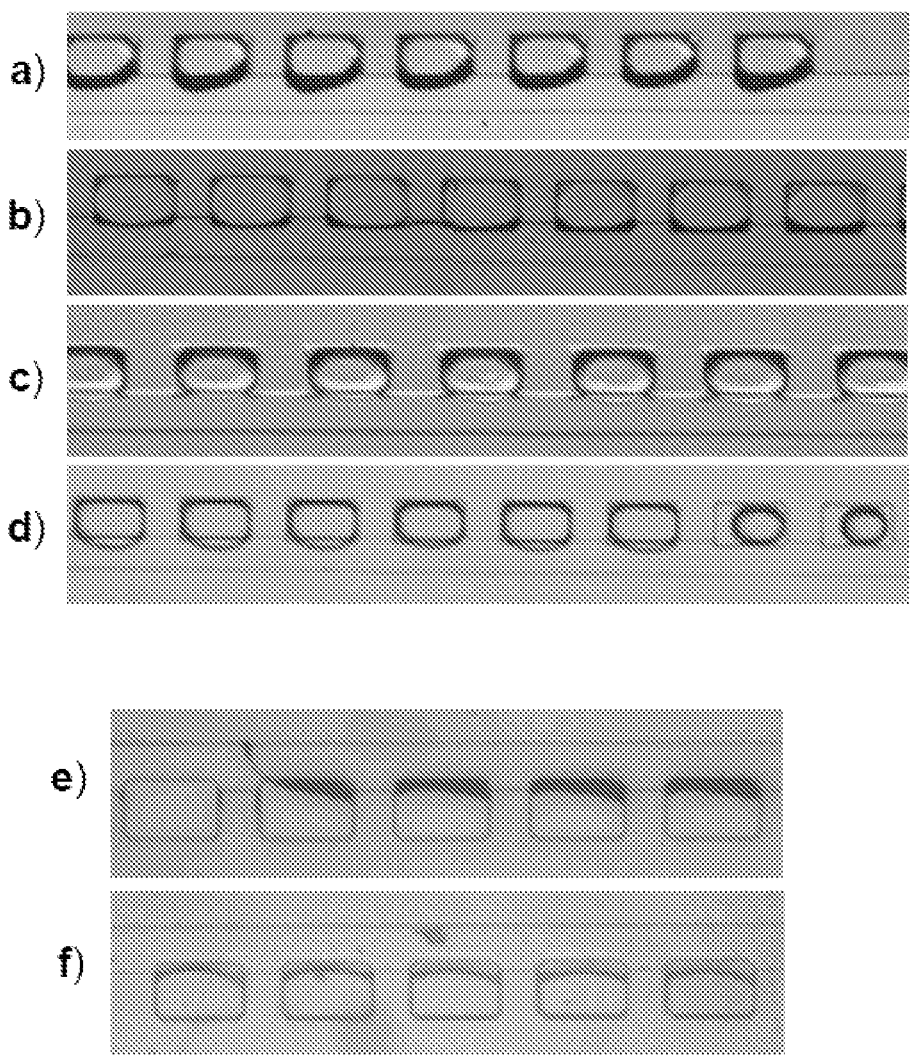
FIG. 8. Examples of small volumes which have been discretized by Fill Method #1 (a, b, c, d) and Fill Method #2 (e, f) using different immiscible phases. The immiscible phases used to form the samples shown are a) light mineral oil with 0.01% Span 80, b) Fluorinert, c) AS-4, d) AR-20, e) light mineral oil, and f) Fluorinert.

It is possible to discretize a sample using a wide variety of immiscible phases. Some immiscible phases include, but are not limited to natural oils such as mineral oil and soybean oil, silicone oils such as AR-20, AS-4, PDMS oil, fluorinated oils such as Fluorinert and perfluorordecalin, and organic solvents such as hexadecane and acetophenone. A selection of sample images that have been discretized using different immiscible phases are shown in FIG. 8.

In one embodiment, the fluid(s) not containing analytes may include natural oils such as mineral oil and soybean oil, silicone oils such as AR-20, AS-4, PDMS oil, fluorinated oils such as Fluorinert and perfluorordecalin, organic solvents such as hexadecane and acetophenone, or aqueous solutions such as buffer or water.

Figure 8A:
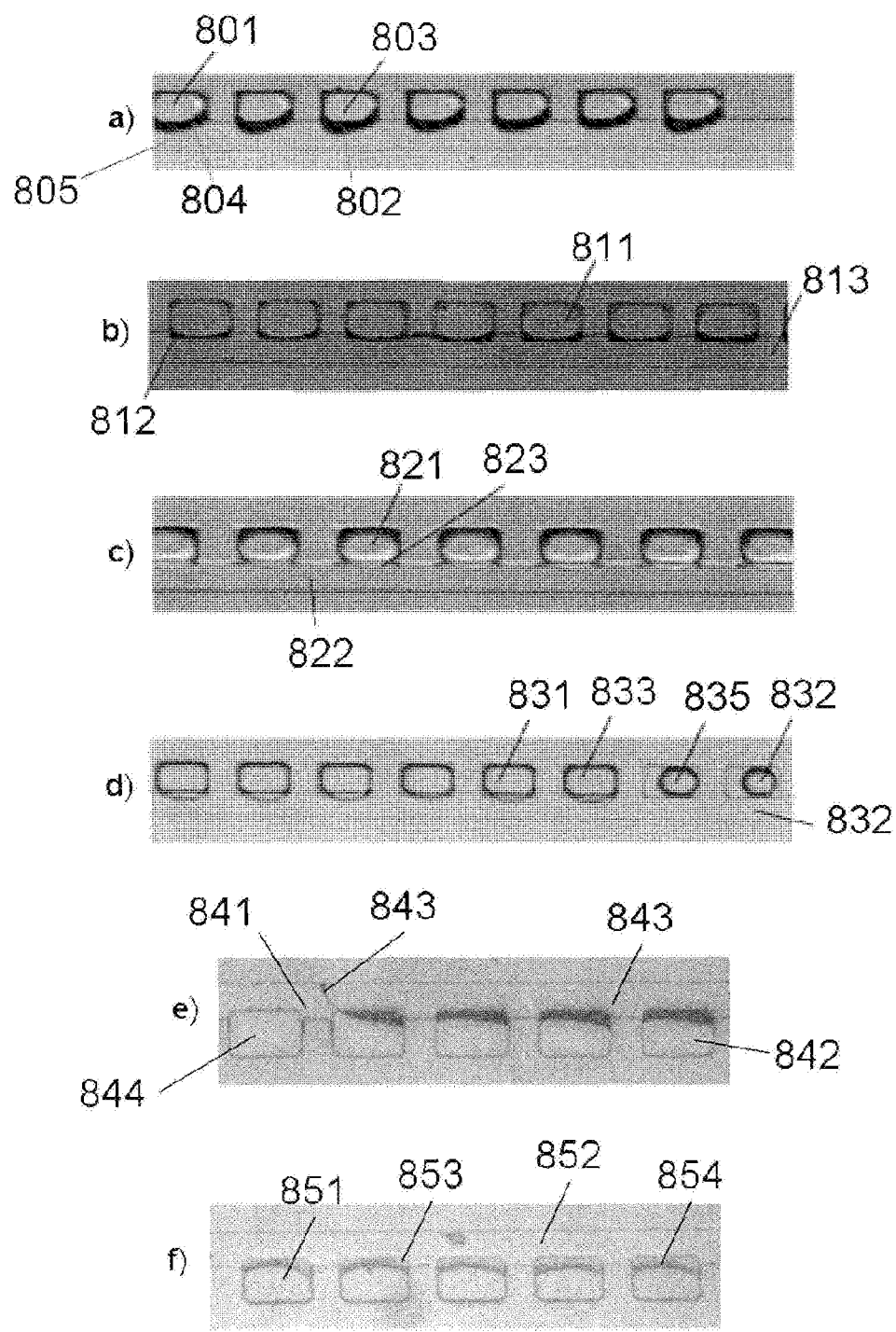
FIG. 8A Images of fluidic packets formed using different continuous fluid(s).

FIG. 8A shows the fluidic packets formed when different fluid(s) were used. The continuous fluids not containing analyte that were used to form the fluidic packets as in Example 1 were: light mineral oil with 0.01% Span 80 (panel a), Fluorinert (panel b), AS-4 silicone oil (panel c), AR-20 silicone oil FIG. 8A(d). The continuous fluids not containing analyte that were used to form the fluidic packets as in Example 2 were: light mineral oil FIG. 8A(e), and Fluorinert oil FIG. 8A(f).

Example 6: Generation of Packets in Fluidic Harbors with Various Surfactants

Figure 9:
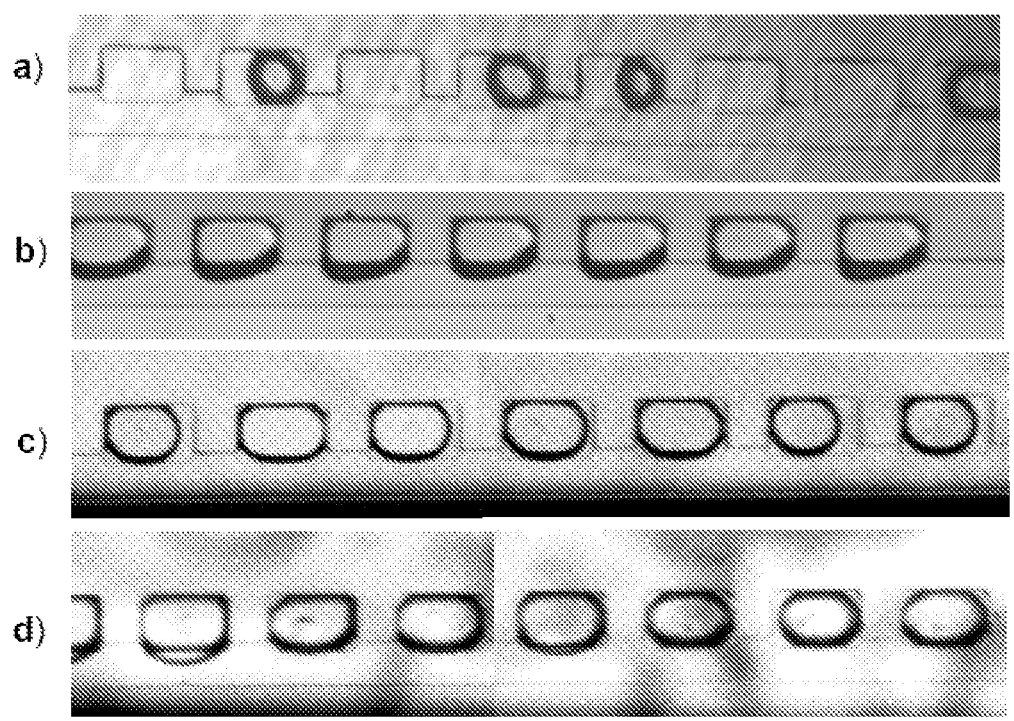
FIG. 9. Surfactant can be added to facilitate discretization. a) Discretization that has been attempted using pure light mineral oil. b) Samples that have been discretized using light mineral oil with 0.01% Span 80. c) Samples that have been discretized using light mineral oil with 0.01% octaethylene glycol monodecyl ether. d) Samples that have been discretized using light mineral oil with 0.01% tetraethylene glycol monodecyl ether.

In some cases, the discretization dynamics can be adjusted with the use of surfactant. FIG. 9 contains images of sample that have been discretized without surfactant in addition to samples that have been discretized using a variety of surfactants. Surfactant can be used to aid in the formation of a discretized sample from a large volume of sample. The surfactant employed is not limited to those examples shown in FIG. 9, and can include, for example, non-ionic surfactant such as sorbitan monooleate (SPAN 80), zwitterionic surfactant such as N-dodecyl-N, N-dimethyl-3-ammonio-1-propanesulfonate (DDAPS), anionic surfactant such as sodium dioctyl sulfosuccinate (AOT), cationic surfactant such as cetyl trimethyl ammonium bromide (CTAB), and more importantly, PEGylated and fluorinated surfactants that may be particular useful for certain biological assays.

Figure 9A:
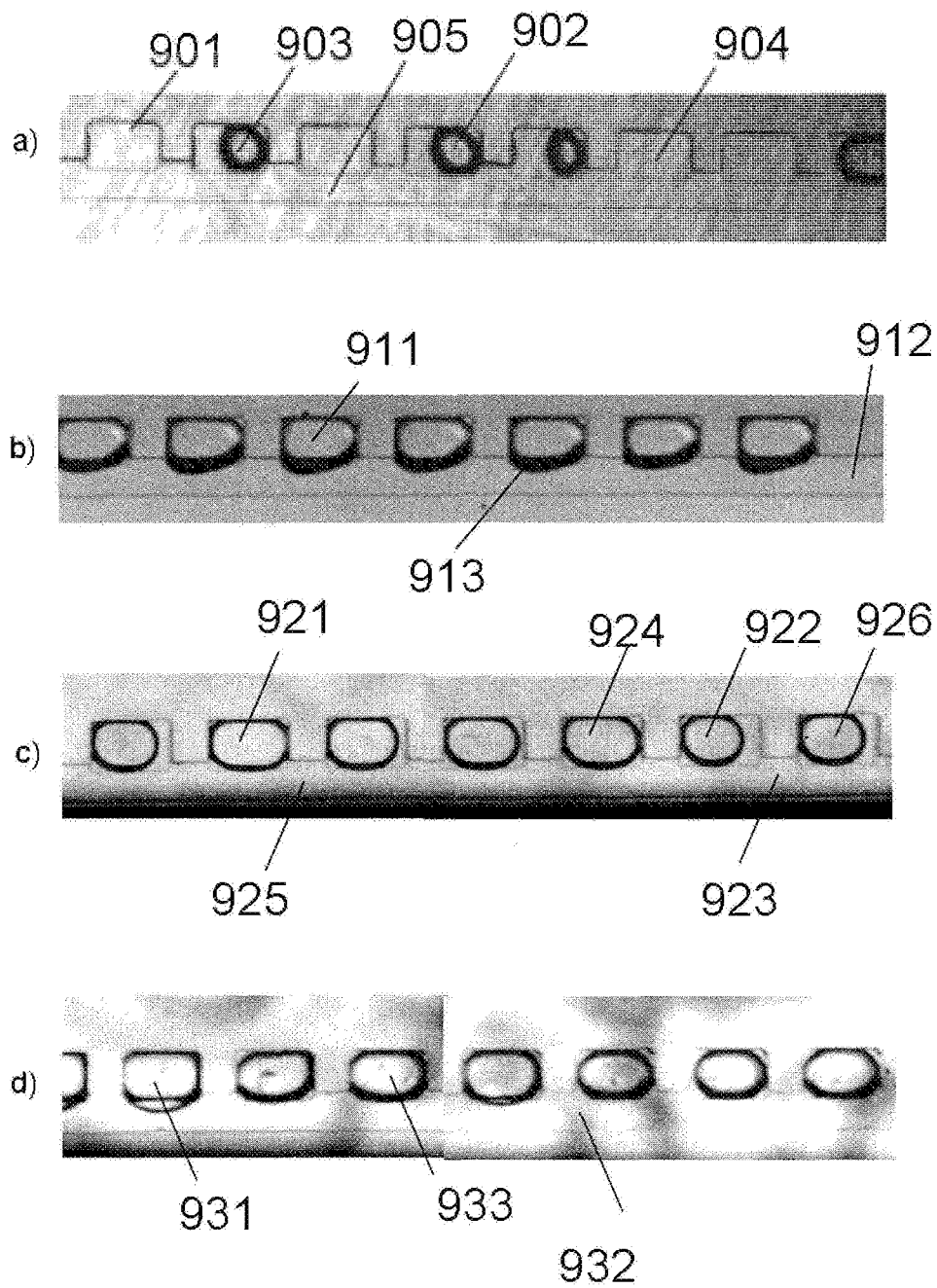
FIG. 9A. Examples of surfactants useful for generating fluidic packets in fluidic harbors.

In certain embodiments, surfactants are added to one or more of the fluids to aid the generation of fluidic packets in harbors. In FIG. 9A surfactants such as Span 80, octaethylene glycol monodecyl ether, and tetraethylene glycol monodecyl ether were systematically added to light mineral oil to investigate their effects on fluidic packet formation. FIG.

9A(a) shows an image of aqueous fluidic packets in pure light mineral oil. FIG. 9A(b) shows an image of aqueous fluidic packets in light mineral oil with 0.01% Span 80 surfactant. In FIG. 9A(b) the shape of the fluidic packets now matches that of the harbors. FIG. 9B(c) is an image of aqueous fluidic packets in light mineral oil containing 0.01% octaethylene glycol monodecyl ether. The shape of fluidic packets in this instance matches that of the harbors. FIG. 9B(d) is an image of aqueous fluidic packets in light mineral oil containing 0.01% tetraethylene glycol monodecyl ether. In FIG. 9B(c and d), the shape of the fluidic packets matches that of the harbors.

In addition to the surfactants used in FIG. 9A, other surfactants could also be incorporated for the purpose of forming fluidic packets in harbors. Other surfactants include but are not limited to zwitterionic surfactants such as N-dodecyl-N,N-dimethyl-3-ammonio-1-propanesulfonate (DDAPS), anionic surfactants such as sodium dioctyl sulfosuccinate (AOT), cationic surfactants such as cetyl trimethyl ammonium bromide (CTAB), and more importantly, Silicone based, PEGylated and fluorinated surfactants that may be particularly useful when minimal interaction between the bulk fluid in the packet and the surrounding phase and/wall are desired.

Figure 10:
FIG. 10. The ability of a device to dicretize may be adjusted by modifying the surface properties of the device substrate. a, b and c) Schematic depiction of the lack of discretization of a sample phase which has been introduced into the device using Fill Method #1 in devices with unsuitable surface properties, b, c) An experimental time sequence illustrating this phenomenon. The sample phase introduced into the device in panel b) in not retained during subsequent immiscible phase flow as is shown in c). The experimental images in b and c) show the fluorescence of the sample phase consisting of 100 μM carboxyfluorescein. The immiscible phase is light mineral oil with 0.01% Span 80 and the scale bar corresponds to 200 μm.
Figure 10:
Figure 10:
Figure 10:
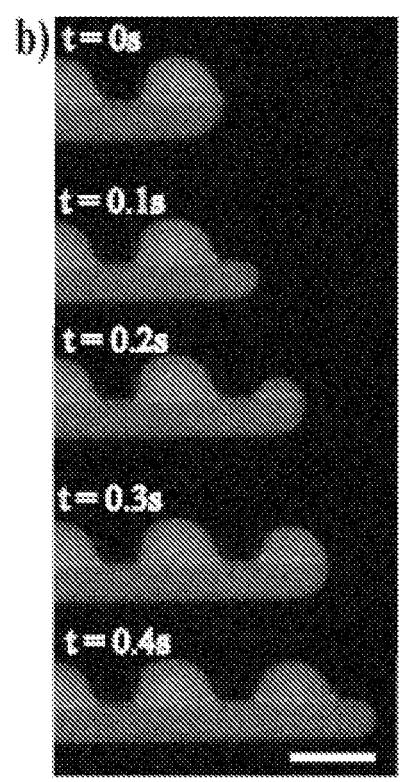
Figure 10:
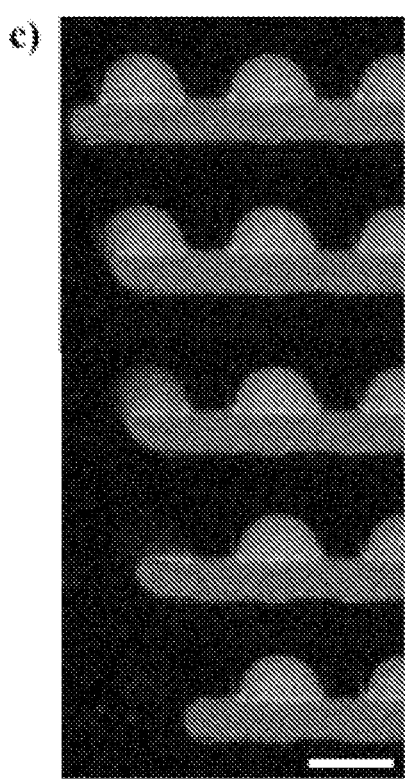

Example 7: Generation of Packets in Fluidic Harbors with Chemically Modified Walls Another parameter, the surface of the discretization region, may be modified in order to define the discretization ability of the device. The device shown in FIG. 10 is a glass/PDMS chip that was filled with light mineral oil with 0.01% Span 80 immediately after oxidizing the two surfaces (PDMS and glass) and bringing them into contact to form the device. When the sample phase was introduced into this chip, followed by more immiscible phase flow, no discretized samples are formed. In contrast, the device shown in FIG. 2 is a PDMS chip similar to that in FIG. 10 but that has been baked at 115° C. for 48 hours following device formation. When the device shown in FIG. 2 is filled with light mineral oil with 0.01% Span 80, and sample phase is introduced into the chip, followed by more immiscible phase flow, discretized samples are easily formed. Therefore, surfaces of the device can be modified in order to dictate whether or not discretization will occur.

Figure 10A:
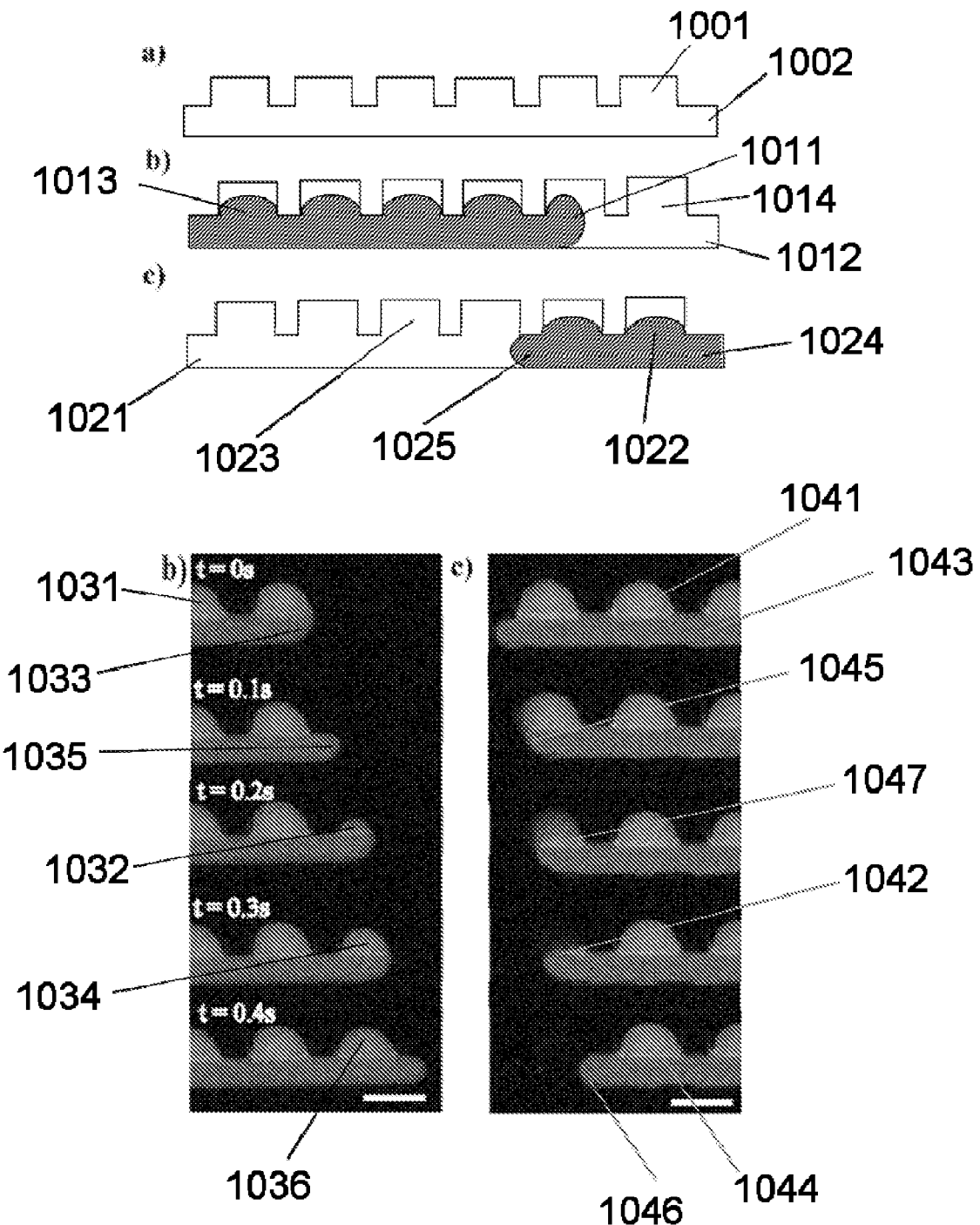
FIG. 10A. Absence of fluidic packet generation when surface properties of a fluidic lattice were altered.

In certain embodiments, the walls of fluidic harbors may be chemically modified to increase the surface affinity of the continuous fluids. For example, FIG. 10A shows a fluidic lattice constructed out of polydimethylsiloxane (PDMS) and glass. The fluidic lattice was oxidized with oxygen plasma prior to executing the flow protocol described in Example 1. The first continuous fluid in this instance was a light mineral oil containing 0.01% Span 80; the second continuous fluid was an aqueous phase containing analytes; and the third continuous fluid was the same as the first fluid. We note that no fluidic packets (FIG. 10A(b-c)) were formed when the walls of the harbors were freshly oxidized. The fluid that entered into fluidic harbors did not assume the shape of the harbor, nor did it interact significantly with the walls of the harbor.

Another fluidic lattice, also oxidized in oxygen plasma, was baked at 115° C. for 48 hours after oxidation. The extended baking rendered the walls of harbors hydrophobic (or oleophillic). The protocol described in Example 1 and in the previous paragraph was executed. As shown in FIG. 2A(b,c), fluidic packets were readily formed in the harbors in this instance.

Additionally, the wall surfaces of fluidic harbors may be modified chemically to enhance wetting or to assist in the adsorption of select chemical, fluids, cells, particles, or molecules. Surface-modification chemicals may include, but are not limited to, silanes such as trimethylchlorosilane (TMCS), hexamethyldisilazane (HMDS), (Tridecafluoro-1, 1,2,2-tetrahydrooctyl)trichlorosilane, chlorodimethyloctylsilane, Octadecyltrichlorosilane (OTS) or γ-methyaeryloxypropyltrimethyoxy-silane; polymers such as acrylic acid, acrylamide, dimethylacrylamide (DMA), 2-hydroxyethyl acrylate, polyvinylalcohol (PVA), poly(vinylpyrrolidone (PVP), poly(ethylene imine) (PEI), Polyethylene glycol (PEG), epoxy poly(dimethylacrylamide (EPDMA), or PEG-monomethoxyl acrylate; surfactants such as Pluronic surfactants, Poly(ethylene glycol)-based (PEG) surfactants, sodium dodecylsulfate (SDS) dodecyltrimethylammonium chloride (DTAC), cetyltriethylammonium bromide (CTAB), or Polybrene (PB); cellulose derivatives such as hydroxypropylcellulose (HPC), or hydroxypropylmethylcellulose (HPMC); amines such as ethylamine, diethylamine, triethylamine, or triethanolamine, fluorine-containing compounds such as those containing polytetrafluoroethylene (PTFE) or Teflon.

Manufacture

Example devices fabricated and demonstrated here and shown in the figures are made from polydimethylsiloxane (PDMS) or/and glass. Besides PDMS and glass, other preferred substrates include but are not limited to silicon, thermoset polyester (TPE), polymethylmethacrylate (PMMA), polyethylene, polyester (PET), polytetrafluoroethylene (PTFE), polycarbonate, parylene, polyvinyl chloride, fluoroethylpropylene, lexan, polystyrene, cyclic olefin copolymers, polyurethane, polyurethane blended with polyacrylate, polyestercarbonate, polypropylene, 25 polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide, polyimide), inorganic materials (glass, quartz, silicon, GaAs, silicon nitride), fused silica, ceramic, glass (organic), metals and/or other materials and combinations thereof. For biological assays, the preferred substrate is based on a polymer material so the device is disposable for one-time use.

Geometric Parameters

Example 8: Generation of Packets in Fluidic Harbors of Various Shapes

In order to introduce liquids into the device, a variety of different options exist depending on both the material that the device has been fabricated from and the filling method of interest. A minimum of two fluids must be used in order to discretize a sample using our device. Methods to switch between fluids include but are not limited to built in channels for different phases within the device (FIG. 11(a)), on-chip valving, or control by an offline valve (FIG. 11(b)). An offline valve can be adjusted to choose the phase that is introduced to the chip, and an on-chip valve can control the type of fluids in the chip that are introduced into the discretization region. Different phases can be introduced into the discretization region of the device sequentially. When multiple channels are involved, the different solutions can be introduced into different channels in parallel, sequentially, or according to some predefined sequence and may be automated.

Figure 12:
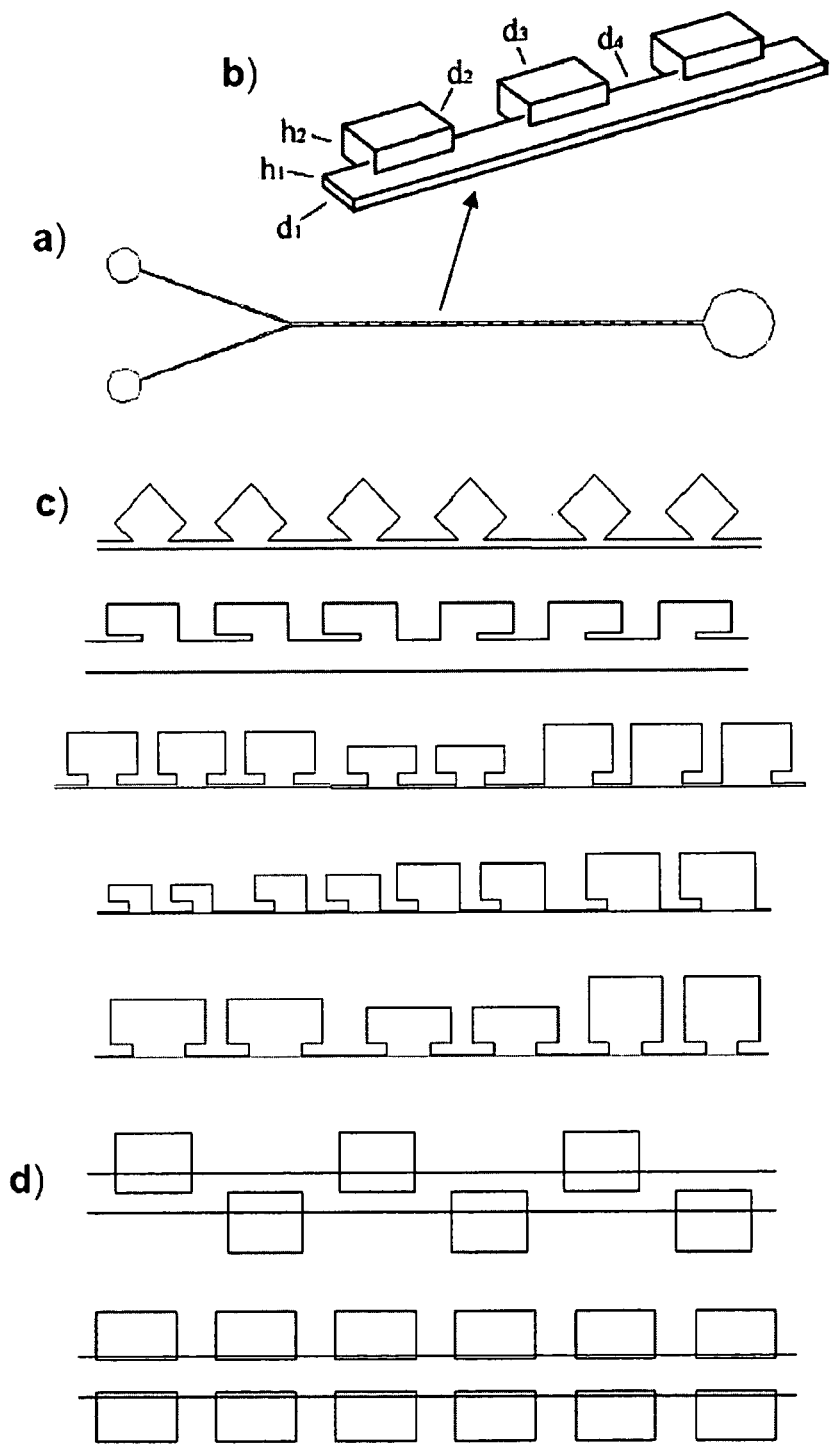
FIG. 12. The discretization region of the device may be optimized to best suit the application, a, b) Dimensions of the discretization region. It is possible to vary any or all of these dimensions. It is also possible to change the shape of the sample compartments. c) Some examples of different sample compartment variations. These sample compartments may be of the same height as the main channel or may be of a different height. d) Some examples of different locations of the sample compartments with respect to the main channel. The orientation of these chambers may be optimized to suit different applications.
Figure 13:
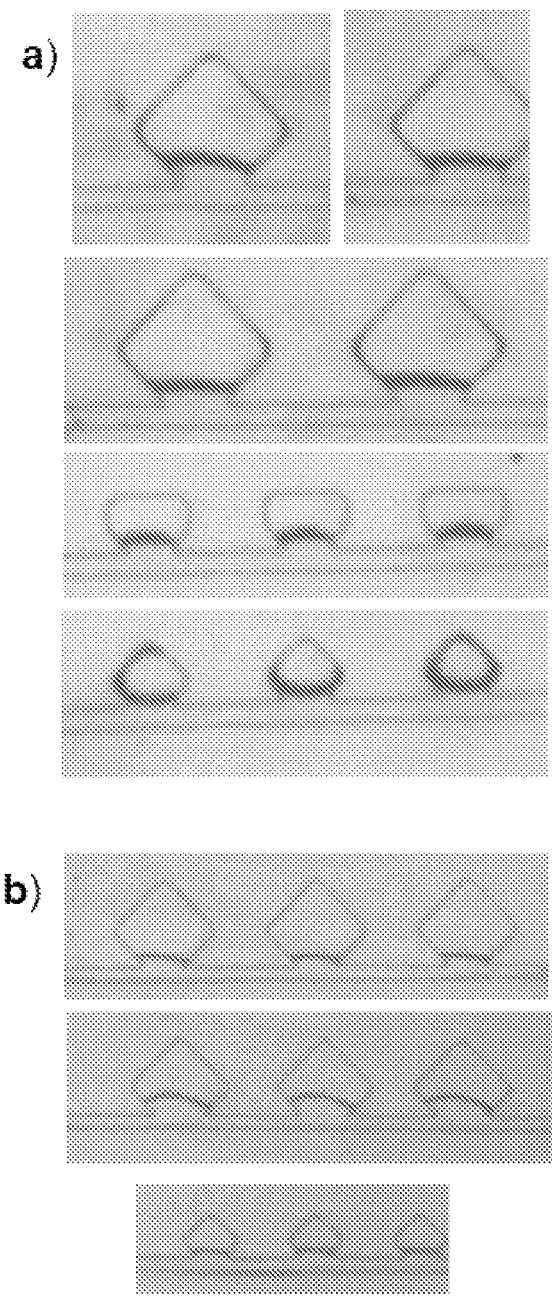
FIG. 13. Aqueous samples that have been discretized using some examples of differently shaped sample compartments. a) Light mineral oil with 0.01% Span 80 was used as the immiscible phase. b) Fluorinert was used as the immiscible phase.

The dimensions of the discretization region are flexible and may be adjusted to best fit the application of interest. Variations of the discretization region may include, but are not limited to, those shown in FIG. 12. FIG. 12(b) offers an example of some of the geometric parameters that may be varied in the design of a discretization device. A selection of geometries shown in FIG. 12(c) provides a sampling of some possible options, including a variety of different sample compartment shapes. Potential sample compartment shapes are not limited to those shown. The sample compartments may be of the same height, or a different height than the main channel. One embodiment has a different height for the chamber than the main channel, such as that depicted in FIG. 1(b). FIG. 12(d) displays examples of different locations of the sample compartments with respect to the main channel. The orientation of these compartments may be optimized to suit different applications. FIG. 13 contains images of samples that have been discretized using devices with a selection of differing discretization region geometries.

Figure 12A:
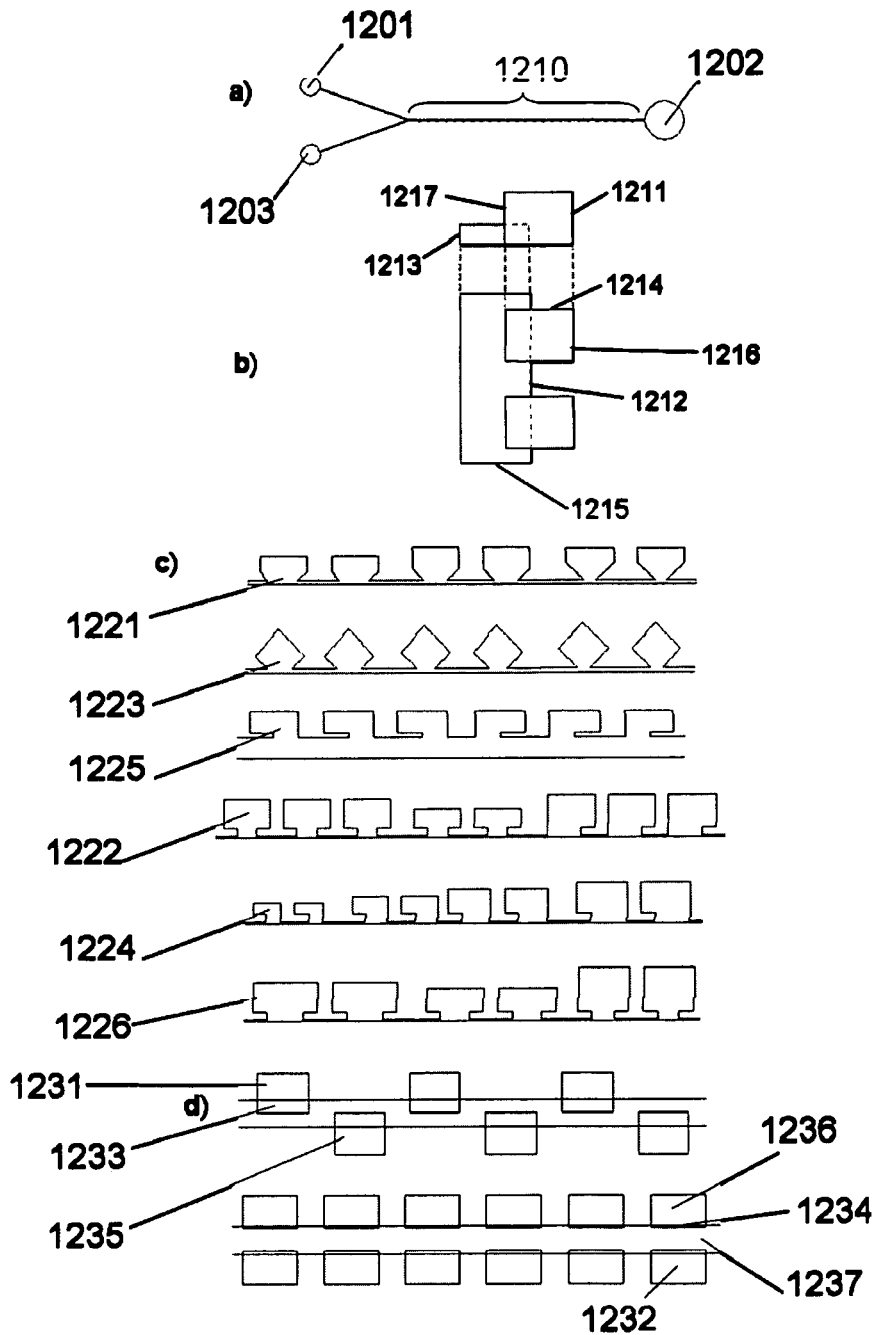
FIG. 12A. Various geometric shapes of fluidic harbors.

Various in plane and out of plane geometric shapes of fluidic harbors are possible and some examples are depicted in FIG. 12A. For example, fluidic harbors could resemble a diamond, a pentagon, "L" shape, "T" shape, rectangles, or triangles. Within a fluidic lattice the fluidic harbors may be composed of more than one geometric shape and of more than one size in and in no particular repetitive motif. Multiple geometric subunit shapes for fluidic harbors are possible.

Figure 13A:
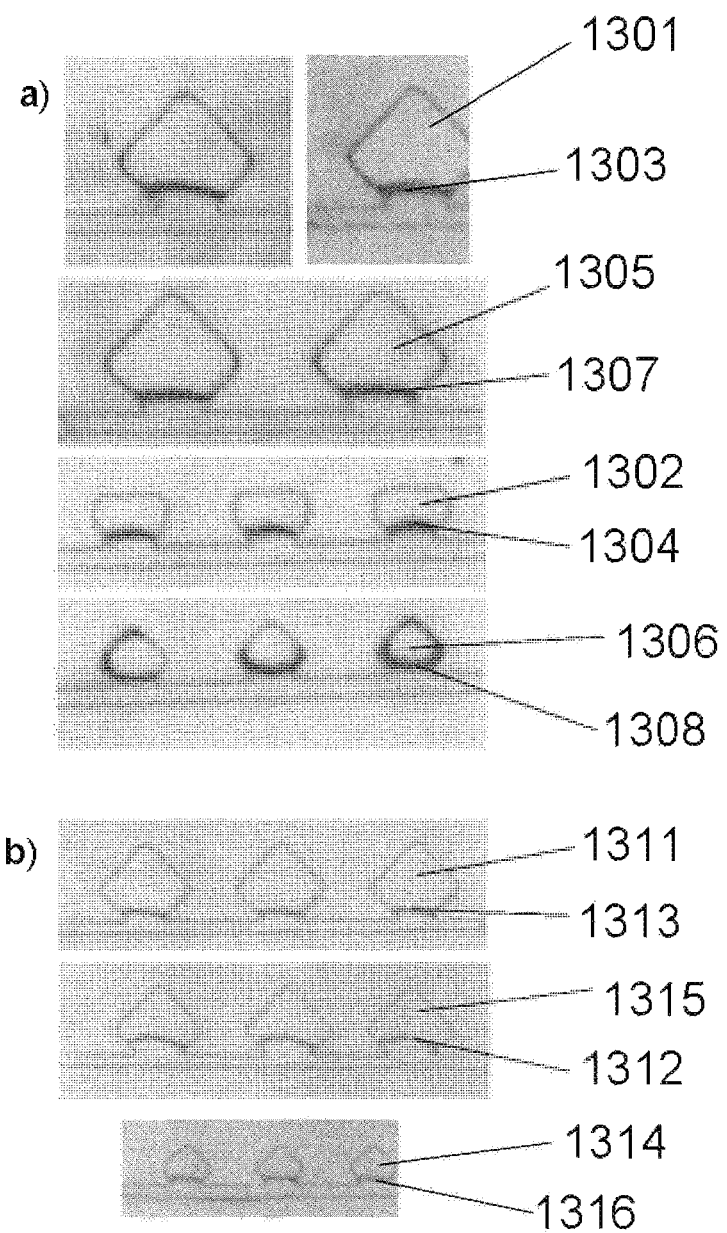
FIG. 13A. Images of fluidic packets generated in fluidic harbors of various shapes.

FIG. 13A shows images of fluidic packets generated in fluidic harbors of various shapes, including diamond shape and T-shape.

In an embodiment, the height of a fluidic harbor may be taller than the flow channel to which it connects. A difference in height may be exploited for generating fluidic packets from fluids of different densities or buoyancy, or with different energies involved in interfacial relaxation. In an embodiment, the height of a fluidic harbor may be shorter than the flow channel to which it connects.

Figure 14:
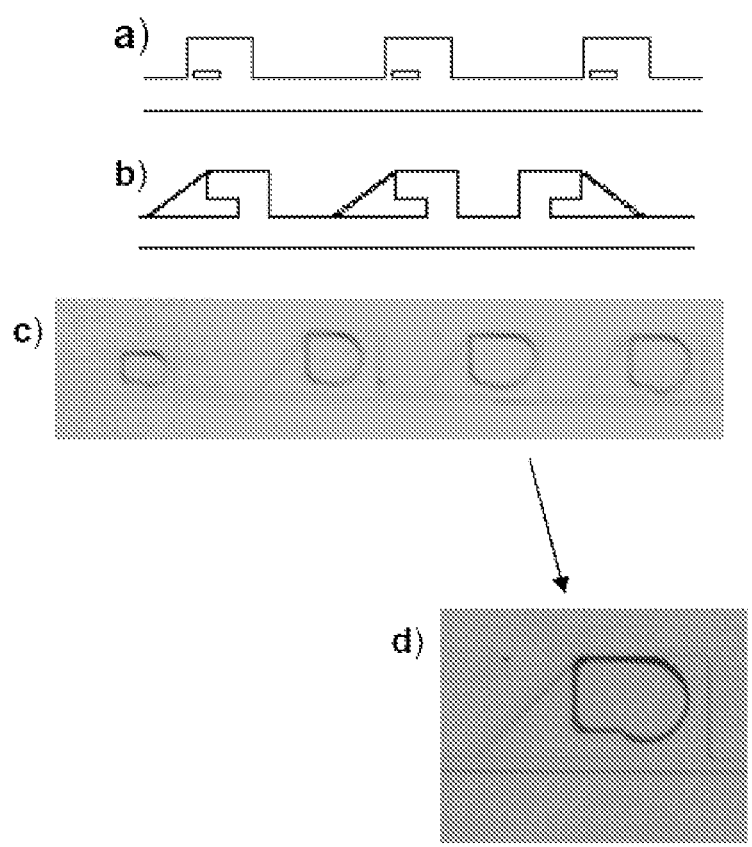
FIG. 14. Discretization chambers can also be made with drain channels which lead back to the main channel. These drain channels can be used to facilitate sample filling. a, b) Some examples of sample compartments with drain channels. The drain channels may be the same height or a different height than the main channel. e, d) Discretized samples that have been formed in a device that contains drain channels.

Example 9: Generation of Packets in Fluidic Harbors Multiply—Connected to a Flow Channel Discretization chambers can also be equipped with drain channels that lead back to the main channel, or to an auxiliary channel. These drain channels can be used to facilitate sample filling or sample removal. FIGS. 14(a and b) show some examples of sample compartments with drain channels. The drain channels may be the same height or a different height than the main channel. FIGS. 14(c and d) are images of discretized samples that have been formed in a device that contains drain channels.

Figure 14A:
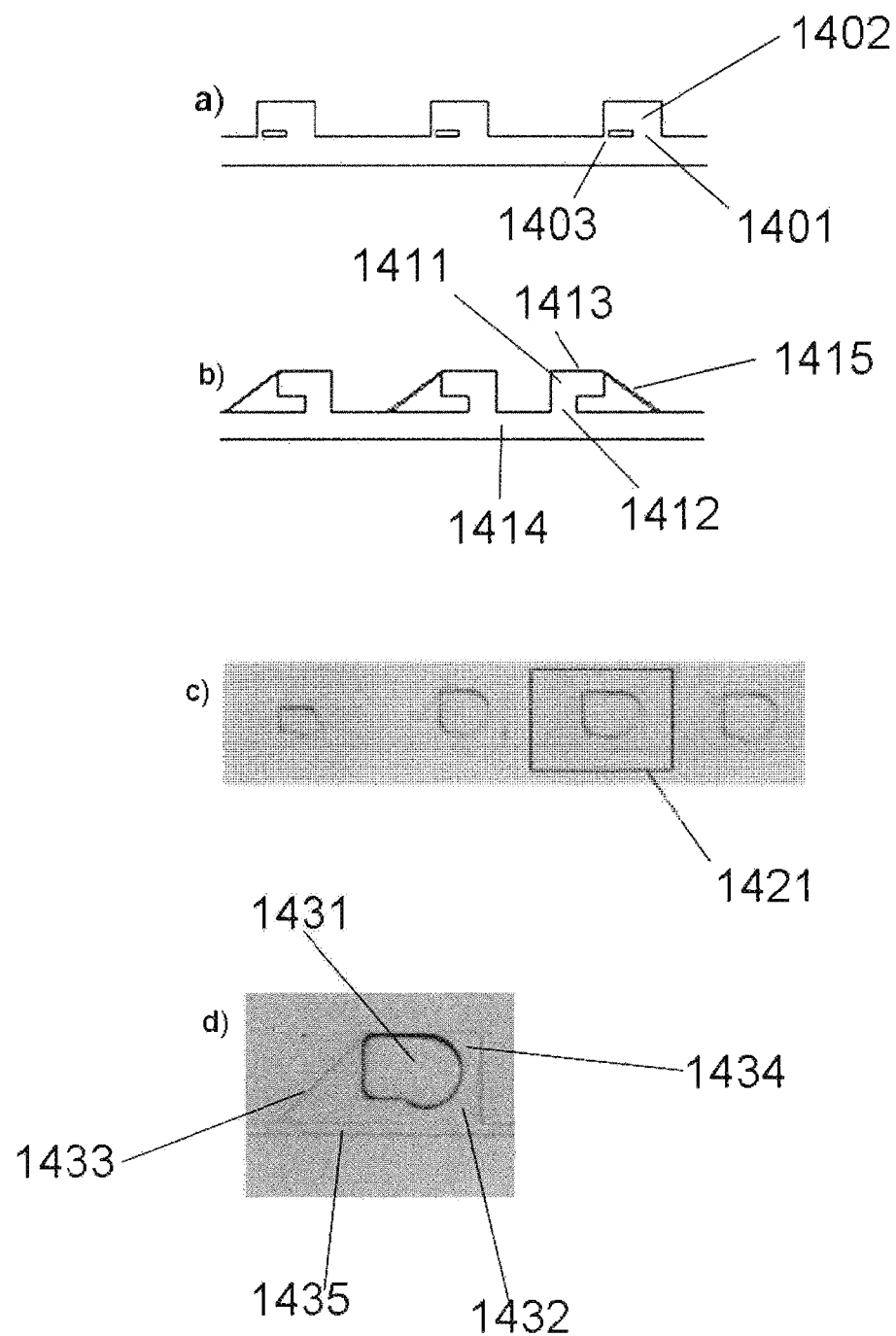
FIG. 14A. Examples of a fluidic harbor connecting to a main flow channel at more than one location.

In certain embodiments, a fluidic harbor may connect to a flow channel at more than one location. For example, as shown in FIG. 14A, a fluidic harbor 1402 (or 1411) may feature a "drainage" channel 1403 (or 1415) that leads back to the main flow channel in order to facilitate generation or removal of fluidic packets in fluidic harbors. Although FIG. 14A illustrates fluidic harbors with only two connections (e.g. 1401 and 1403 in FIG. 14A(a) and 1412 and 1415 in FIG. 14A(b) to the main flow channel, it is contemplated that fluidic harbors may have any number of connections to the main flow channel. It is also contemplated that fluidic harbors may have any number of drainage channels connecting to the main flow channel.

The drainage channels connecting to fluidic harbors may be of the same height or a different height than the main flow channel. FIG. 14A(a and b) show some examples of fluidic harbors with drainage channels. FIG. 14A (c and d) are images of fluidic packets that have been generated in fluidic harbors with drainage channels.

Example 10: Arrangement of Fluidic Harbors

Figure 15:
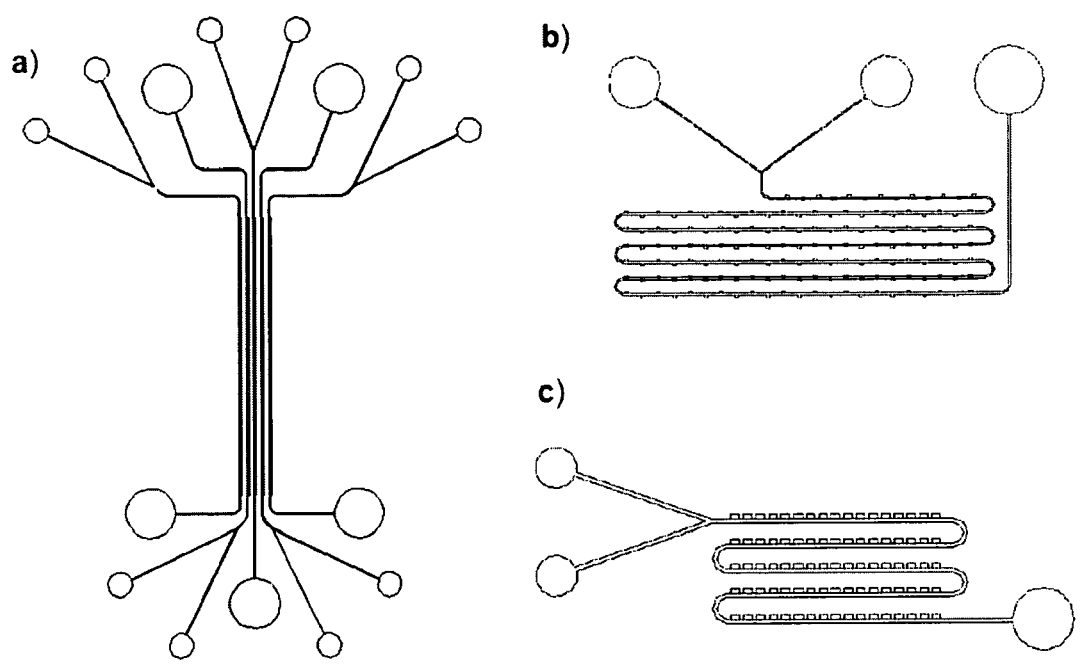
FIG. 15. Examples of device geometries which can be used to achieve a large array of discretized samples. a) Five parallel main channels that can be filled sequentially or in parallel. b) A single main channel folded in a serpentine fashion with alternating sample compartments. c) An additional example of a serpentine main channel with closely spaced adjacent sample compartments. The number and spacing of discretized samples can be predetermined to suit a specific application.
Figure 15A:
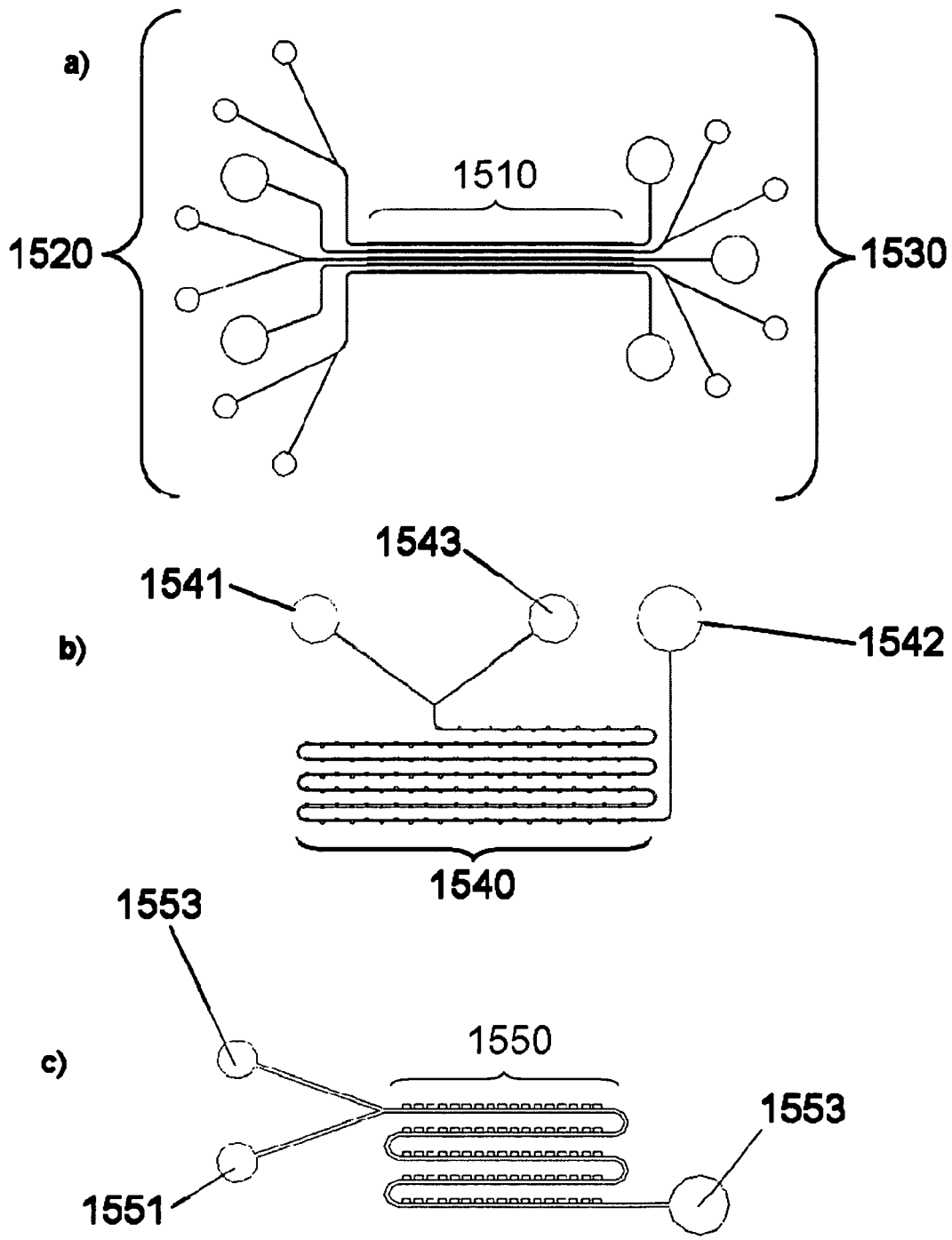
FIG. 15A. Examples of fluidic lattice configurations.

There are different approaches to creating a large array of discretized samples using our device. Examples of device geometries which can be used to achieve a large array of discretized samples are shown in FIG. 15. In FIG. 15(a), five parallel main channels have been arranged side by side. In many parallel biological assays, the number of parallel channels might be up to hundreds and potentially thousands. These devices can be sequentially filled or simultaneously filled. An alternative shown in FIG. 15(b) has a single main channel folded in a serpentine fashion with alternating sample compartments. An additional example of a serpentine main channel with closely spaced adjacent sample compartments is displayed in FIG. 15(c). The number and spacing of discretized samples is flexible and can be adjusted to suit a specific application.

In certain embodiments, multiple flow channels with fluidic harbors may be incorporated in a fluidic lattice. As illustrated in FIG. 15A(a), five parallel main flow channels have been arranged side-by-side, hosting hundreds to thousands of fluidic harbors. These flow channels may be sequentially filled (one flow channels at a time) or simultaneously filled (all channels at the same time).

In certain embodiments, the fluidic harbors may be located on more than one side of the main flow channel. As illustrated in FIG. 15A(b), fluidic harbors were created on two sides of a main flow channel (serpentine with six U-turns) in an alternating motif. In another embodiment, the fluidic harbors may form a two-dimensional array on the floor or ceiling of a very wide channel.

In another embodiment, the fluidic harbors may be created on only one side of the main flow channel. FIG. 15A(c) illustrates fluidic harbors on only one side of the main flow channel (serpentine with four U-turns).

Sample Manipulation

Example 11: Mixing Contents of Fluidic Harbors

Upon discretization of the samples, various manipulation techniques can be implemented for assays and reactions to be undertaken and monitored.

Mixing of Chambers in 2D and 3D

Figure 16:
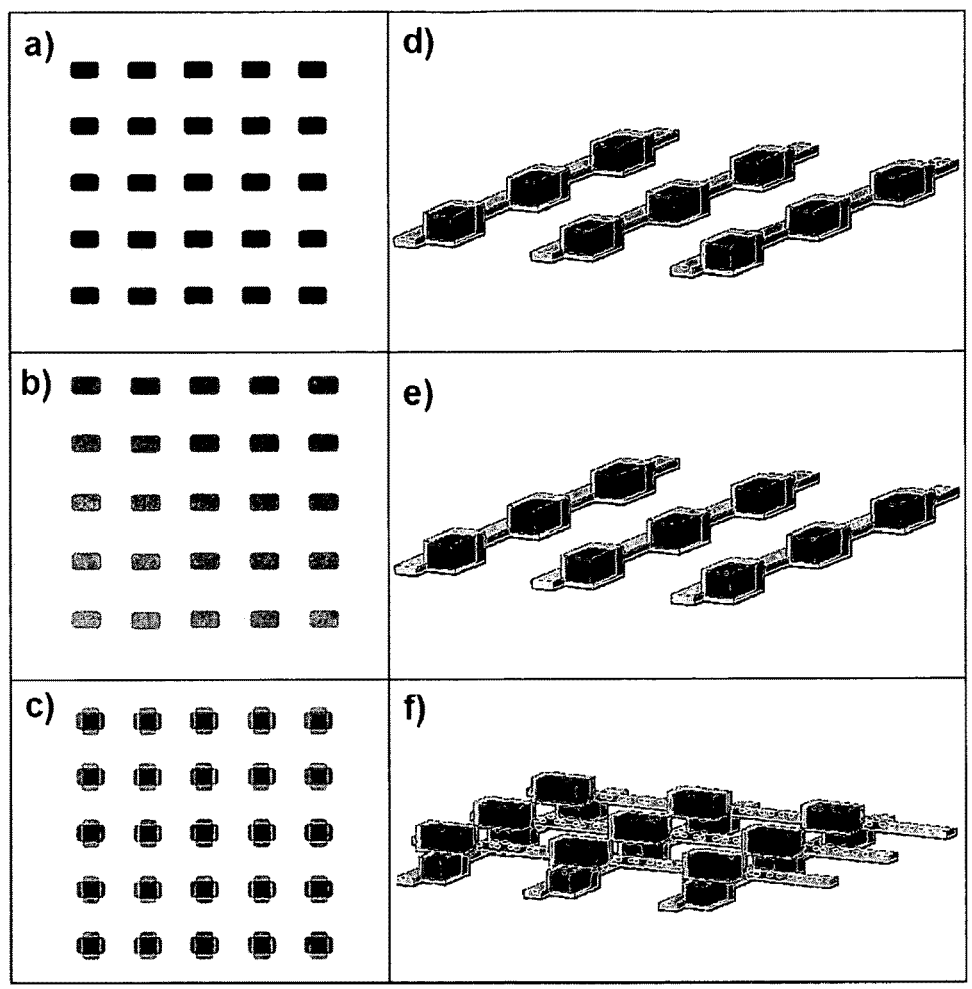
FIG. 16. Multilayer structure for assays using 2 compartment systems. a-b) shows filled compartment matrices for 2 different samples. c) shows the layered combination of (a) and (b) with perpendicular connections between the two sets of chambers or sample volumes so the top and bottom sample volumes can mix. d-f are representations of (a-c) respectively. The membrane separating the 2 layers in (f) has been removed for clarity. This thin membrane can form the roof or floor of the chamber and may be removed using a number of different methods to introduce connections between the two sets of top and bottom chambers and thus cause the two different sample volumes to mix.
Figure 17:
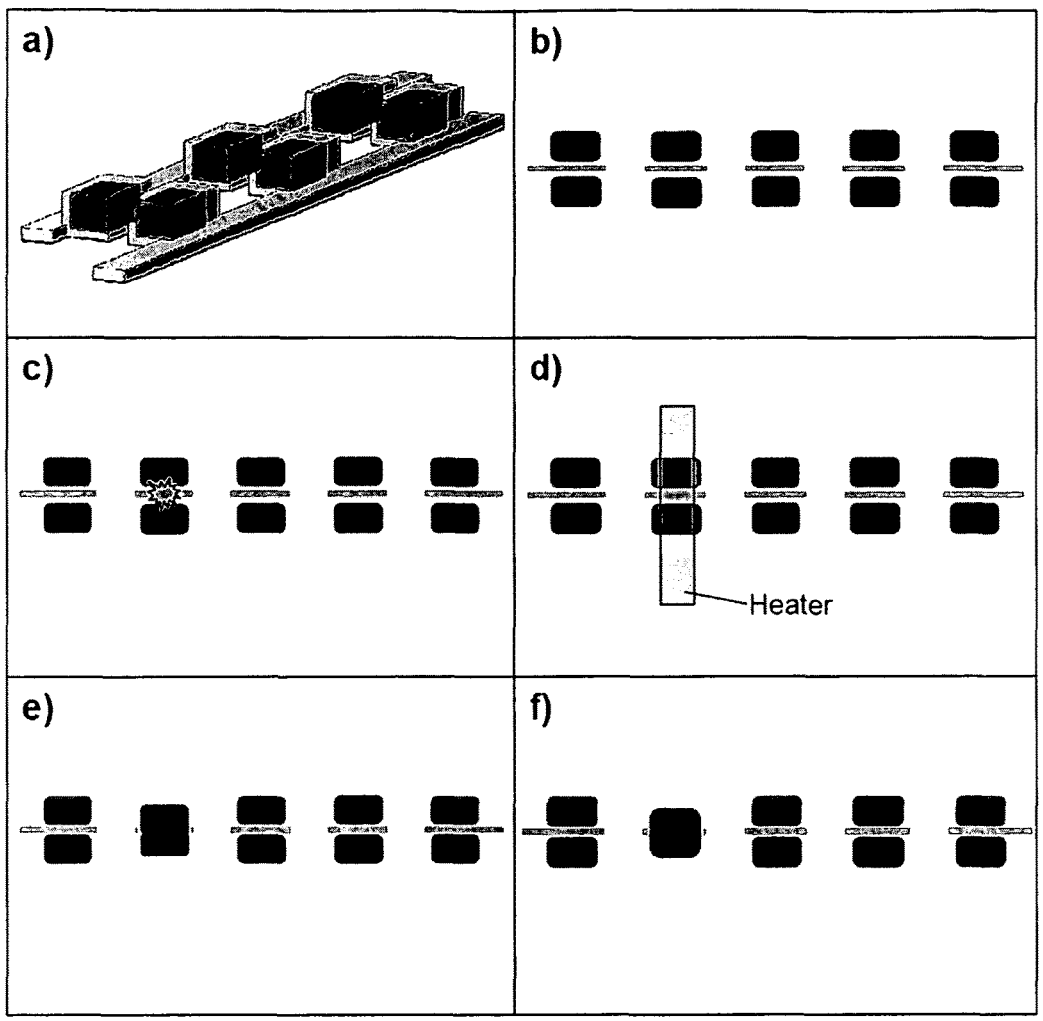
FIG. 17. Planar structure for addressable assays using 2 compartment systems. a) 3D image of filled sample compartments, where the different samples are separated by a thin membrane (membrane omitted for clarity); the thin membrane can form one of the walls of the chamber or may be the only material that forms the wall that separate the two chambers. b) 2D image of filled compartments with a thin membrane separating the compartments. c) Optical membrane disruption between compartments. d) Thermal membrane disruption between compartments, through heaters, external or patterned. e) Membrane breaks and 2 compartments mix fusing droplets or discretized sample volumes. f) Resulting fused or mixed sample.
Figure 18:
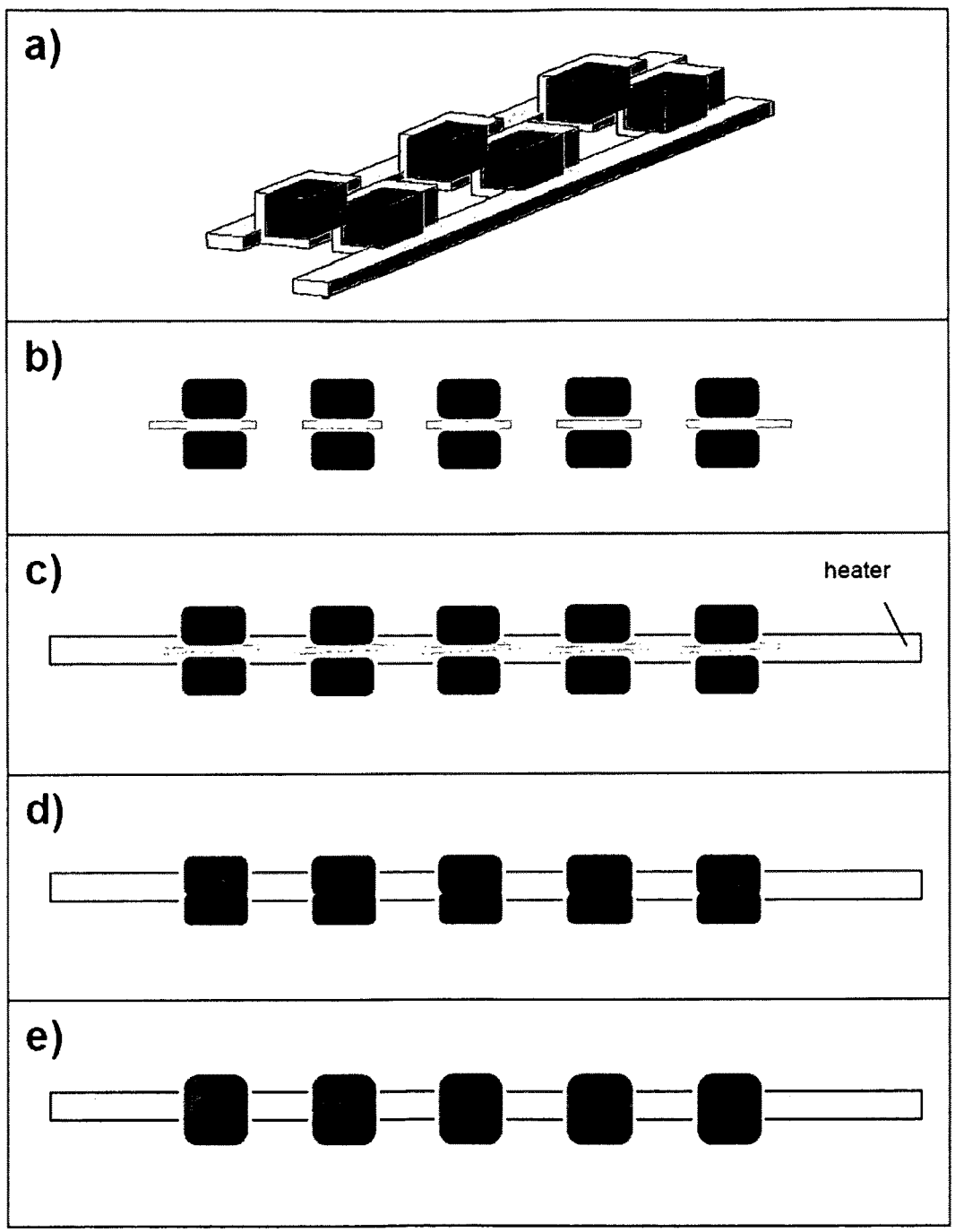
FIG. 18. Planar structure for large area assays using 2 compartment systems. a) 3D image of filled compartments, where the different samples are separated by a thin membrane (membrane omitted for clarity); the thin membrane can form one of the walls of the chamber or may be the only material that forms the wall that separate the two chambers. b) 2D image of filled compartments with a thin membrane separating the compartments, where the thin membrane may be the only material that forms the wall between the two chambers. c) Thermal membrane disruption between compartments, through heaters, external or patterned. d) Membrane breaks and opposite compartments mix fusing or mixing samples. e) Resulting fused or mixed sample array.

Due to the versatility of the design and ease of fabrication, the discretization scheme can be implemented in both 2D and 3D arrays. To cause mixing between different sample volumes, a 2D array positions sample volumes with differing contents adjacent to each other (see FIGS. 17 and 18) such that break down of the partition (wall) that separates the two sample volumes (chambers) results in fusing and mixing of the two sample volumes that were previously contained in two separate chambers. In a 3D array (FIG. 16f, the different sample volumes are stacked on top or below each other, such that break down of the floor or roof that separates the two top-and-bottom chambers results in fusing and mixing of the contents of the two different sampling volumes. An example implementation of each can be seen in FIG. 16 (3D) and FIGS. 17 & 18 (2D).

Figure 17A:
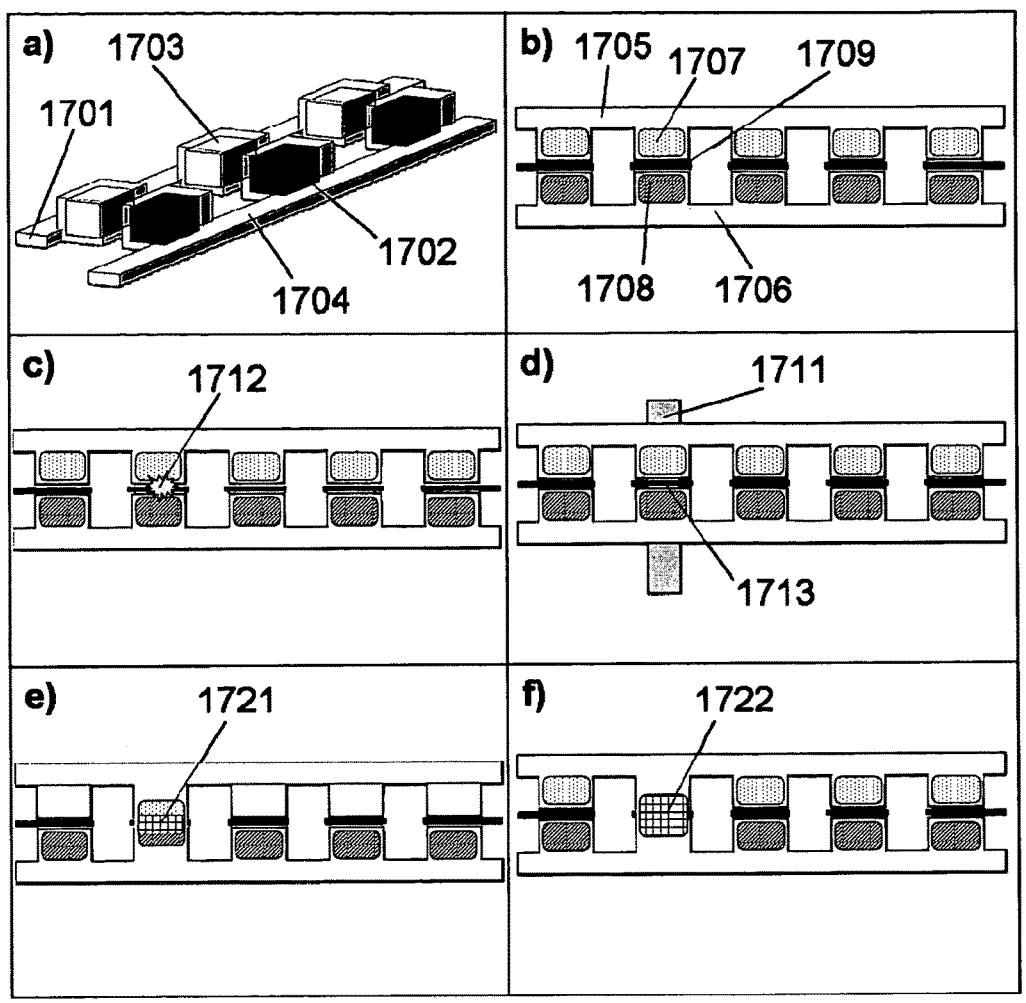
FIG. 17A. Planar design of fluidic lattices with adjacent fluidic harbors separated by an individually removable membrane.
Figure 18A:
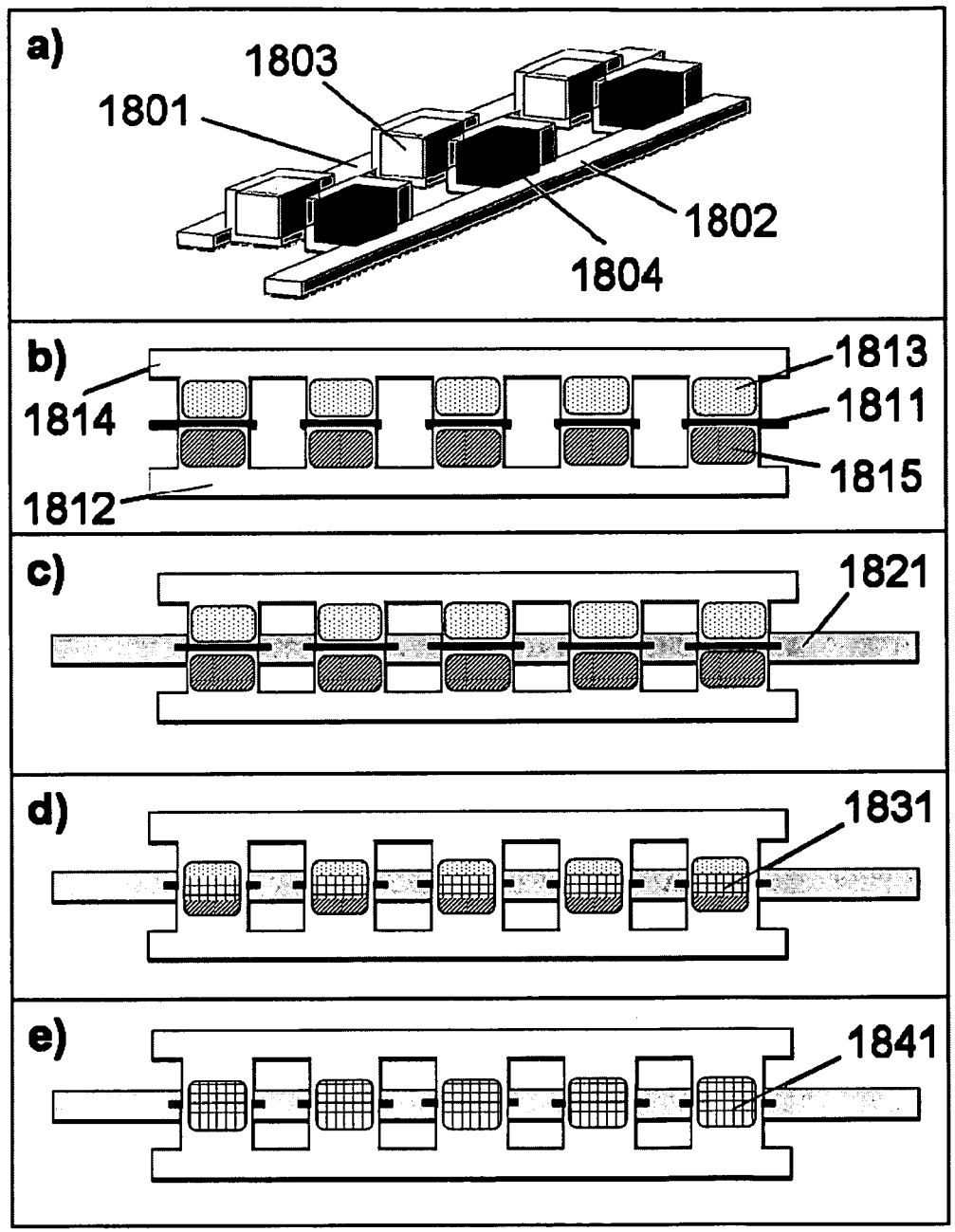
FIG. 18A. Planar design of fluidic lattices with adjacent fluidic harbors separated by a removable membrane.

In certain embodiments, a fluidic harbor may be adjacent to one or more fluidic harbor(s), separated by one or more removable wall(s). Upon destruction of the removable wall, the contents of the fluidic harbors can co-mingle. FIGS. 17A and 18A illustrate two-dimensional arrangements of fluidic harbors where two adjacent harbors on the same horizontal plane are separated by a removable wall. Upon breaking down the wall, the fluidic packets fuse and mix.

Figure 16A:
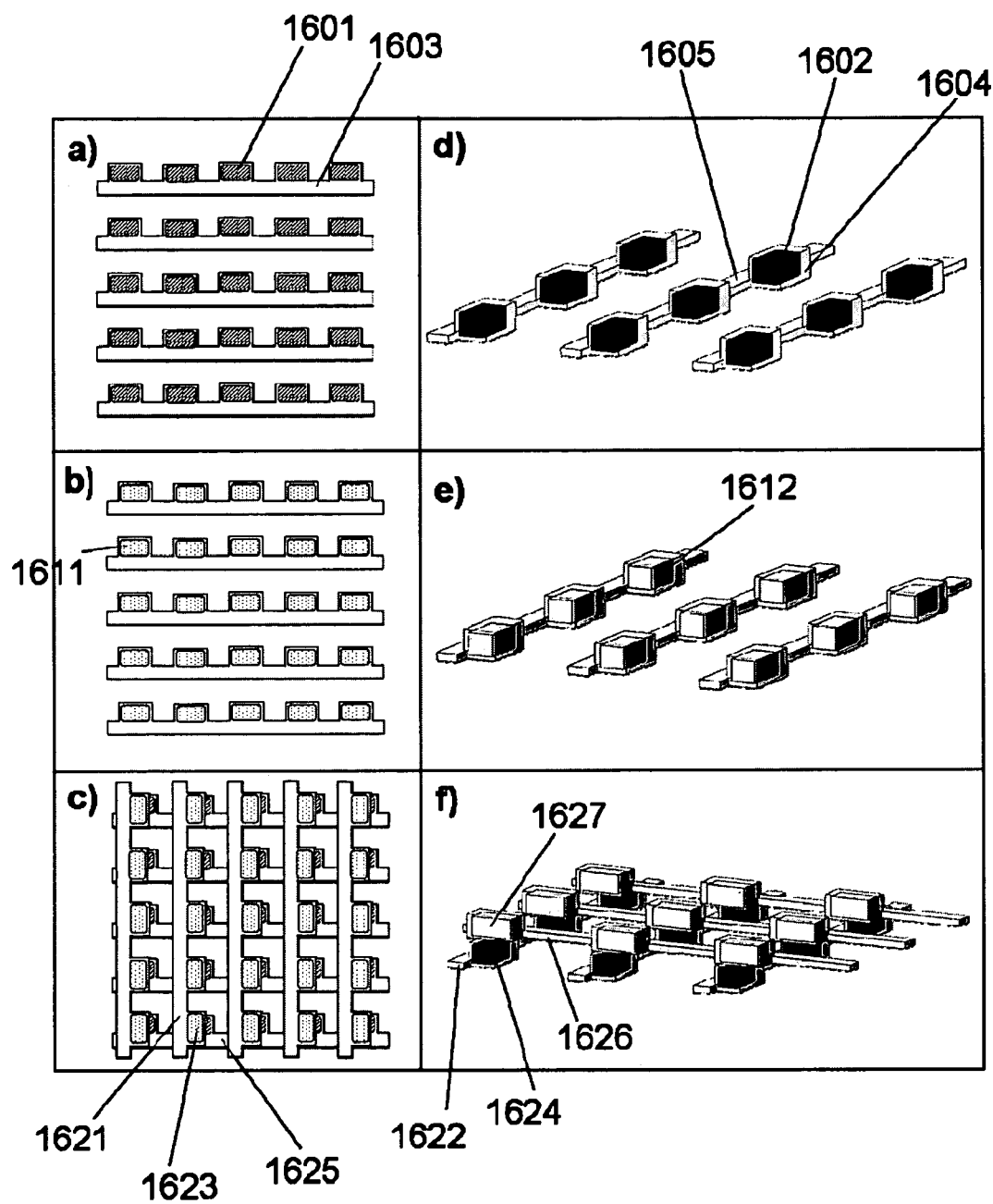
FIG. 16A. Multilayer design of a fluidic lattice with adjacent fluidic harbors separated by a removable membrane.

In one embodiment, a fluidic harbor may be layered above one or more fluidic harbor(s), separated by one or more removable wall(s). For example, FIG. 16A(f) shows a three-dimensional arrangement of fluidic harbors where fluidic harbors located on two horizontal planes are layered one on top of the other, each pair of adjacent harbors separated by a removable wall.

The 3D layered design requires that the sample chambers be aligned on top of each other. Two Layers are shown but this can be multiplexed for more layers. In either 3D or 2D arrays of sample chambers, the chambers whose contents are to be mixed with each other are spatially isolated within the chamber by a thin membrane or substrate such that the sample volumes of the adjacent chambers do not mix until the thin membrane or substrate is broken down or removed.

Removable walls or membranes separating adjacent fluidic harbors can be fabricated from any material that is degradable using any of the following approaches: photo-induced/light-induced (FIG. 17A(c), disrupting membrane 1712), thermally-induced (FIG. 17A(d), strip heater 1711 disrupting membrane 1713), solvent-induced, electric-field induced, magnetic-field induced, chemical-induced, mechanically-induced, pneumatically-induced, dissolution-induced, or combinations thereof.

This thin membrane can be fabricated from any degradable (by either photo-induced/light-induced, thermally-induced, solvent-induced, electric-field induced, magnetic-field induced, or combinations thereof) material that will partition into the immiscible phase or continuous phase (or both) either as fragments or as a dissolved substance. It is preferable that the materials from the thin membrane do not dissolve into the aqueous phase so as to avoid interference with the assays carried out in the aqueous phase. The membrane can also be made of a material which has some solubility in the continuous phase making it a temporary membrane which will dissolve at a predefined time or upon exchange of the immiscible phase (replace one type of immiscible phase with another) once the sampling volume has been discretized within the chamber. For example, the membrane might not dissolve in silicone oil but dissolves in perfluoro-solvents, in which the discretization process might be carried out in silicone oil and the dissolution of the membrane might be carried out using a perfluorosolvent; here, neither silicone oil nor perfluoro-solvent is miscible with aqueous solution.

In certain embodiments, removable walls or membranes are constructed out of materials that preferentially dissolve in one of the continuous fluids. It may be desirable that debris of removable walls do not dissolve into an analyte-containing fluid so as to avoid interference with analytes of interest.

The destruction or removal of this thin membrane or substrate can be based on a range of mechanism, including but not limited to, laser ablation, laser heating, light-induced membrane breakdown, light-induced molecular conformational changes, light-induced changes in solubility of membrane in immiscible phase or aqueous phase, the use of patterned heating pads for thermally induced removal of membrane, electric-field induced removal of the membrane, electrolysis, dielectric breakdown of the membrane, electroporation of the membrane, solvent induced removal of the membrane, magnetic field induced removal of the membrane, ultrasound induced removal of the membrane, catalyst or chemical induced removal of the membrane, pH induced removal of the membrane, or some combinations thereof.

In some embodiments, the walls separating adjacent fluidic harbors can be removed by any of the following techniques: laser ablation; laser heating; light-induced membrane breakdown; light-induced molecular conformational changes; light-induced changes in solubility of membrane in immiscible organic phase or aqueous phase; thermally induced removal of membrane through patterned heating pads; electric-field induced removal of the membrane; electrolysis; dielectric breakdown of the membrane; electroporation of the membrane; solvent-induced removal of the membrane; magnetic field-induced removal of the membrane; ultrasound-induced removal of the membrane; catalyst- or chemical-induced removal of the membrane; pH-induced removal of the membrane; or combinations thereof.

In one embodiment, the walls separating adjacent fluidic harbors are individually removed.

The 2D design is simpler in construction requiring only a membrane layer to be sandwiched between adjacent chambers. An example construction of which can be seen in FIGS. 17 and 18, highlighting the individual addressability or complete row addressability of the design. In FIG. 17(a), a 3D representation of the channels is given along with a pictographic image in 17(b) of filled channels, where the different samples are separated by a thin membrane. In FIG. 17(a) the separating membrane was omitted for clarity of compartmentalization images. As with the 3D design the membrane can be disrupted using various methodologies as described above.

In certain embodiments, multiple walls separating adjacent fluidic harbors are simultaneously removed. For example, it is possible that an entire region of fluidic lattice containing multiple adjacent fluidic harbors can be addressed simultaneously and that all walls separating adjacent harbors can be simultaneously removed, FIG. 18A shows an example of five pairs of adjacent fluidic harbors, each pair separated by a removable wall 1811. A strip of heating element 1821 traverses all five pairs of harbors and removes the five walls simultaneously, leading to five sets of mixing of fluidic packet contents executed in parallel.

As well as the individual addressing of the assays or chambers, it is possible to use the same disruption protocol to address entire chip sections or rows or select portions of the chip, allowing for many sample assays or reactions (which may be of the same type or different type) to be made in the chip. An example implementation of this can be seen in FIG. 18, where a patterned heating element was used to break a line of membranes, fusing a row of chambers.

Maintaining Sample Conditions by Using Auxiliary Channels and Use of Discretized Samples for PCR Example 12: Presence of Auxiliary Channels to Stabilize Fluidic Packets in Fluidic Harbors In certain embodiments, fluidic packets generated in fluidic harbors are stabilized with a matter delivered by an auxiliary flow channel.

As an example, a fluidic packet containing an aqueous solution of genetic materials was generated in a fluidic harbor, and was subjected to a heating step during a polymerase chain reaction (PCR). The fluidic lattice was constructed from polydimethylsiloxane (PDMS), a gas-permeable material. As the fluidic packet was heated, water evaporated and escaped from the harbors, leading to an uncontrolled variation in analyte concentration. Two auxiliary channels (e.g. auxiliary channels 1902 and 1903 in FIG. 19A(a) and auxiliary channels 1922 and 1923 in FIG. 19A(c)), one on each side of the main flow channels, can be used to carry an aqueous solution at a specified flow rate to saturate PDMS with water, minimizing the evaporation or reduction in volume of fluidic packets while replenishing the aqueous content of fluidic packet through diffusion.

Figure 19:
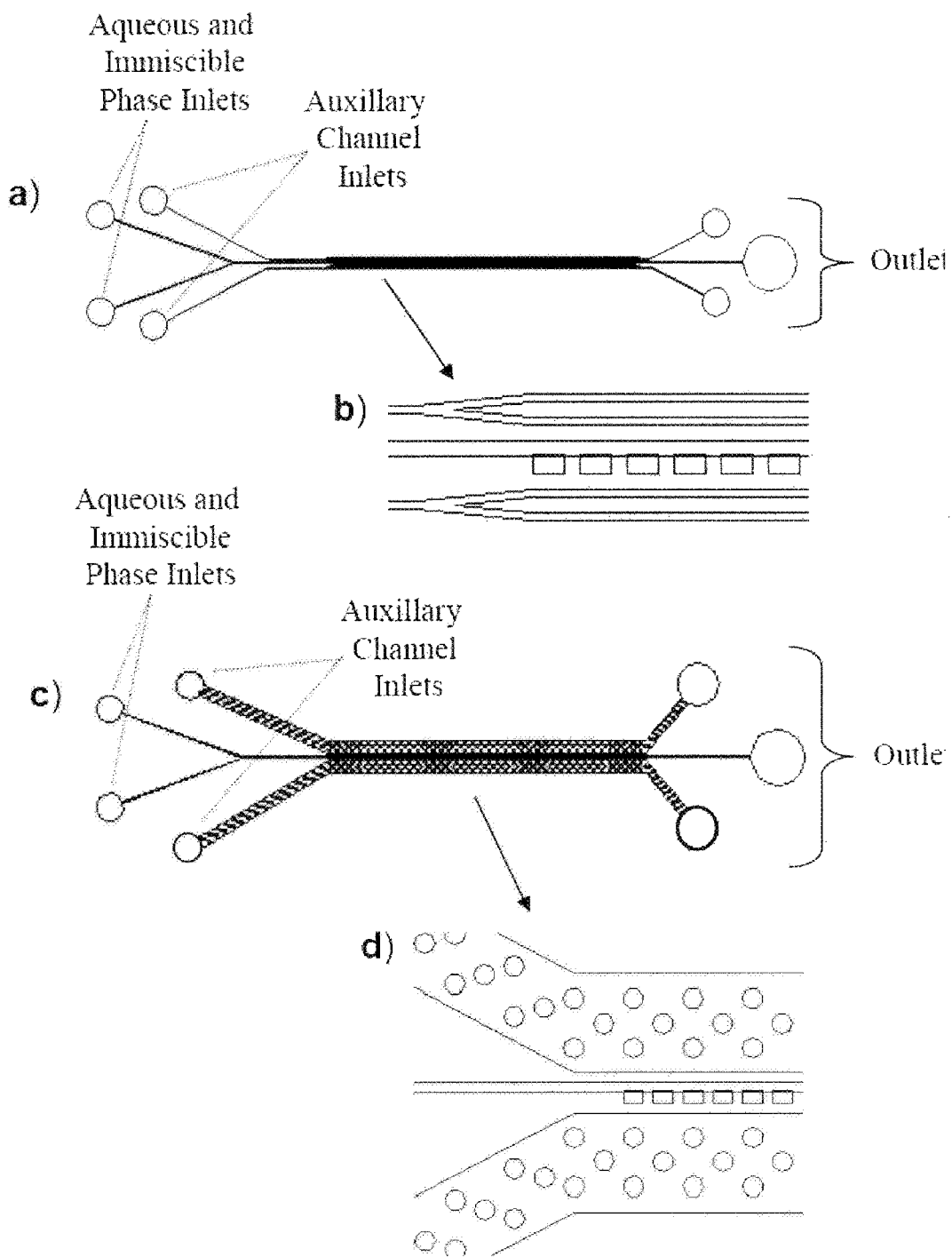
FIG. 19. Examples of auxiliary channel schematics. Auxiliary channels can be used to saturate gas permeable polymer chips and/or immiscible phase with water in order to inhibit volume loss when heating an aqueous discretized sample, such as during PCR. a) An example of a discretization device with integrated auxiliary channels on either side of the discretization region. In this example, there are two auxiliary channels on either side of the main channel. b) A magnified view of the auxiliary channels and the discretization region of the device described in a). c) An example of a discretization device with a single auxiliary channel on either side of the main channel. d) A magnified view of the auxiliary channels and discretization region of the device described in c).
Figure 19A:
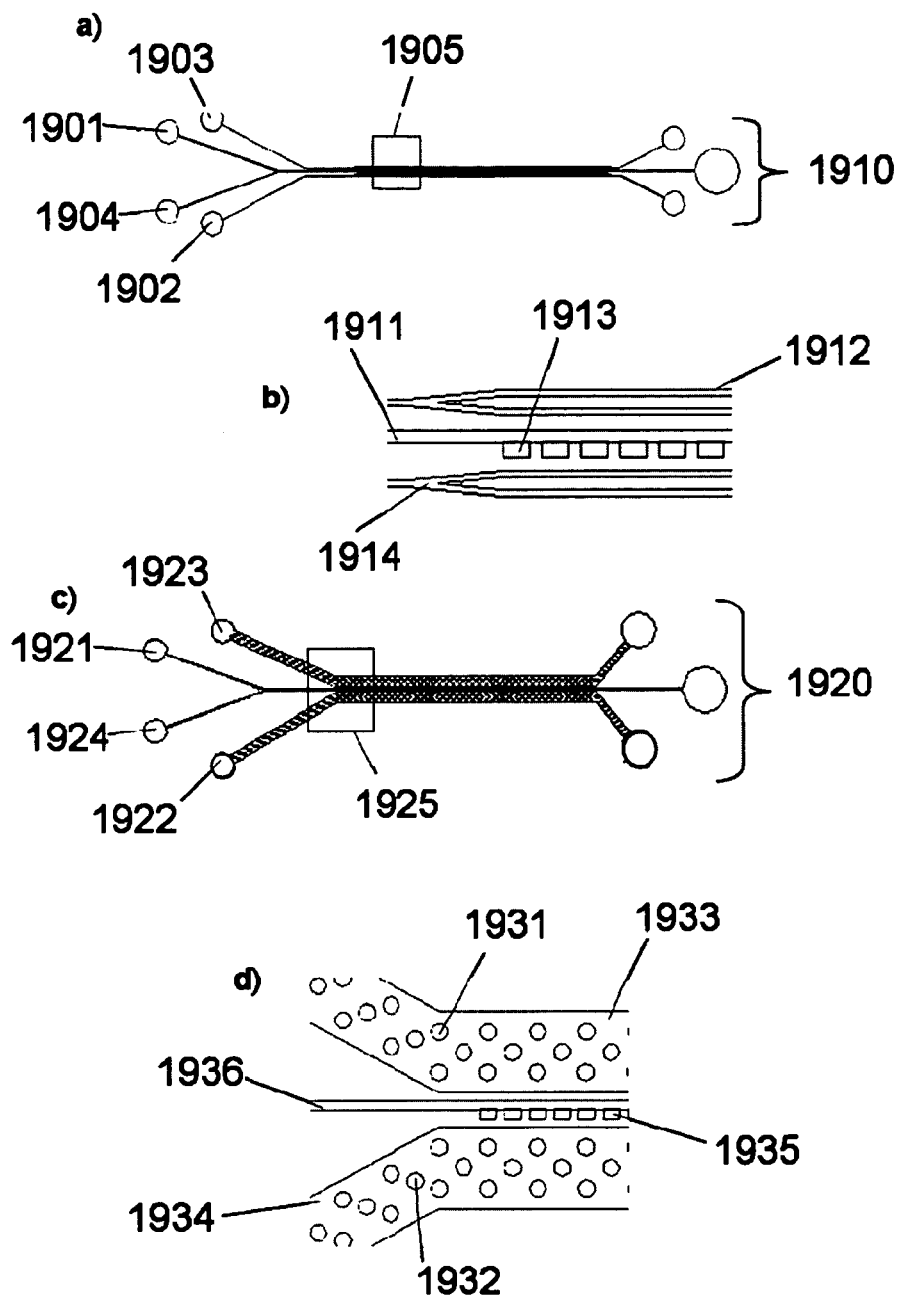
FIG. 19A. Examples of auxiliary channel schematics.
Figure 20:
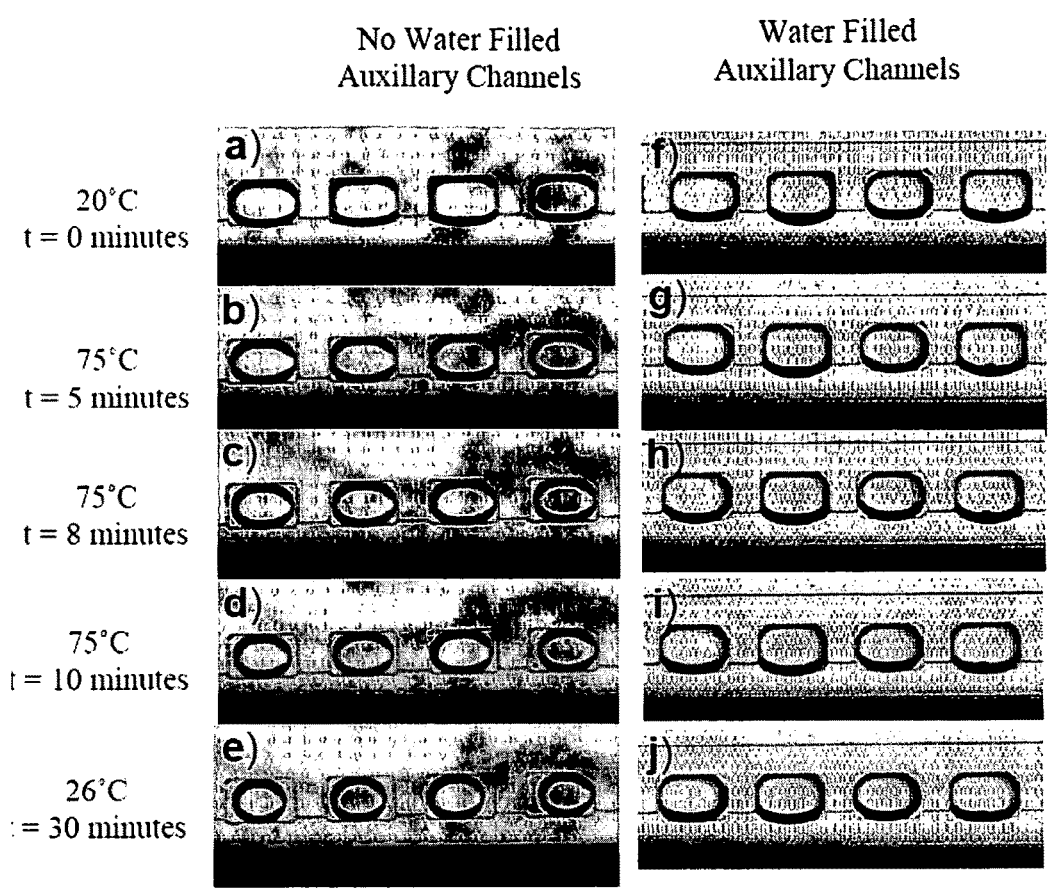
FIG. 20. Images of aqueous discretized samples that have been heated in a device without water filled auxiliary channels (a-e) and with water filled auxiliary channels (f-j). The sample phase in the images is 10 mM Tris HCl, 50 mM KCl and 1.5 mM MgCl2. The immiscible phase is light mineral oil with 0.01% Span 80.
Figure 20A:
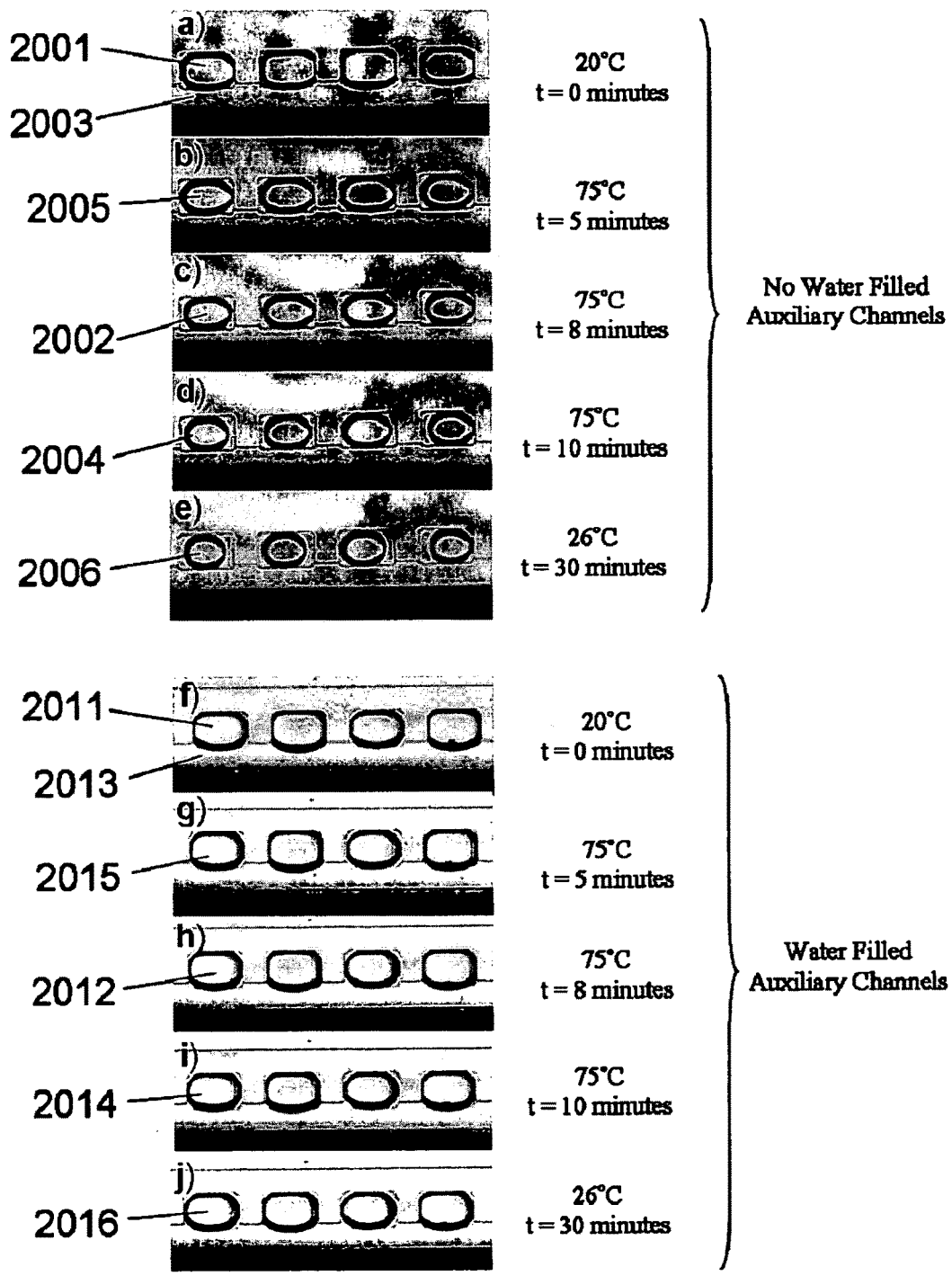
FIG. 20A. Images of fluidic packets that have been heated without water filled auxiliary channels (a-e) and with water filled auxiliary channels (f-j).

FIG. 20A contains images of fluidic packets that have been heated in the absence of (FIG. 20A(a-e)) and in the presence of (FIG. 20A (f-j)) auxiliary channels filled with flowing water. When heated in presence of auxiliary channels as depicted in FIG. 19A, packet volume loss was avoided or minimized. The fluidic packet in FIG. 20A comprises an aqueous solution of 10 mM Tris HCl, 50 mM KCl and 1.5 mM $MgCl_2$. The other continuous fluid was a light mineral oil with 0.01% Span 80. The presence of the auxiliary channels allow for retention of the packet volume, and hence can stabilize the concentration of packet components during heating for a PCR experiment.

In certain embodiments, an auxiliary channel not in fluidic communication with a fluidic harbor is located near the fluidic harbor to stabilize the contents of the fluidic harbor. In some embodiments, an auxiliary channel carries a diffusible component to infuse a constituent of a fluidic packet in a fluidic harbor. In certain embodiments, an auxiliary channel carries a component to inhibit the escape of a constituent of a fluidic packet in a fluidic harbor.

In some embodiments, fluidic packets generated in fluidic harbors are stabilized with an energy delivered or removed by an auxiliary channel. As an example, an auxiliary channel may carry a heated fluid to raise the temperature of a fluidic packet by conduction. Alternatively, an auxiliary channel may carry a cooled fluid to lower the temperature of a fluidic packet by conduction. Accurate temperature control of a fluidic packet may be necessary to optimize reaction rates for PCR.

Embodiments of devices according to the present invention are able to separate the processes of discretization and manipulation. This is in part due to the layout and construction, as well as the stability of the samples within the compartments on the chip. This is further aided by the ability to maintain optimum sample conditions through the use of auxiliary control channels. For example, for some applications, such as polymerase chain reaction (PCR), it may be necessary to heat discretized samples. If the device is constructed from a gas permeable material, such as PDMS, complications with sample evaporation during heating may occur. Auxiliary channels located close to the sample compartments can be used to saturate gas permeable polymer chips or the immiscible phase with water in order to inhibit volume loss when heating an aqueous discretized sample. These auxiliary channels may be integrated in a manner that is best suited for the particular application. FIG. 19 provides some examples of auxiliary channel schematics. In FIG. 19(a), there is a version of a discretization device with integrated auxiliary channels on either side of the discretization region. In this example, there are two thin auxiliary channels on either side of the main channel. In an alternative configuration there may be one large auxiliary channel on either side of the main channel (FIG. 19(c). FIG. 20 contains images of sample volumes that have been heated in the absence of (FIG. 20(a-e)) and in the presence of (FIG. 20(f-j)) auxiliary channels filled with water. When heated in a discretization device containing aqueous auxiliary channels, sample volume loss is avoided or minimized. The sample phase in the images is 10 mM Tris HCl, 50 mM KCl and 1.5 mM $MgCl_2$. The immiscible phase is light mineral oil with 0.01% Span 80. It is clear to see that the presence of the auxiliary channels allows for retention of the sample volume, hence concentration, during a heating and cooling cycle of a PCR experiment.

In general, these auxiliary channels, which often are located close to the sample chambers and discretization region, allow for infusion and maintenance of any material that may be partially soluble in the substrate or in the immiscible phase to be saturated prior to or during the experiment. The auxiliary channels also allow for other local environmental parameters (e.g. temperature) of the chambers to be actively controlled. For example, due to the small size scale, the thermal diffusivity of the chip is very fast, allowing for a rapid equilibrium to be established once a change has been made. This allows the auxiliary channels to act as real-time environmental control for the compartmentalized volumes.

Transport of the Discretized Samples Out of the Compartments

Example 13: Releasing Fluidic Packets from Fluidic Harbors

In certain embodiments, fluidic packets can be released from the fluidic harbors that were used to form them.

After fluidic packets are generated in fluidic harbors, it is often desirable to remove the entire, or a portion, of a fluidic packet from a fluidic harbor for further analysis, processing, or monitoring.

Post discretization of the compartmentalized sample, it is often desirable to remove some or all of the samples for further analysis or monitoring. This can be done in a drop-wise fashion (removing portions of the compartmentalized sample at a time), or a complete removal of the volume using fluidic displacement, or using interfacial tension modification to allow the sample to deform easier in flow. Below, we will describe some methods to achieve this removal of compartmentalized samples.

Extraction of the Compartmentalized Sample by Varying Flow Rate

Figure 21:
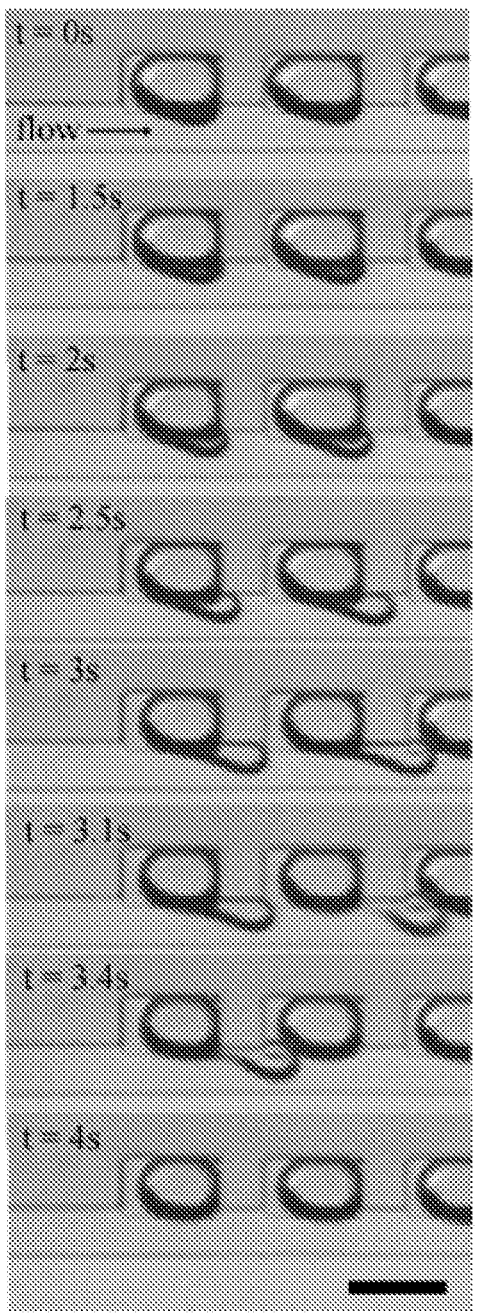
FIG. 21. Discretized samples can be released from the sample compartments by flowing immiscible phase through the device at an elevated flow rate. In these images, the sample phase is 1 nM phosphate buffer and the immiscible phase is light mineral oil with 0.01% Span 80. The flow rate of the immiscible phase was 3 μL per minute. The scale bar corresponds to 200 μm.

One extraction or sample-volume-removal method is by flowing immiscible phase through the device at an elevated flow rate. An experiment of this method can be seen in FIG. 21. In this figure, the sample phase is 1 nM phosphate buffer and the immiscible phase is light mineral oil with 0.01% Span 80. To remove the sample from the compartments the flow rate of the immiscible phase was set to 3 µL per minute. The flow of the immiscible phase causes the discretized volume to escape the chamber. By varying the flow rate of the immiscible phase, the volume of the extracted droplet can be tuned, and complete removal of the sample volume can be achieved if desired.

In certain embodiments, fluidic packets can be released from fluidic harbors by changing a flow rate. In certain embodiments, fluidic packets can be released from fluidic harbors by flowing another continuous fluid into the fluidic lattice. In some embodiments, fluidic packets can be released from fluidic harbors by altering the interactions between fluids.

Figure 21A:
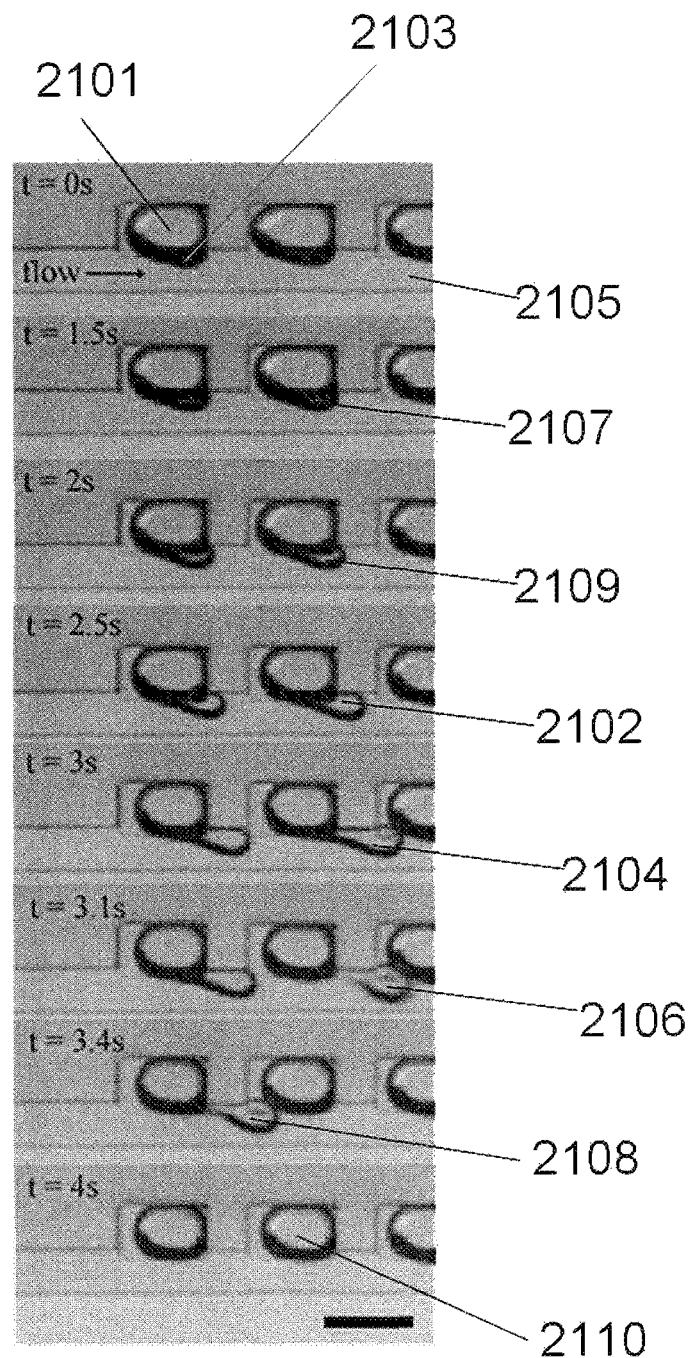
FIG. 21A. Example of fluidic packets partially released from fluidic harbors by changing a flow rate.

FIG. 21A shows an example of the partial release of fluidic packets from fluidic harbors by changing a flow rate. In FIG. 21A, the fluidic packet was 1 nM phosphate buffer and the other continuous fluid 2105 was light mineral oil with 0.01% Span 80. To remove a portion of a fluidic packet from the fluidic harbor that was used to form it, the flow rate of the light mineral oil was increased to 3 µL per minute (following fluidic packet generation). The flow of the light mineral oil caused portions of the fluidic packets to escape the harbors.

Extraction of the Compartmentalized Sample by Introduction of a Second Immiscible Phase The versatility of the chip design allows for integration of multiple dispersed and continuous phase inlet lines. An alternative method for the removal of sample volumes is to flow a second immiscible phase with a different viscosity and/or with a different density through the device. For example, by flowing a more viscous immiscible phase through the device, following sample discretization, it is possible to completely remove the sample from the compartments in an ordered fashion and transfer them to a different region for further analysis. This technique also allows for completely emptying the chip, recycling it for multiple use. When using the fill method that exploits the difference in buoyancy between the sample phase and immiscible phase, a second immiscible phase with a different density than that of the first immiscible phase will allow the discretized samples to be removed from the sample compartments.

Figure 22:
FIG. 22. Schematic of discretized samples being removed from the sample compartments by flowing a more viscous immiscible phase through the device. The flow of the higher viscosity immiscible phase causes the discretized volume to escape the chamber.
Figure 22:
Figure 22:
Figure 22:
Figure 22:
Figure 22A:
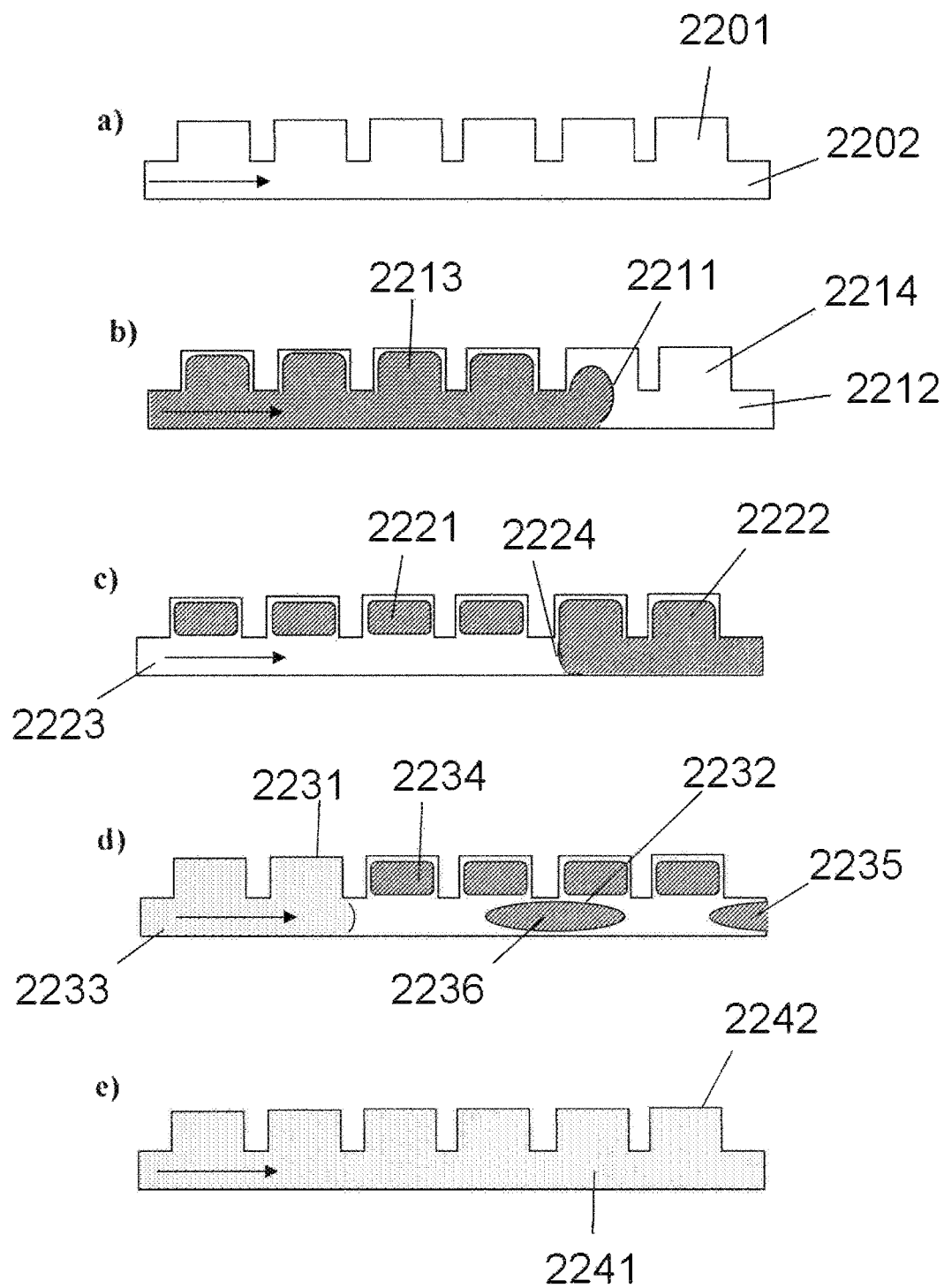
FIG. 22A. Example of fluidic packets completely released from fluidic harbors by flowing another continuous fluid into the fluidic lattice.

FIG. 22A shows an example of fluidic packets released from fluidic harbors by flowing another continuous fluid into the fluidic lattice. For example, after generating a fluidic packet in fluidic harbor, another continuous fluid of a higher viscosity can be flowed into the fluidic lattice, unsettling the fluidic packet. It is possible to completely remove the fluidic packets from the harbors in an orderly fashion and transfer the packets to a different region for further analysis. The ability to remove the fluidic packets from fluidic harbors also allows for the complete emptying of a fluidic lattice in order to recycle the lattice and use it to form different fluidic packets.

In an embodiment, the unsettling continuous fluid may be more viscous than a previous continuous fluid.

In an embodiment, the unsettling fluid may be lighter or less dense than a previous fluid. In an embodiment, the transposing fluid may be denser than a previous fluid.

Furthermore, sample extraction from the compartments can be further modulated through switching of the immiscible flow to one containing an elevated or decreased amount of surfactant or to one that simply contains a different surfactant. In this case, the second immiscible phase flow can either be of the same immiscible oil but with a different type or amount of surfactants or can be an entirely different immiscible oil containing the same amount or different amount or type of surfactants. Once this second immiscible phase with a different surfactant content has been flown through the chip, some surfactant will migrate to the boundary that separates the sample solution from immiscible phase, thus altering the interfacial tension and making the sample volumes more susceptible to interface deformation and easier to remove from the compartments.

In an embodiment, the unsettling continuous fluid may be similar or identical to a previous continuous fluid, but mixed with a different amount of surfactant. In another embodiment, the unsettling continuous fluid may be chemically different from a previous continuous fluid, but mixed with the same composition of surfactant. Both embodiments alter the interfacial tension of a fluidic packet, possibly causing the packet to be more susceptible to interfacial deformation and more easily expelled from the fluidic harbor that was used to generate the fluidic packet.

Figure 23:
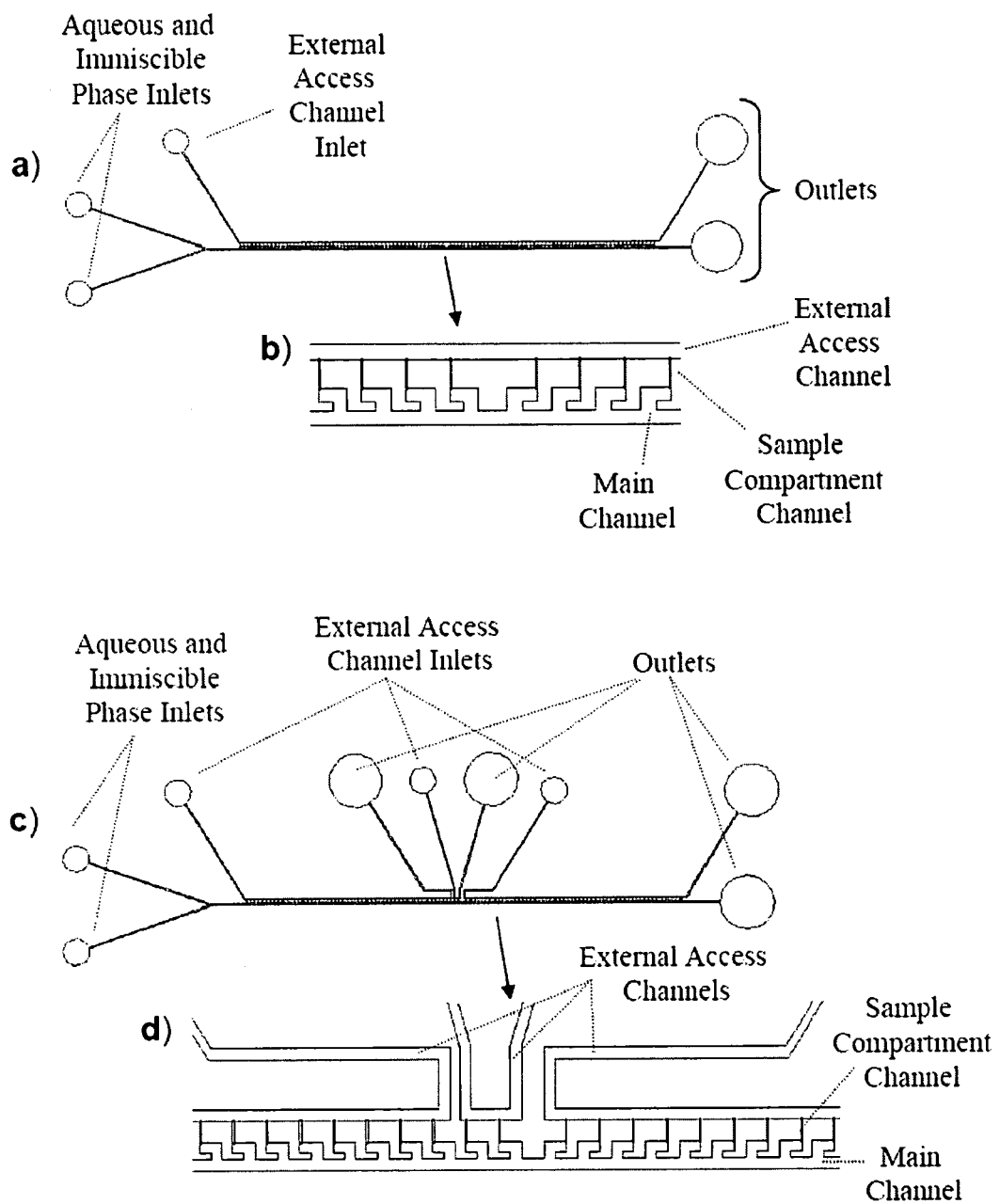
FIG. 23. External access channels can be integrated into the dicretization device to address and facilitate removal of selected discretized samples. The external access channels are connected to the sample compartment by a sample compartment channel. The dimensions of the external access channels and sample compartment channels may be optimized to suit a particular application. a) An example of a discretization device with an external access channel running parallel to the main channel. This external access channel connects to sample compartment channels that provide access to each sample compartment, b) An example of a discretization device with three external access channels used to independently address different sample compartments. These auxiliary sample access channels may be used with any of the previously detailed discretization geometries.
Figure 23A:
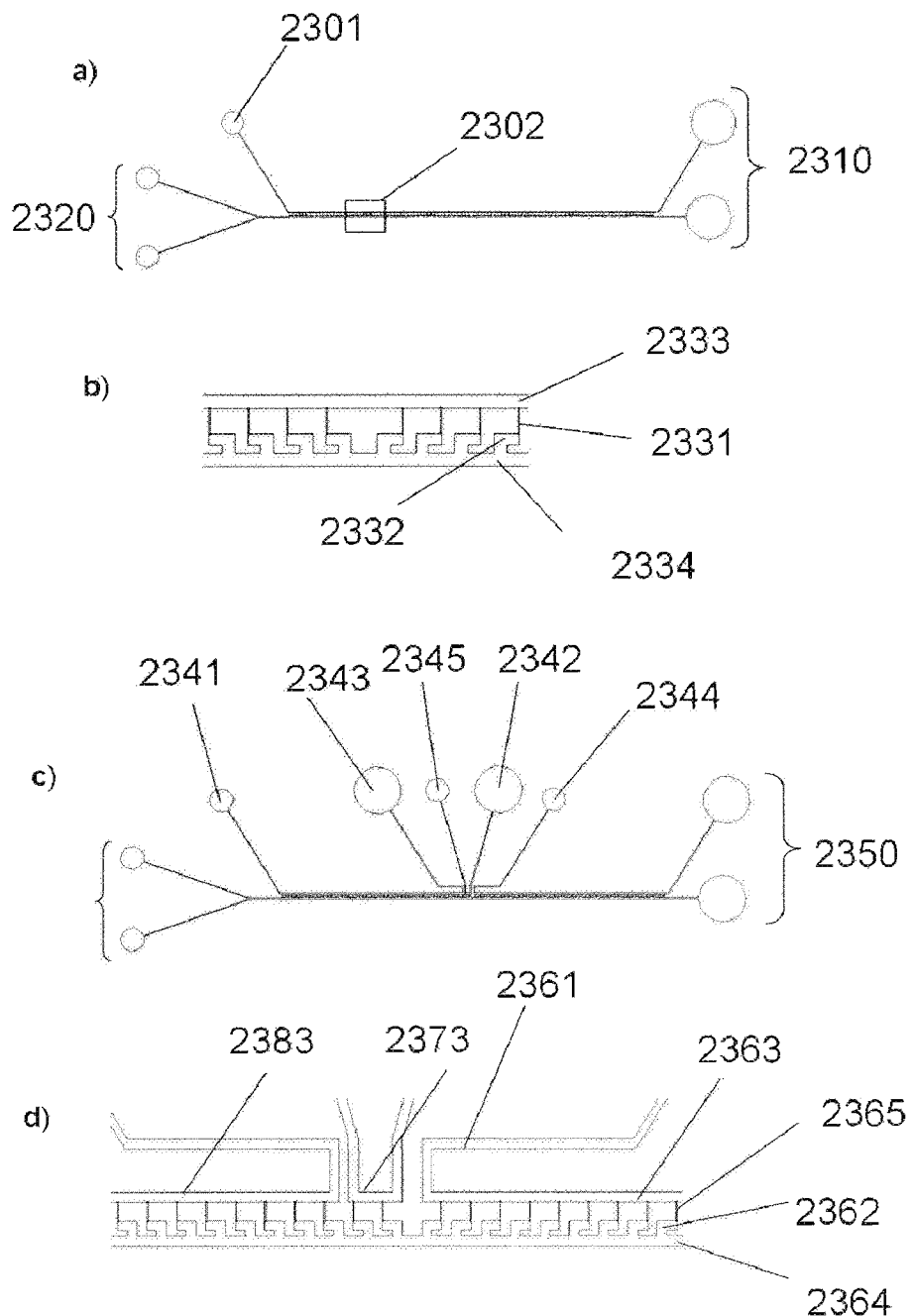
FIG. 23A. Example of an access channel to release specific fluidic packets.

Total Extraction of Sample Volume from Compartments by Integration of External Access Channels Another method for extraction of sample from the compartmentalized regions is through the introduction of external access channels. External access channels can be utilized to remove sample volumes in a controlled fashion (FIG. 23), and these access channels can be integrated into the dicretization device to address and facilitate removal of individual selected discretized samples. The external access channels are connected to the sample compartments by a sample compartment channel. The dimensions of the external access channels and sample compartment channels may be optimized to suit a particular application. FIG. 23 displays some possible integration techniques, both in the entire array (FIG. 23(a,b) and in a region selective manner (FIG. 23(c,d). Due to the device flexibility in the discretization region, these external access channels may be used with any of the previously detailed discretization geometries. FIG. 23(a) shows an example of a discretization device with an external access channel running parallel to the main channel. This external access channel connects to sample compartment channels that provide access to each sample compartment. The external access channels can be configured to interact with as many or as few sample chambers as is desired, as is illustrated in FIG. 23(c,d), an example of a discretization device with three external access channels used to independently address different sample compartments. By applying a positive pressure to these external access channels, for example, the discretized samples can be pushed from the compartments into the immiscible phase flow or into the main channel where they can be transported away for further analysis. Besides using flow to transport the dislodged or ejected sample volume, other methods of applying force to move the sample volumes is possible, such as radiation pressure, electric field derived forces, surface tension derived forces, thermal gradient derived forces, or magnetic forces.

Figure 23B:
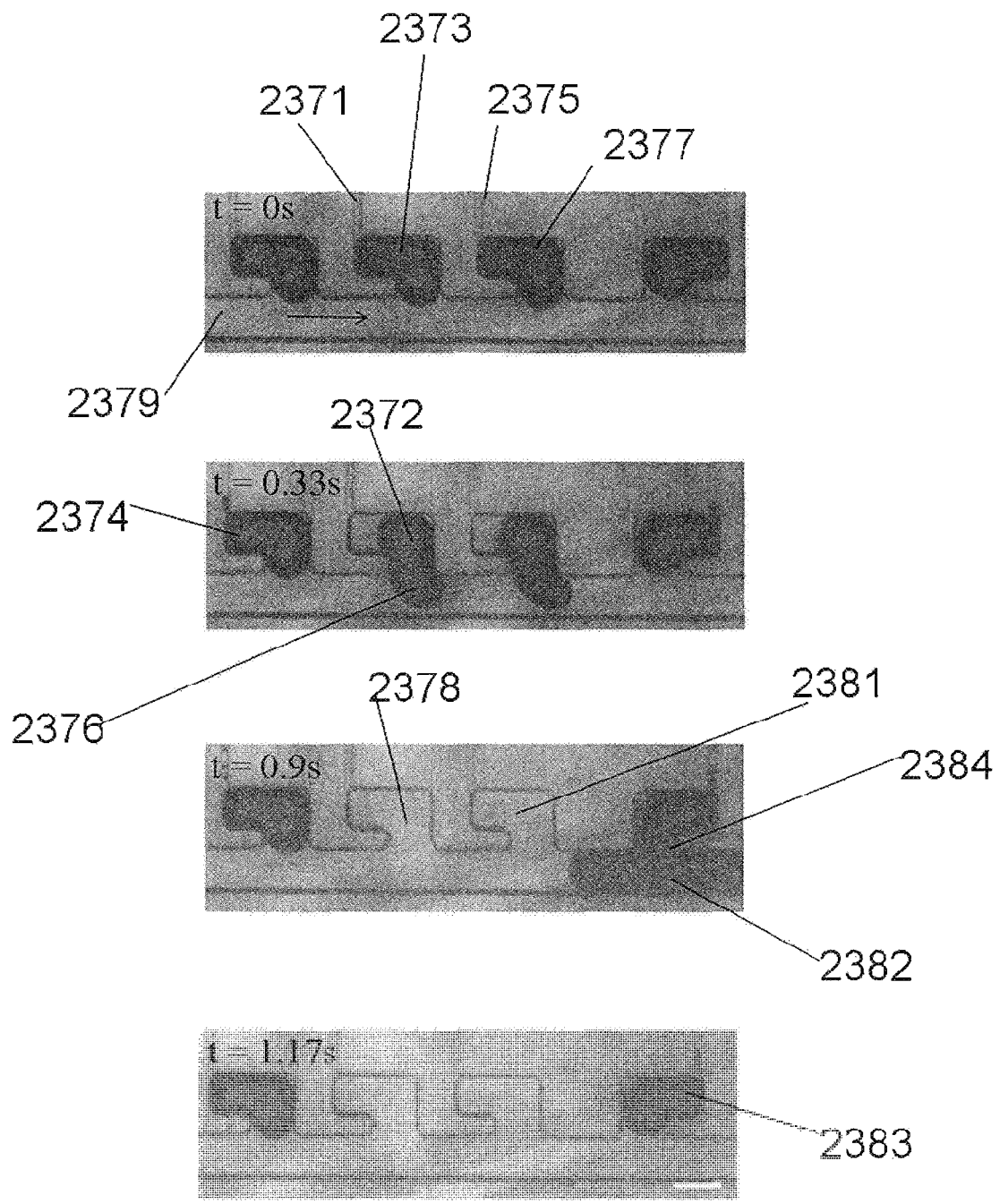
FIG. 23B shows sequential images of fluidic packets selectively released by applying a positive pressure in an external access channel connected to the respective fluidic harbors.
Figure 23C:
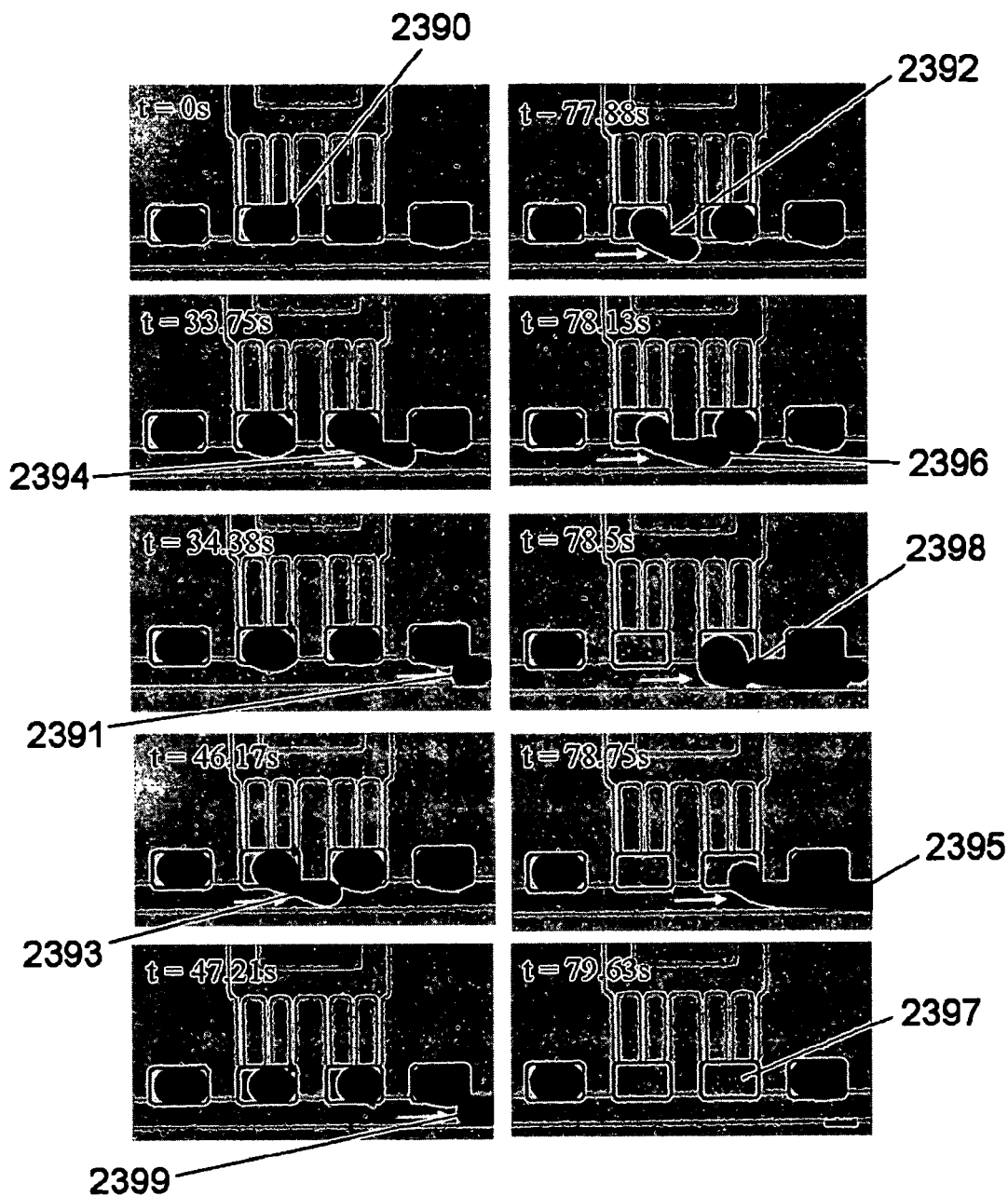
FIG. 23C shows sequential images of a fluidic packet releasing a portion when a positive pressure was applied to access channel causing a flow into the access channel.

In one embodiment, fluidic packets can be released from fluidic harbors by a flow into an access channel. FIG. 23A illustrates an access channel incorporated next to fluidic harbors to release the fluidic packets, both in the entire fluidic lattice (FIG. 23A(a,b)) and in a selective manner (FIG. 23A(c,d)). FIG. 23A(b), which is a magnified view of FIG. 23A(a) enclosed by outline 2302, shows an example of a fluidic lattice with an external access channel 2333 running parallel to the main flow channel 2334. The external access channels can be configured to interact with as many or as few fluidic harbors as is desired, as is illustrated in FIG. 23A(c,d), an example of a fluidic lattice with three external access channels 2363, 2373, and 2383 used to independently address different fluidic harbors. By applying a positive pressure to these external access channels, fluidic packets can be released from the fluidic harbors into the main channel where the packets can be transported away for further analysis. FIG. 23B shows sequential images of two fluidic packets 2373 and 2377 selectively released by applying a positive pressure in an external access channel connected to the respective fluidic harbors. The flow rate in main flow channel 2379 was 1 µL/min. The positive pressure was applied by operating an oil-filled syringe manually. The scale bar corresponds to 100 µm. FIG. 23C shows sequential images of fluidic packet release using an alternative access channel configuration.

In one embodiment, a portion of a fluidic packet can be released from fluidic harbors by a flow into an access channel. FIG. 23C shows sequential images of fluidic packet 2390 releasing a portion 2394 (and 2391 later) when a positive pressure was applied to access channel 2389, causing a flow into the access channel. The positive pressure was applied by operating an oil-filled syringe manually. The flow rate in the main channel was 1 µL/min. The scale bar corresponds to 100 µm.

Figure 27:
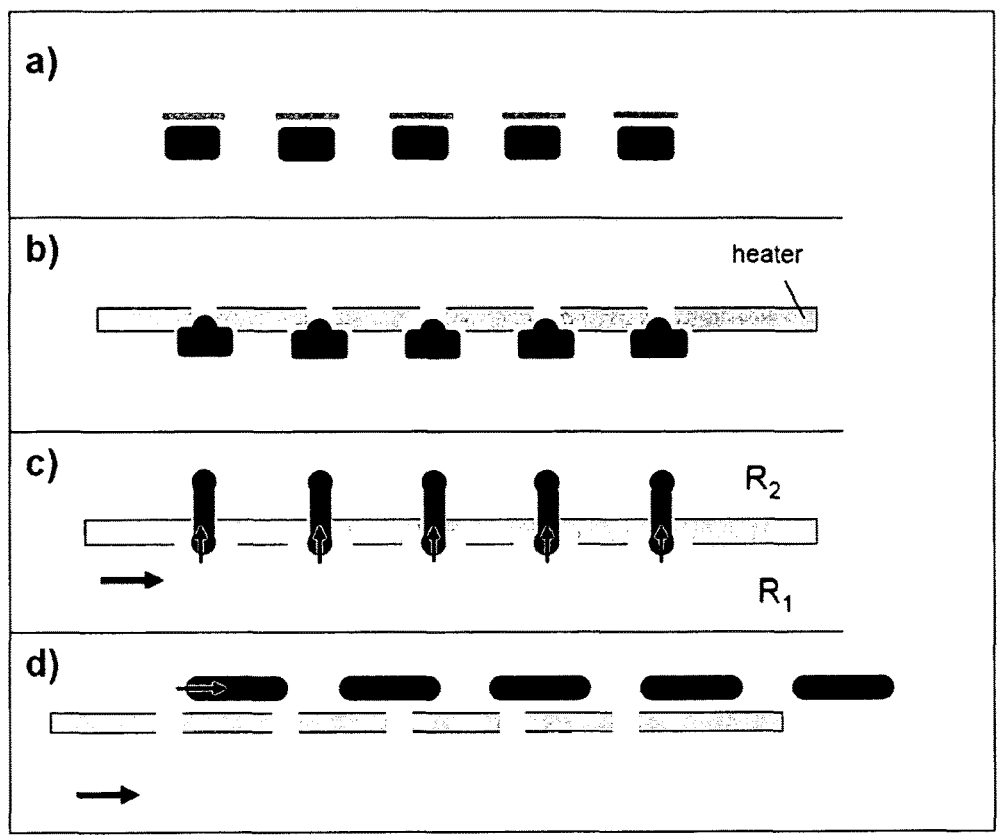
FIG. 27. Temperature and/or solvent degradable membrane valving for encapsulated sample array removal. a) Temperature and/or solvent responsive material is either sandwiched between the channels or filled into the narrow exit feed channel. b) Upon heating the membrane alone or through the additional dissolving effects of the solvent, the valves dissolve, opening up the exit channel. c) The continuous phase is flowed and as $R_2$ is a lower resistance pathway than $R_1$, the sample volumes move into the exit channel. d) Sample volumes fully occupy the exit channel and further continuous phase infusion moves them towards the exit. Besides flow, other methods of applying force to move the sample volumes is possible, such as radiation pressure, electric field derived forces, surface tension derived forces, thermal gradient derived forces, or magnetic forces.
Figure 27A:
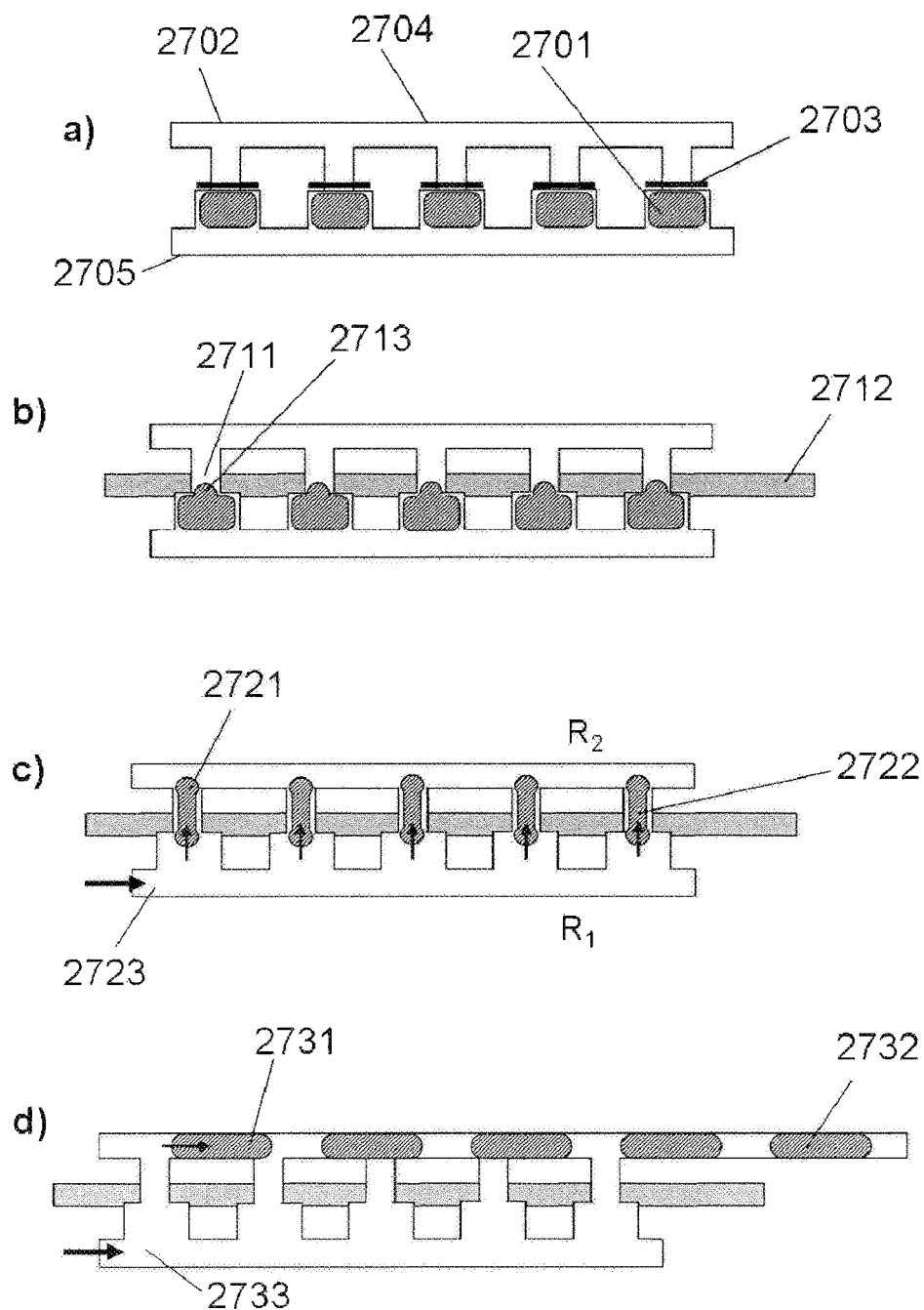
FIG. 27A. Schematic of releasing packets from fluidic harbors into an access channel by destruction of a temporary wall.

In another embodiment, fluidic packets are separated from an access channel by a temporary wall. As illustrated in FIG. 27A, an access channel 2702 is separated from the fluidic harbors 2701 by a temperature- or solvent-responsive wall or membrane 2703 (FIG. 27A(a)), Upon heating with a strip heater 2712 or through dissolution effects of a solvent, the membrane dissolves/breaks down, allowing fluidic communication between fluidic harbors and the access channel (FIG. 27B(b)). The fluidic packets residing within the fluidic harbors then can flow into the access channel for collection. If R2 is a lower fluidic resistance pathway than R1, the fluid packets can move into the access channel (FIG. 27B(c)). Once in the access channel, the fluidic packets move downstream for further analysis (FIG. 27B(d)). In addition to direct heating schemes with a strip heater and wall or membrance dissolution, other wall or membrane techniques may be employed such as direct and/or indirect optical heating methods to initiate wall or membrane breakdown.

Figure 28:
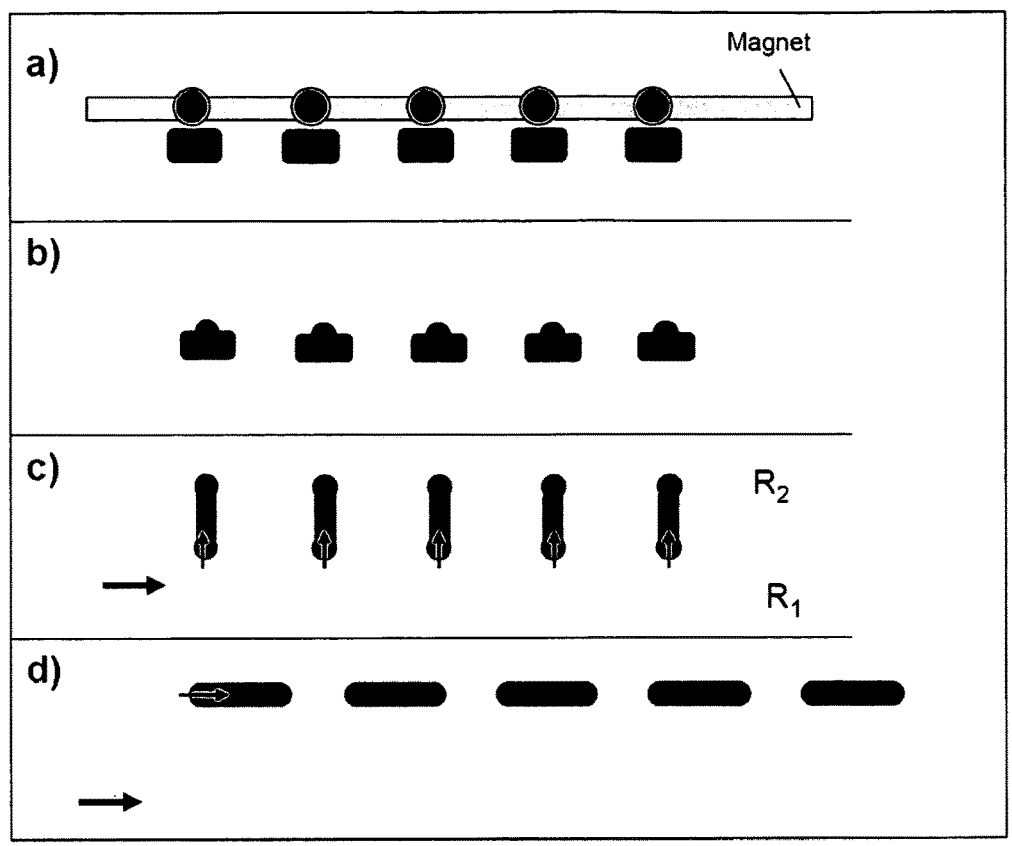
FIG. 28. Magnetic temporary valve for encapsulated sample array removal. a) Magnetic beads are aligned into regions above the exit channels and a magnet is placed below the chip causing the beads to be attracted downwards, fully or partially sealing the exit channel. b) Upon removal of the magnet under the chip, the beads release opening up the exit channel. e) The continuous phase is flowed and as $R_2$ is a lower resistance pathway than $R_1$, the sample plugs move into the exit channel. d) Sample plugs fully occupy the exit channel and further continuous phase infusion moves them towards the exit. Besides flow, other methods of applying force to move the sample volumes is possible, such as radiation pressure, electric field derived forces, surface tension derived forces, thermal gradient derived forces, or magnetic forces. Besides magnetic beads, other materials with suitable magnetic properties can be used, such as permanent magnets and ferrofluids.
Figure 28A:
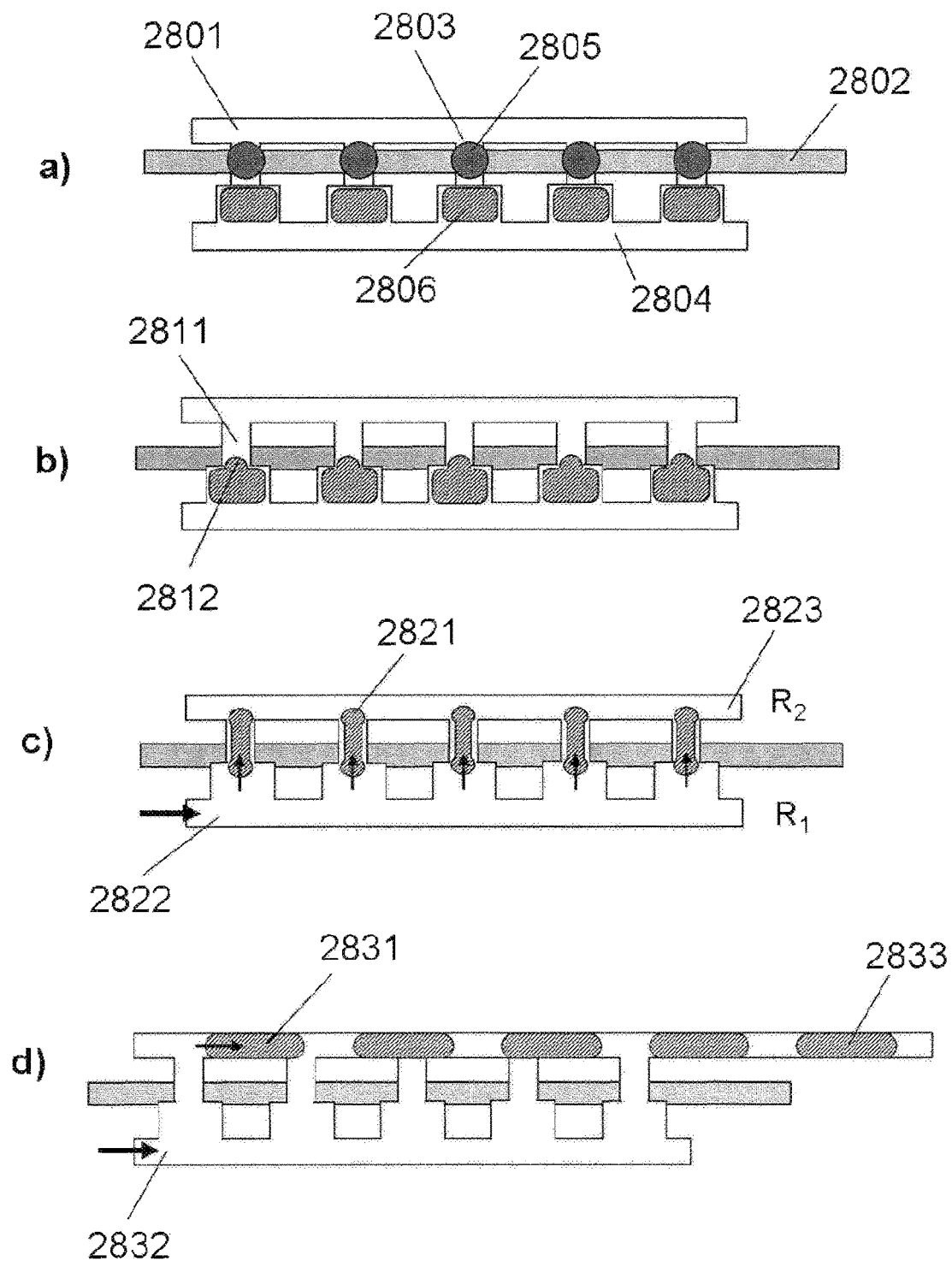
FIG. 28A. Schematic of releasing packets from fluidic harbors into an access channel by opening a temporary valve.

In another embodiment, fluidic packets are separated from an access channel by a switchable valve. For example, as shown in FIG. 28A, an on-chip valve 2803 can be constructed between a fluidic harbor and an access channel 2801 to control the release of a fluidic packet 2806. As an example, magnetic beads 2805 could be positioned between a fluidic harbor and an access channel, preventing fluidic communication. A magnet strip 2802 was placed below the fluidic lattice to control the position of magnetic beads (FIG. 28A(a)). Upon removal of the magnet under the fluidic lattice, the beads can be released, allowing fluidic communication between the fluidic harbors and the access channels (FIG. 28A(b)). Once the access channel is open, fluidic packets may enter the access channel if R2 is a lower resistance pathway than R1 (FIG. 28A(c)). Once in the access channel, the fluidic packets may merge or remain distinct and move downstream for further analysis (FIG. 28B(d)). The use of a permanent magnet is shown; however, though the implementation of an electromagnet the resistance can be tuned between R1 and R2 to allow for a partial removal of fluidic packet from the chambers. Other direct or indirect mechanical deformation schemes to effect valving can also be used, such as the use of small mechanical points (e.g. from a Braille display) to deform the substrate and thus be used as a valve.

Extraction of Compartmentalized Samples Through the Use of Heat to Effect Interfacial Tension or Thermal Expansion In certain embodiments, fluidic packets can be released from fluidic harbors by exerting a force on fluidic packets. Forces may include but are not limited to vacuum, pneumatic pressure, acoustic pressure, ultrasonic pulses, radiation pressure, electromagnetic field, electrowetting, photo-induced surface wetting, electrocapillarity, surface or interfacial tension, thermal-gradient-derived forces, electrostatic interaction, or magnetic forces.

Figure 24:
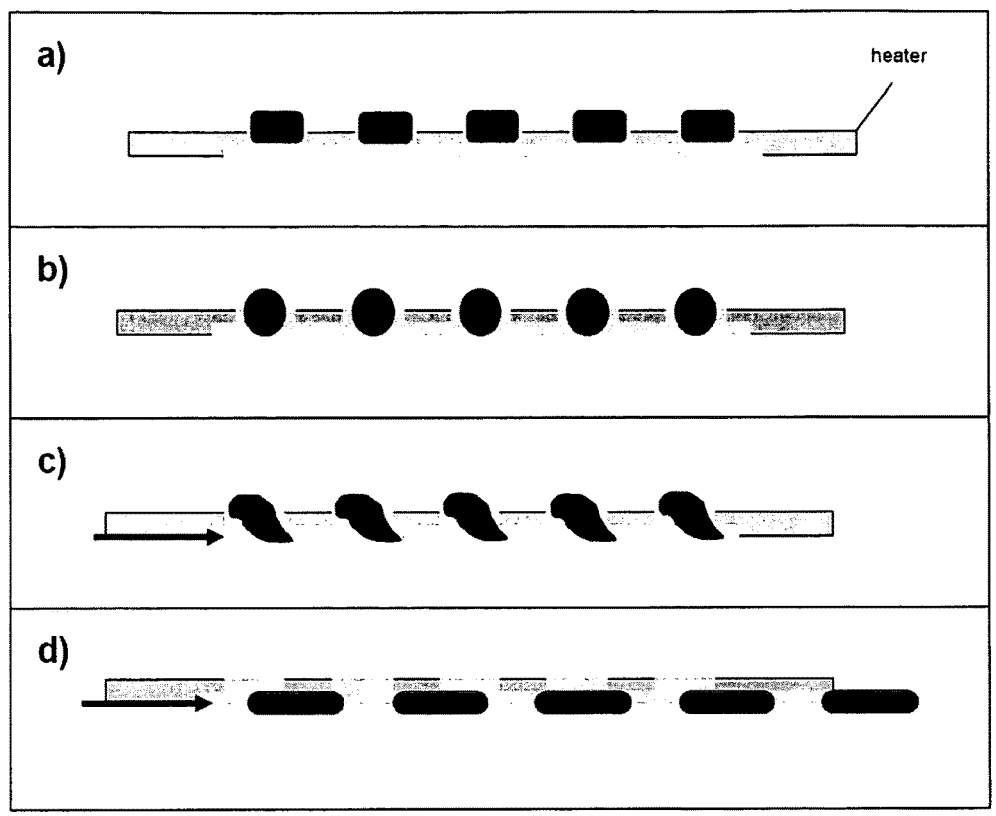
FIG. 24. Sample removal scheme through interfacial heating. a) Schematic of filled sample compartments with patterned or inserted heaters along the main channel length. b) A representation of the interface as the tension decreases and it is freer to deform. c) Application of the continuous phase flow (direction indicated by arrow) to aid in removal of sample from compartments. d) Upon release from the compartments the sample forms a plug or droplet and flows down the channel driven by the continuous phase flow. Rather than using flow, other methods of applying force to the sample volume to aid in removal is possible, such as radiation pressure, electric field derived forces, surface tension derived forces, thermal gradient derived forces, or magnetic forces.

Sample extraction from the compartments can be aided through the use of temperature to vary (e.g. lower) the interfacial tension (IFT) of the sample within the compartment. For example, lowering the IFT makes the sample volumes more susceptible to interface deformation and easier to remove by flow from the compartments. A scheme of this can be seen in FIG. 24, where patterned heating pads are used at the sample-immiscible phase boundary. These temperature pads can be tuned to allow regions to release sample preferentially and selectively while flowing the immiscible phase. For example, only the interface of a few pre-determined sample compartments are heated. Upon release from the chambers, the sample forms a plug or droplet and is flowed down the channel driven by the continuous phase flow. Besides flow, other methods of applying force to move the sample volumes is possible, such as radiation pressure, electric field derived forces, surface tension derived forces, thermal gradient derived forces, or magnetic forces.

Figure 24A:
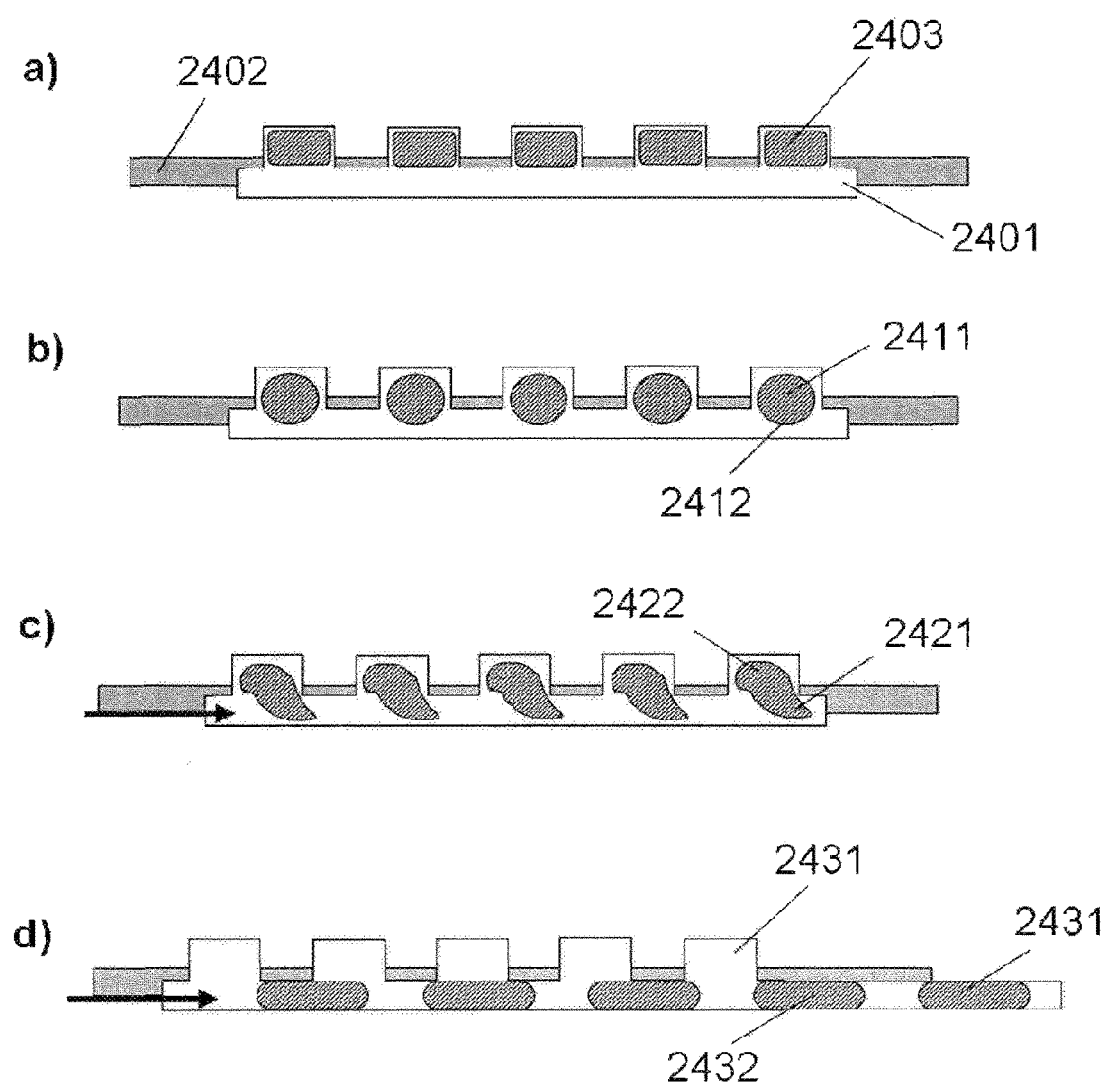
FIG. 24A. Schematic of releasing packets from fluidic harbors by heating.

In certain embodiments, fluidic packets can be released from fluidic harbors by changing a temperature. Changing a temperature directly alters the interfacial tension and can allow the fluidic packets to be released from the fluidic harbors. A schematic of this embodiment can be seen in FIG. 24A, where patterned heating pads 2402 were positioned near the boundary of fluidic harbor 2403 and the main flow channel of the fluidic lattice 2401. These heating pads can be tuned to allow regions to release fluidic packets preferentially and selectively with a continuous fluid flowing. Upon release from the harbors, the fluidic packets flow down the channel driven by the continuous fluid phase flow. Additional schemes to achieve fluidic packet release include but are not limited to the use of a laser spot to heat the interface of the selected fluidic packet so as to change interfacial tension and to cause the fluidic packet to be released selectively from the fluidic harbor.

Rather than heating the interface to effect changes in IFT, the pattern heating pads can also be used to heat either the immiscible phase or aqueous phase to induce a thermally initiated volume change, thereby ejecting the sample from the compartment. For example, heating of the immiscible phase to create a bubble to dislodge the sample volume from the compartment.

Figure 29:
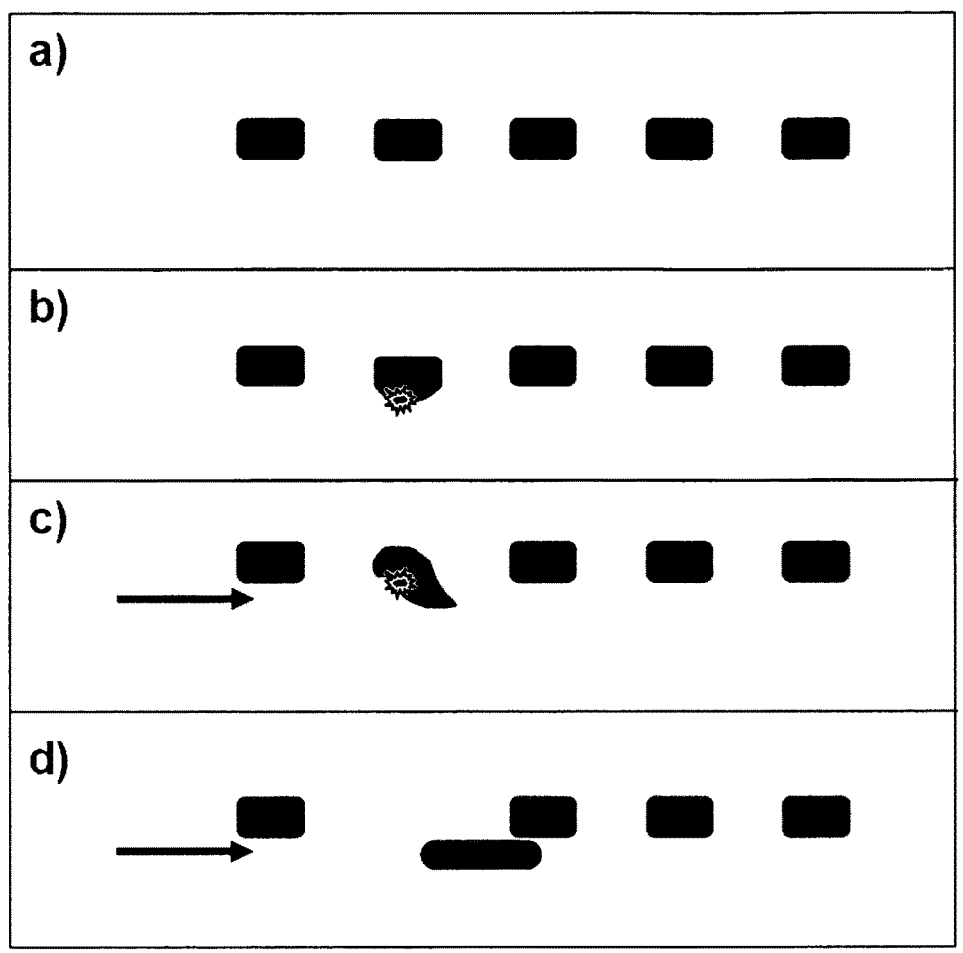
FIG. 29. Individual addressing and removal of sample from the compartments using direct or indirect optical heating. Through either direct heating of the discretized sample interface with the laser or through the use an absorptive material layered on the surface or in the sample volume or in the immiscible phase fluid. a) array of filled compartments (starbursts indicate laser illumination). b) Distortion of the interface due to the localized heating. c) Continuation of interface deformation, now coupled with the continuous phase flow directing the sample out of the chamber. d) Selected sample now released from the compartment and can flow freely down the main channel. Besides flow, other methods of applying force to move the sample volumes is possible, such as radiation pressure, electric field derived forces, surface tension derived forces, thermal gradient derived forces, or magnetic forces.
Figure 29A:
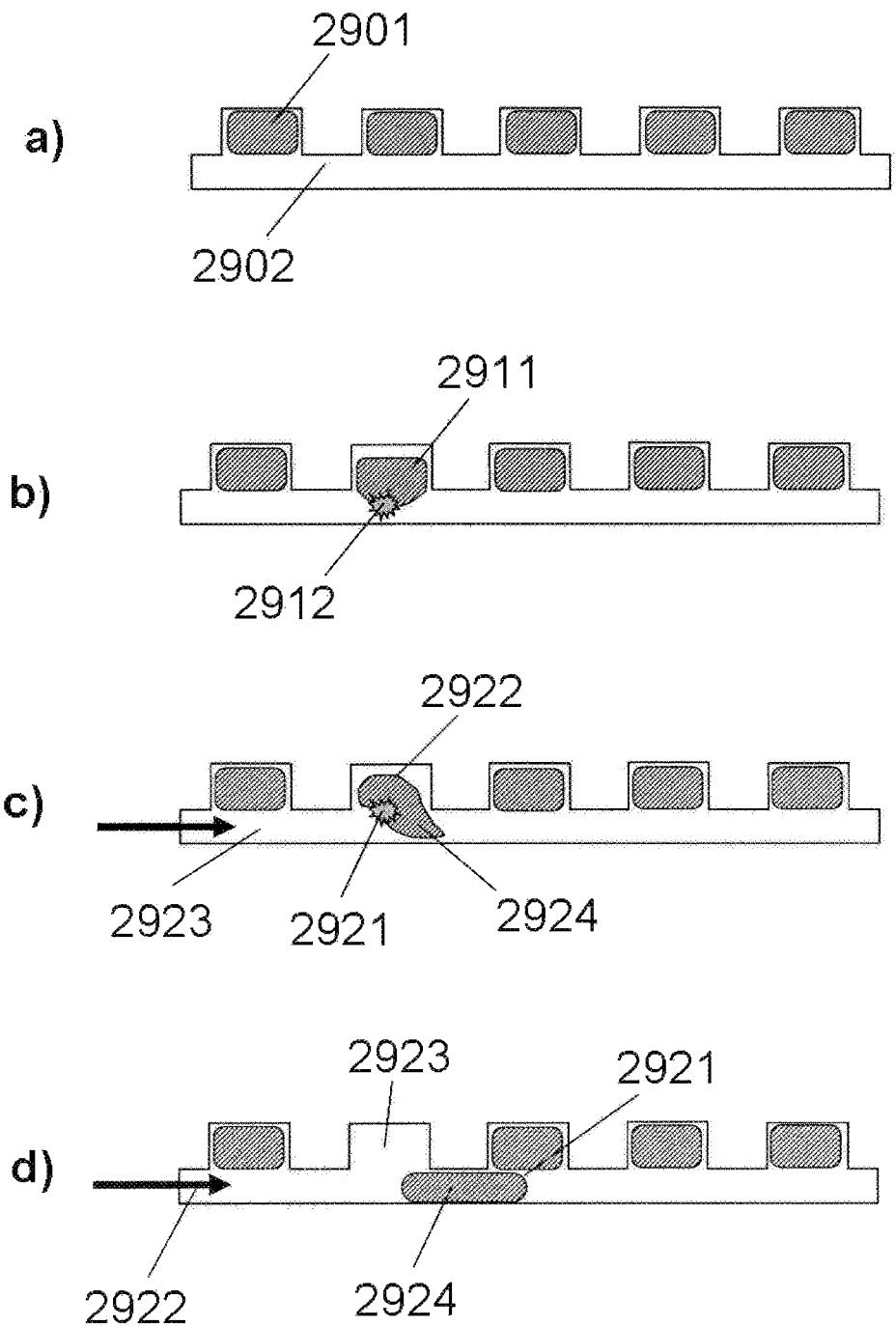
FIG. 29A. Individual release of packets from fluidic harbors by direct or indirect optical heating.

In certain embodiments, fluidic packets are released from fluidic harbors by a phase transition. In some embodiment, fluidic packets are released from fluidic harbors by generating a bubble. In an example, rather than heating a fluidic packet to effect changes in interfacial tension, the patterned heating pads can also be used to heat the packet to induce the generation of a gas bubble, thereby ejecting the fluidic packet from the harbor. In another example as illustrated in FIG. 25A, radiation sources (e.g. with a focused laser) may be used in lieu of thermal sources to cause a change in interfacial tension or induce a phase transition. By targeting a focused laser at the interfacial boundary 2501 between a fluidic packet 2502 and an immiscible continuous fluid 2503, the interface can be distorted by optical heating and subsequently causing release of the packet. As focused-laser systems are easily scalable, reconfigurable, and dynamic, it is also possible to individually address a fluidic harbor of interest and remove the packet from the harbor using either direct heating with a laser or through the use of an absorptive material layered on the surface. An example of such an individually addressable system can be seen in FIG. 29A, where among five illustrated fluidic packets, only packet 2911 was released into the main channel by focusing a laser at interface 2912.

Figure 25:
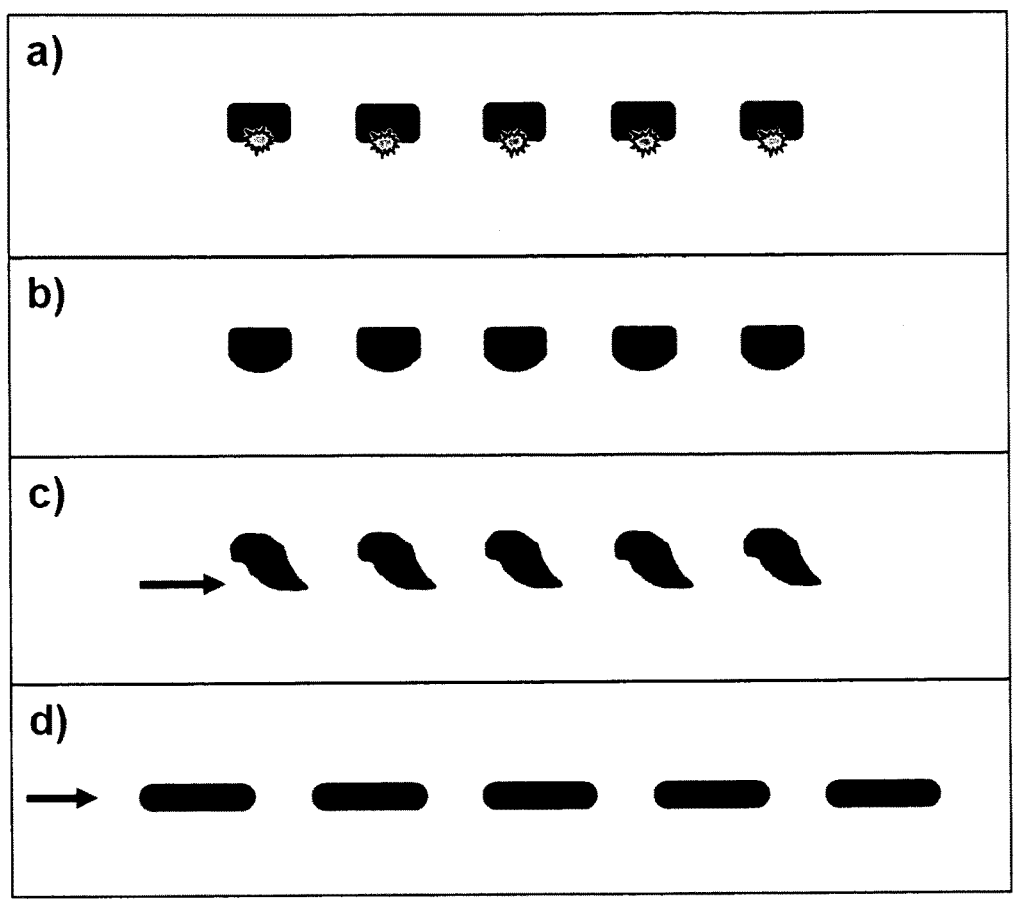
FIG. 25. Removal of sample from the compartment using direct or indirect optical heating. Through either direct heating of the discretized sample interface with the laser or through the use an absorptive material layered on the surface. a) filled compartments with starbursts indicating one of many possible laser positions on the sample in the compartment. b) Distortion of the interface due to the localized heating. c) Continuation of interface deformation, now coupled with the continuous phase flow directing the sample out of the compartment. d) Compartments fully emptied and the sample can now flow as a plug stream. Rather than using flow, other methods of applying force to the sample volume to aid in removal is possible, such as radiation pressure, electric field derived forces, surface tension derived forces, thermal gradient derived forces, or magnetic forces.
Figure 25A:
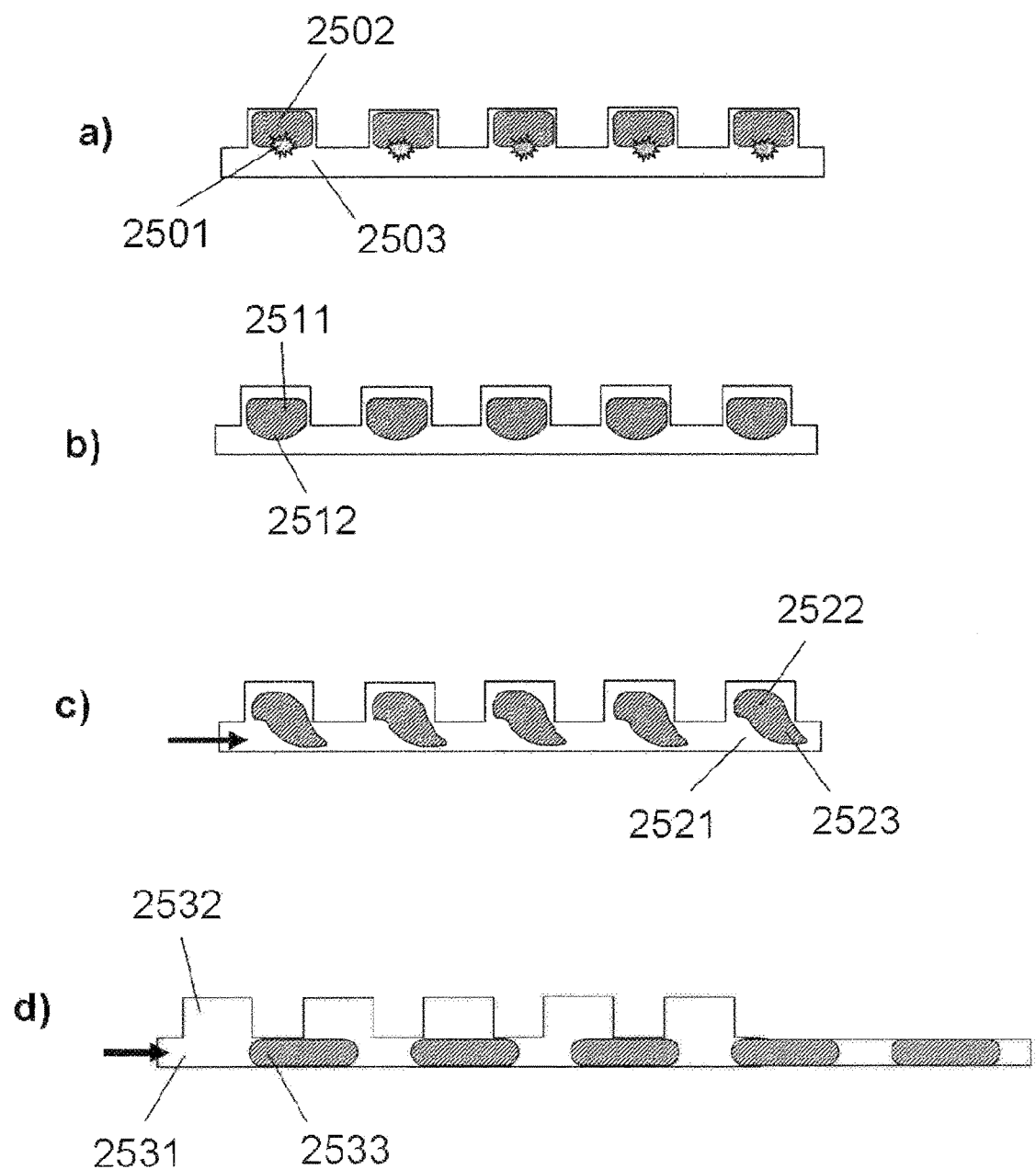
FIG. 25A. Schematic of releasing packets from fluidic harbors by interfacial optical heating.

In a similar manner as using a patterned heater to change the interfacial tension or to effect a thermal expansion, direct light absorption (e.g. with a focused laser) or indirect optical heating (e.g. absorption of surround material or patterned element) can also be used, as is illustrated in FIG. 25. As laser focus systems are easily scalable and dynamic, it is also possible to individually address a compartment of interest and remove the sample from the chamber using either direct heating of the droplet/plug interface with the laser or through the use an absorptive material layered on the surface. An example of the individually addressable system can be seen in FIG. 29.

As with heating using heating pads, once the interface has been deformed or a thermal expansion has occurred, the sample can now be flowed out of the chamber using the continuous phase, forming a droplet sample droplet/plug stream. Similarly, besides flow, other methods of applying force to move the sample volumes in the main channel is possible, such as radiation pressure, electric field derived forces, surface tension derived forces, thermal gradient derived forces, ultrasound, or magnetic forces.

Sample Extraction Using Electrowetting to Drive the Discretized Volume Out of the Chambers By integrating electrode patterning into the device it is possible to use an electrowetting scheme to direct droplet motion. This scheme requires electrodes to be patterned in the discretization chambers and in the main flow channel separated by a small distance (FIG. 26(a)). Using electrowetting to mobilize the sample plugs requires control of the charge placed on both of the electrodes. By varying the charge between them it is possible to change the wetting angle of the droplet on one of the electrodes, mobilizing the sample volumes and allowing the removal of them from the chambers.

Figure 26:
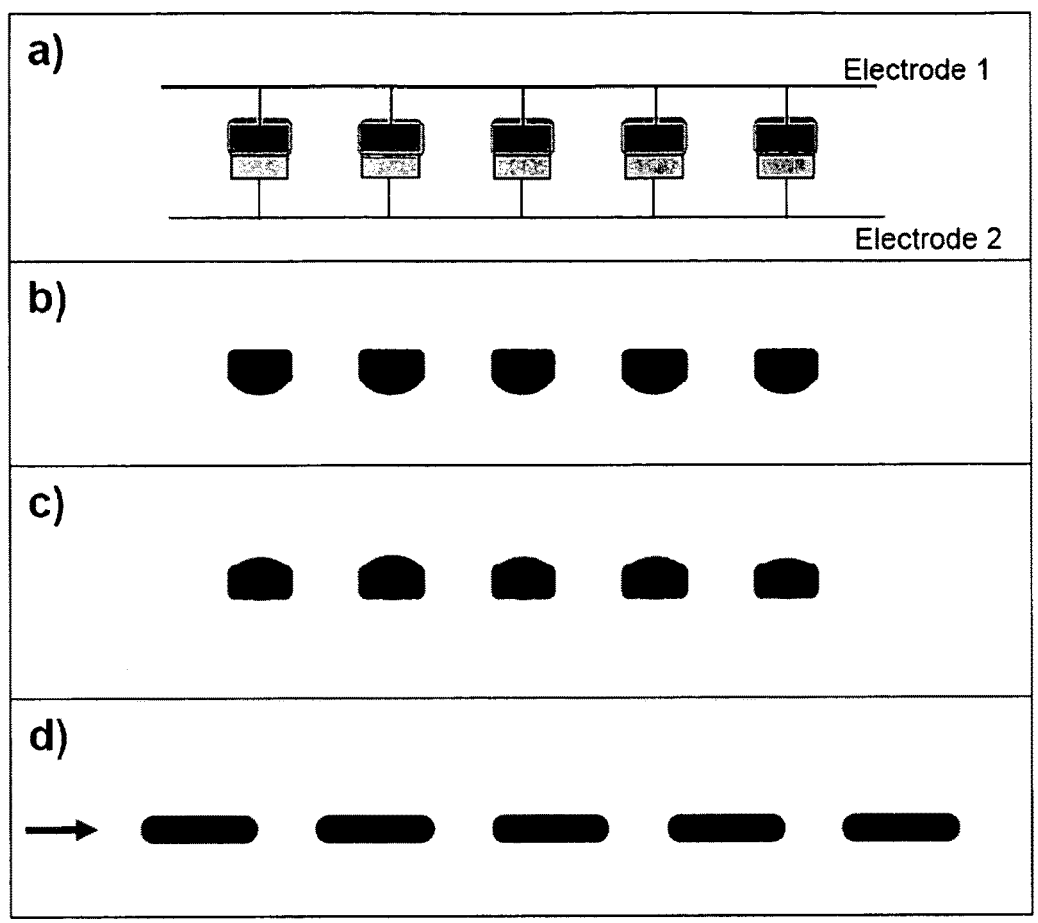
FIG. 26. Using electrowetting to mobilize the sample volumes and remove them from compartments. The sample in the compartments in (a) has been faded to display the electrodes. The electrodes have been omitted from (b-d) for clarity. Sample volumes can be individually addressed by using independent leads to the electrodes instead of in series. a) A sample array illustrating one possible electrode arrangement. b-c) As the voltage is changed between electrode 1 and 2 the sample begins to move and wet across onto electrode 2. d) Once the sample largely occupies electrode 2 the continuous phase can then be used to move the plugs downstream. Rather than using flow, other methods of applying force to move the sample volumes is possible, such as radiation pressure, electric field derived forces, surface tension derived forces, thermal gradient derived forces, or magnetic forces. Electrodes can also be implemented into the main channel to move the sample downstream using electrowetting. Other described methods to change the interfacial tension to facilitate droplet removal from chamber can be coupled with this electrowetting method for enhanced performance in removing and manipulating droplets from individual chambers.
Figure 26A:
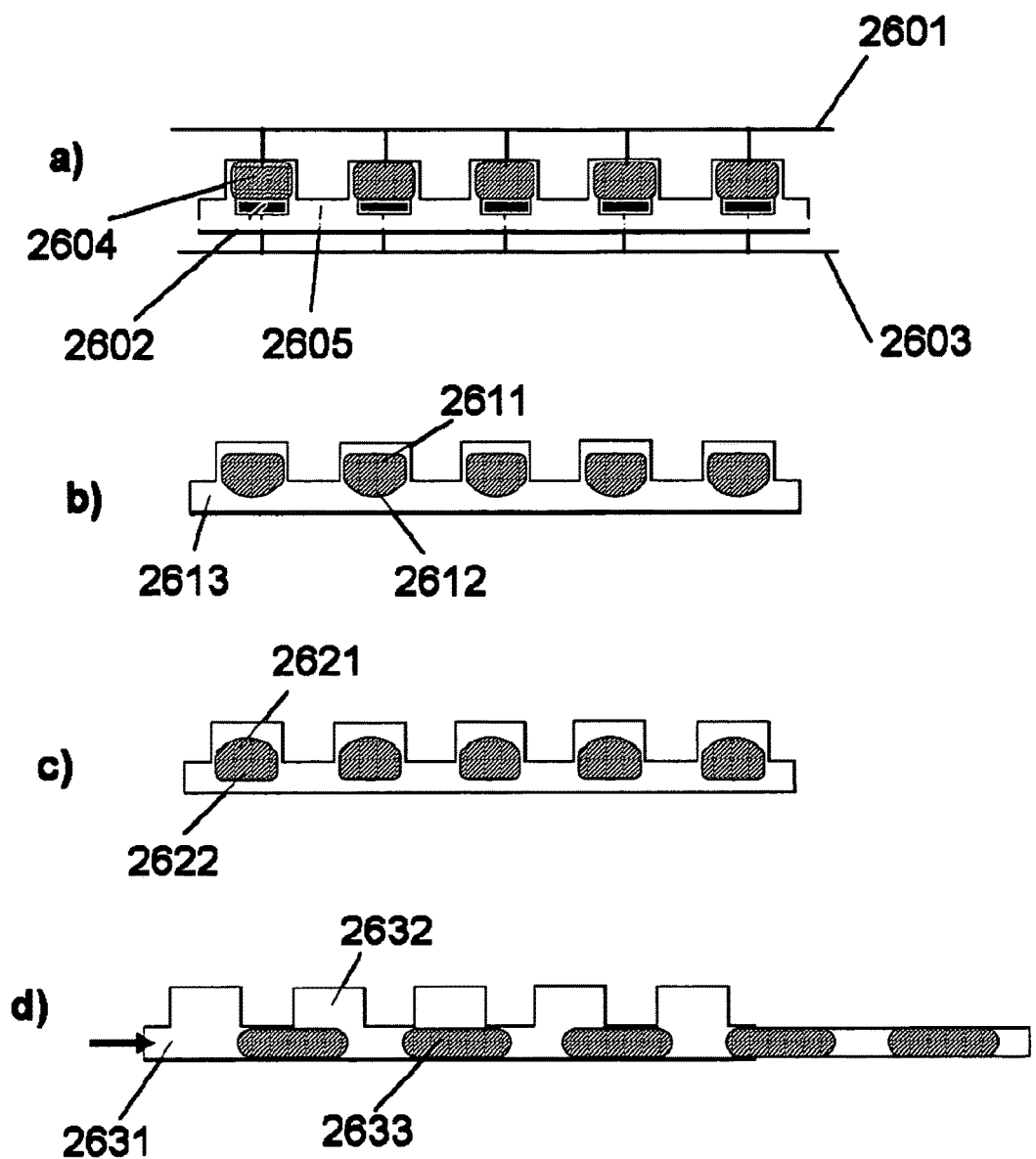
FIG. 26A. Schematic of releasing packets from fluidic harbors by electrowetting.

In one embodiment, fluidic packets are released from fluidic harbors by electrowetting. By integrating patterned electrodes 2604 (electrically connected to wire 2601) and 2602 (electrically connected to wire 2603) in the fluidic harbors and in the main flow channel 2605 (FIG. 26A(a), it is possible to increase the surface wetting of the main flow channel as the electrodes are charged, thus inducing a fluid packet to move out of the harbor and into the main flow channel. The fluidic packets may be individually addressed by using independent leads to the electrodes instead of in series. FIG. 26A illustrates a schematic of this approach, where a collection of five fluidic packets were extracted simultaneously from the fluidic harbors into the main flow channel. Surface wetting may also be controlled by optical means where illumination by light causes a change in the wetting properties (e.g. due to photo-induced changes in molecular orientation or alignment of surface molecules) of the surface.

The discretized samples can also be individually addressed by using independent leads to the electrodes instead of in series. FIG. 26 illustrates a possible utilization of the technique, where a series of droplets are extracted simultaneously from the chambers into the immiscible flow. Electrodes can also be implemented into the flow channel to move the sample downstream using electrowetting.

Sample Extraction Using Membrane Separation to External Access Channels to Cause a Temporary Closure Introduction of external access channels can direct sample flow along a different path after discretization. These channels can be separated from the main discretization chambers by a temperature and/or solvent degradable membrane which allows for valving and separation of the sample chamber from the access channel. An example implementation can be seen in FIG. 27. This separating membrane can be a temperature and/or solvent responsive material and the membrane is sandwiched between the sample chambers and access channel (FIG. 27(a)), Upon heating the membrane alone or through, the additional dissolution effects of the solvent, the membrane dissolves/breaks down, opening up the exit channel (FIG. 27(b)). Once the membrane has been removed, the external access channel is now accessible to the sample chamber and the continuous or immiscible phase can be flowed. As $R_2$ is a lower resistance pathway than $R_1$, the sample plugs move into the exit channel (FIG. 27(c)). Once in the external access channel, the sample plugs, upon further continuous phase infusion, move downstream for further analysis (FIG. 27(d)). Although a direct heating scheme is shown, direct and/or indirect optical heating methods can also be used to initiate membrane breakdown. A wide range of other membrane breakdown mechanisms as described above can also be used.

Sample Extraction Using Externally Manipulated Channel Valving

External access channels can also have modulated access through the use of direct or indirect on-chip valving (e.g. magnetic or with mechanical deformation), for compartmentalized sample array removal. An example implementation of this can be seen in FIG. 28. Magnetic beads are aligned into regions above the exit channels and a magnet is placed below the chip causing the beams to be attracted downwards, fully or partially sealing the exit channel (FIG. 28(a)). Upon, removal of the magnet under the chip, the beads are released, opening up the external access channel (FIG. 28(b)). Once the external access channel is open the continuous phase can be flowed and as $R_2$ is a lower resistance pathway than $R_1$, the sample plugs move into the external access channel (FIG. 28(c)). Once in the external access channel, the sample plugs, upon further continuous phase infusion, move downstream for further analysis (FIG. 28(d)). A fixed magnet is shown, however though the implementation of an electromagnet the resistance can be tuned between $R_1$ and $R_2$ to allow for a drop wise removal of sample from the chambers. Using an electromagnet will also make the chambers re-sealable allowing a simple valving implementation, which can be used to flush and replenish the chip for further use. Other direct or indirect mechanical deformation schemes to effect valving can also be used, such as the use of small mechanical points (e.g. from a Braille display) to deform the substrate and thus create addressable valving.

Individual Addressability and Sample Removal Using Optical Force Effects

Figure 30:
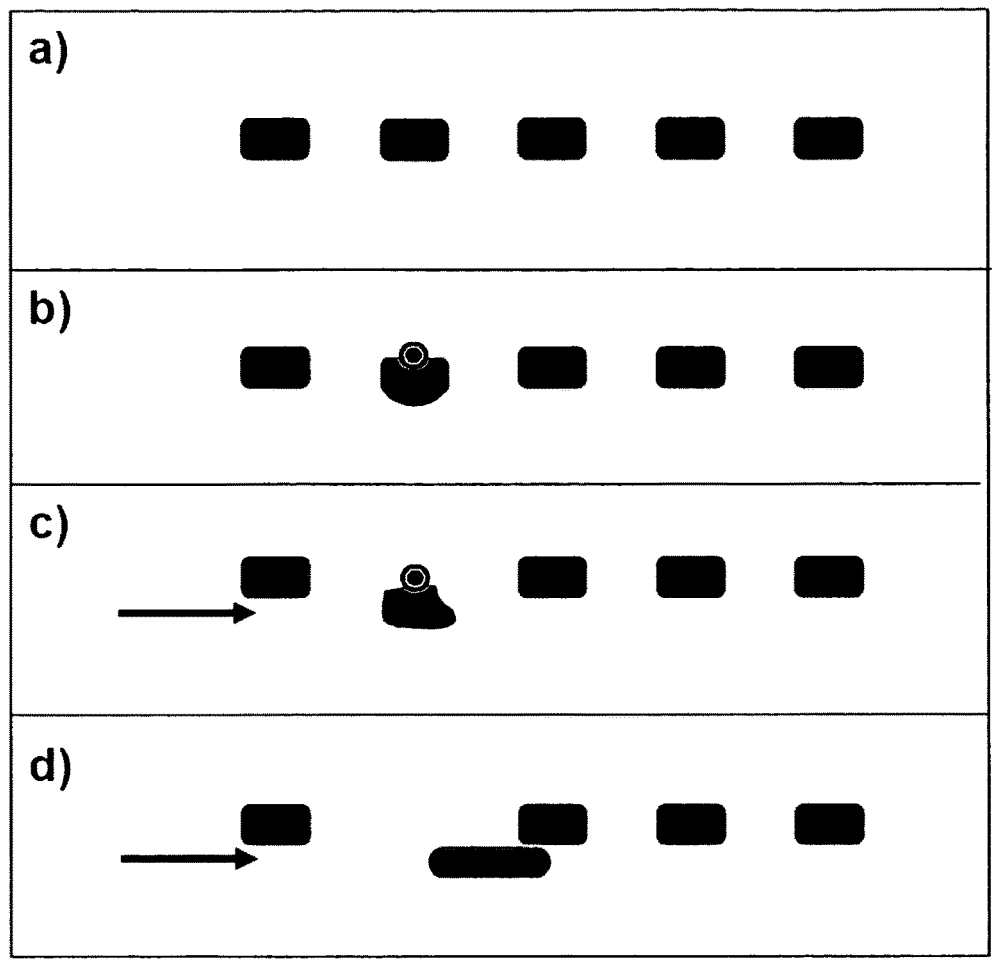
FIG. 30. Individual addressing sample removal from a compartment using direct or indirect optical force and/or radiation pressure. Through either the attractive or repulsive forces generated through interactions of the beam with the sample. a) array of filled compartments (red circles indicate laser illumination). b) Distortion of the interface due to optical forces. c) Continuation of interface deformation, now coupled with the continuous phase flow directing the sample out of the chamber. d) Selected sample now released from the compartment and can flow freely down the main channel. Besides flow, other methods of applying force to move the sample volumes is possible, such as radiation pressure, electric field derived forces, surface tension derived forces, thermal gradient derived forces, or magnetic forces.

In addition to heating effects, individual discretized sample removal from a compartment can be made using direct or indirect optical force and/or radiation pressure, through either the attractive or repulsive forces generated through interactions of the beam with the sample. An implementation of this is illustrated in FIG. 30. The laser is used to impart a force on the sample, distorting the interface and/or moving the interface due to the optical radiation force (FIG. 30(b,c)). Using this attractive/or repulsive force (depending on the refractive index of the mediums and the shape and size of the beam used) the selected sample can be released from the compartment and can flow freely down the channel (FIG. 30(c,d)). Besides flow, other methods of applying force to transport the sample volumes in the main channel is possible, such as radiation pressure, electric field derived forces, surface tension derived forces, thermal gradient derived forces, ultrasound, or magnetic forces.

Figure 30A:
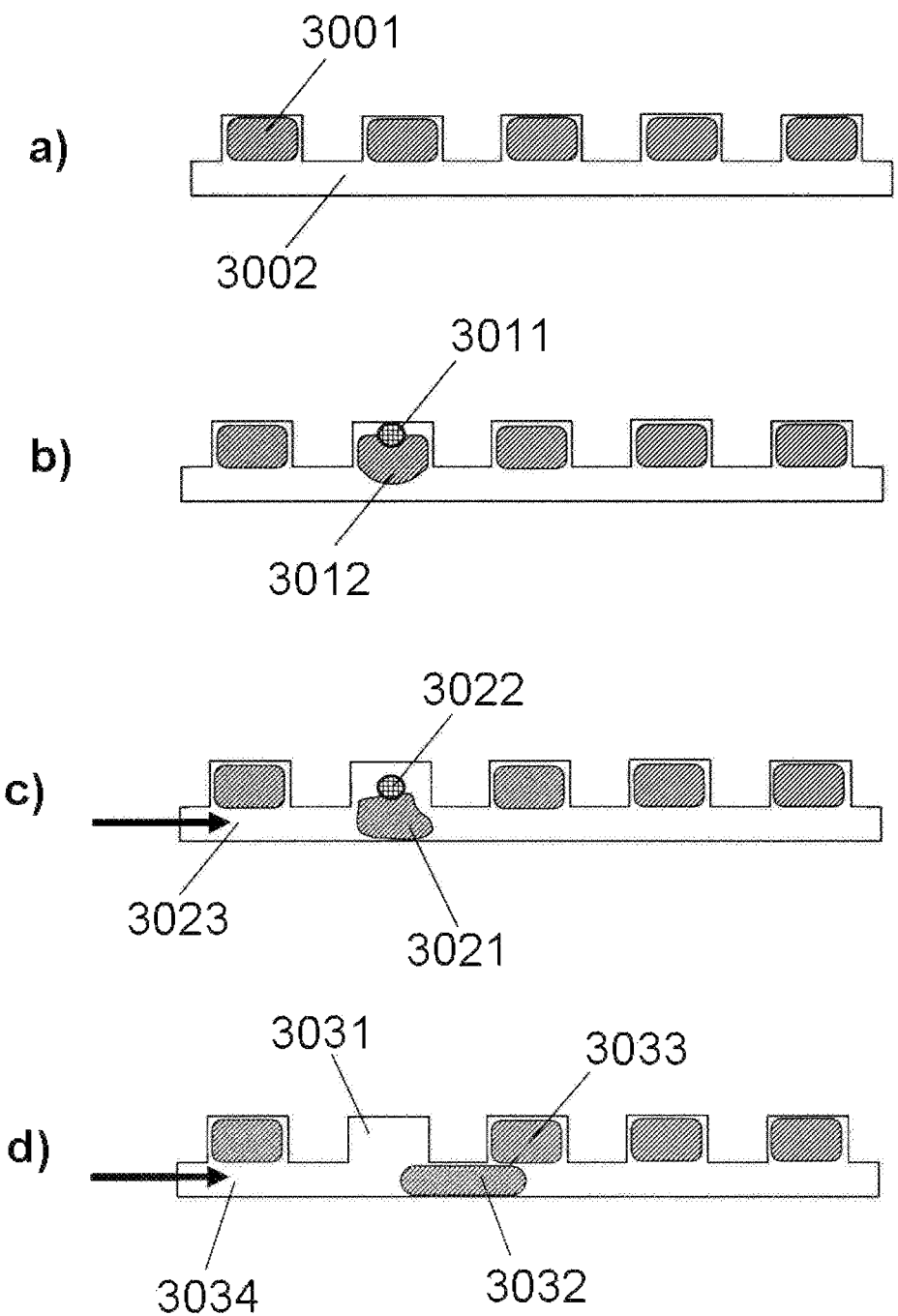
FIG. 30A. Individual release of packets from fluidic harbors by optical forces.

In certain embodiments, fluidic packets are released from fluidic harbors by optical forces. As an example, individual fluidic packets may be removed from a fluidic harbor using direct or indirect optical force or radiation pressure, through either attractive or repulsive forces generated by interaction of a laser beam with a fluidic packet. FIG. 30A illustrates the implementation of this method. A laser was used to impart an optical radiation force 3011 on a fluidic packet 3001, distorting the interface 3012 and/or moving the interface (FIG. 30A(b,c)). Using this attractive/or repulsive force (which depends on the refractive index of the surrounding fluid relative to the fluidic packet and the shape and size of the laser beam used), selected fluidic packets can be released from fluidic harbors (FIG. 30A(c,d)).

Figure 31:
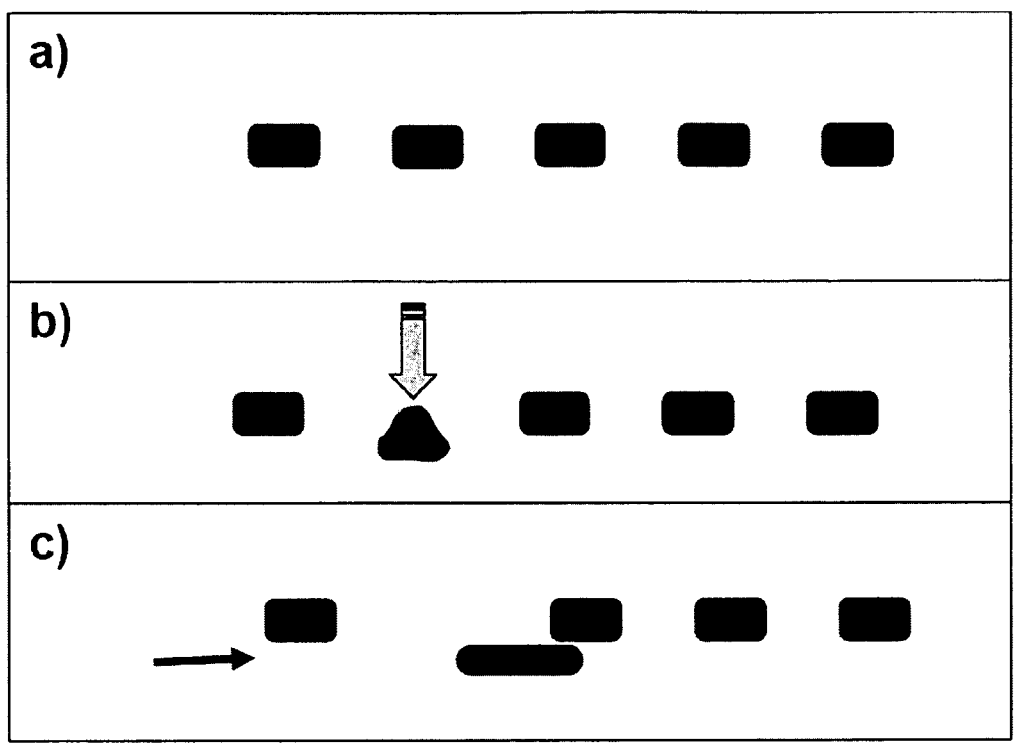
FIG. 31. Individual sample ejection through direct pressure actuation (this process would also allow large numbers to be released if arrays of actuators can be aligned with the compartments). a) The compartments are filled with sample. b) Direct pressure is applied above the compartment distorting the sample plug and directing it back into the main channel. c) Application of continuous phase flow allows for transport of the sample volume away from the sample compartment array downstream. Besides flow, other methods of applying force to move the sample volumes is possible, such as radiation pressure, electric field derived forces, surface tension derived forces, thermal gradient derived forces, or magnetic forces.
Figure 31A:
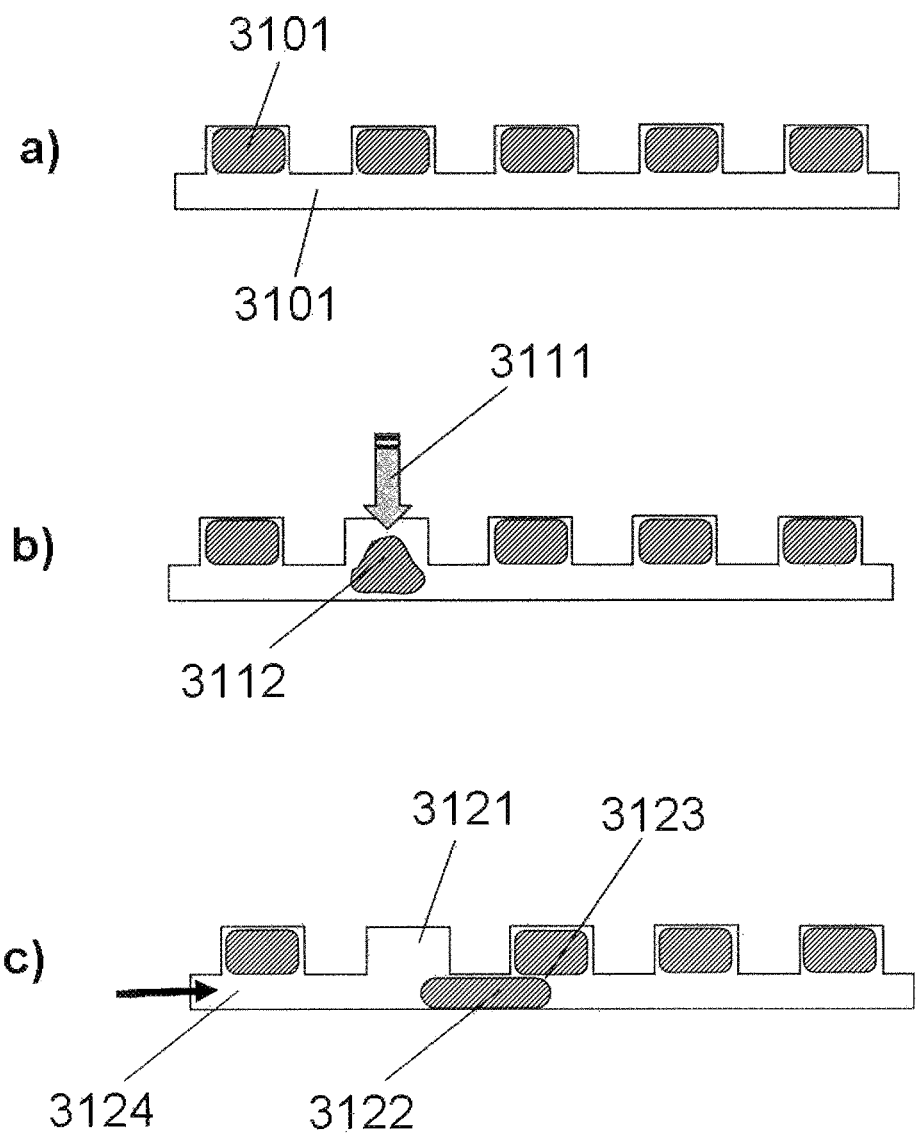
FIG. 31A. Individual release of packets from fluidic harbors by compression.

Individual Addressability and Sample Removal Using Directed Pressure to the Compartments In certain embodiments, fluidic packets are released from fluidic harbors by compression. An illustration of this method can be seen in FIG. 31A. As an example, a fluidic lattice may be constructed out of an elastomeric material such that upon application of compressive forces (e.g. pressure) 3111 the fluidic harbors contract or collapse, ejecting the fluidic packets 3112 within. It is possible that an array of actuators may be positioned above or below the fluidic lattice, and that these actuators may be independently programmed to exert compressive forces on the fluidic harbors. For example, the use of an array of individually programmable mechanical points, such as that from a Braille display, can be used to achieve the release method of fluidic packet described here.

Through the use of externally applied direct pressure to the compartments (above, below or in the plane), it should be possible to temporarily collapse the chamber, effectively ejecting individual samples, squeezing the contents out into the main immiscible flow channel. An illustration of the technique can be seen in FIG. 31. This process would also allow large numbers to be released if arrays of actuators can be aligned with the chambers. For example, the use of an array of individually programmable mechanical points, such as that from a Braille display, can be used to achieve the method of sample volume ejection described here.

Figure 32:
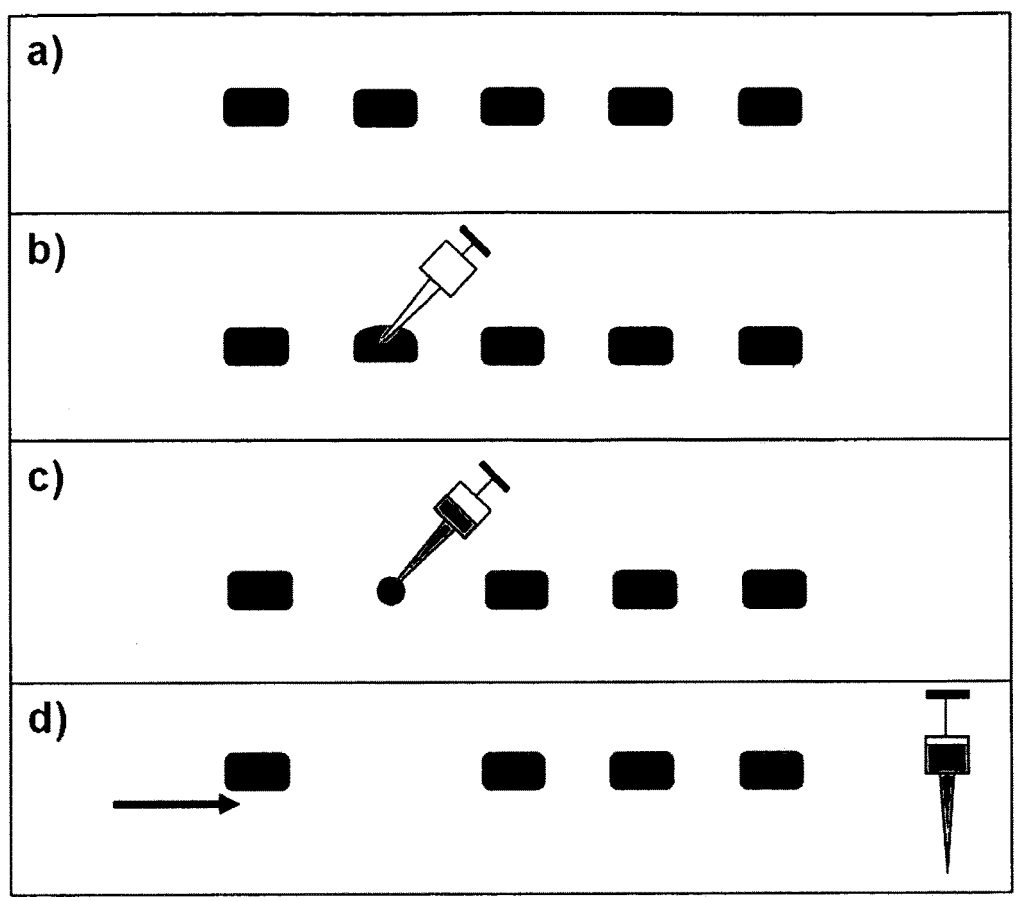
FIG. 32. Post discretization assay analysis and extraction. a) Samples are discretized into the compartment array. b) A small needle connected to a syringe is inserted through the substrate into the sample compartment (with machine vision ID marks, this can be positioned using automated actuators). c) The sample is extracted into the syringe then transported for further analysis (d).

Extraction of Sample Through Direct Syringe Removal by Piercing the Top of the Chamber Through choice of a substrate that can be readily penetrated by a small needle with a small tip diameter, microsyringe extraction of post discretized array of sample volumes can be done and transported to external instruments for further analysis. An illustration of a possible scheme can be seen in FIG. 32, where a needle is positioned and the compartment volume is extracted after an assay or analysis. Through the aid of modern machine vision and identification marks next to each compartment the needles can be positioned and samples extracted using programmable and automated actuators.

Figure 32A:
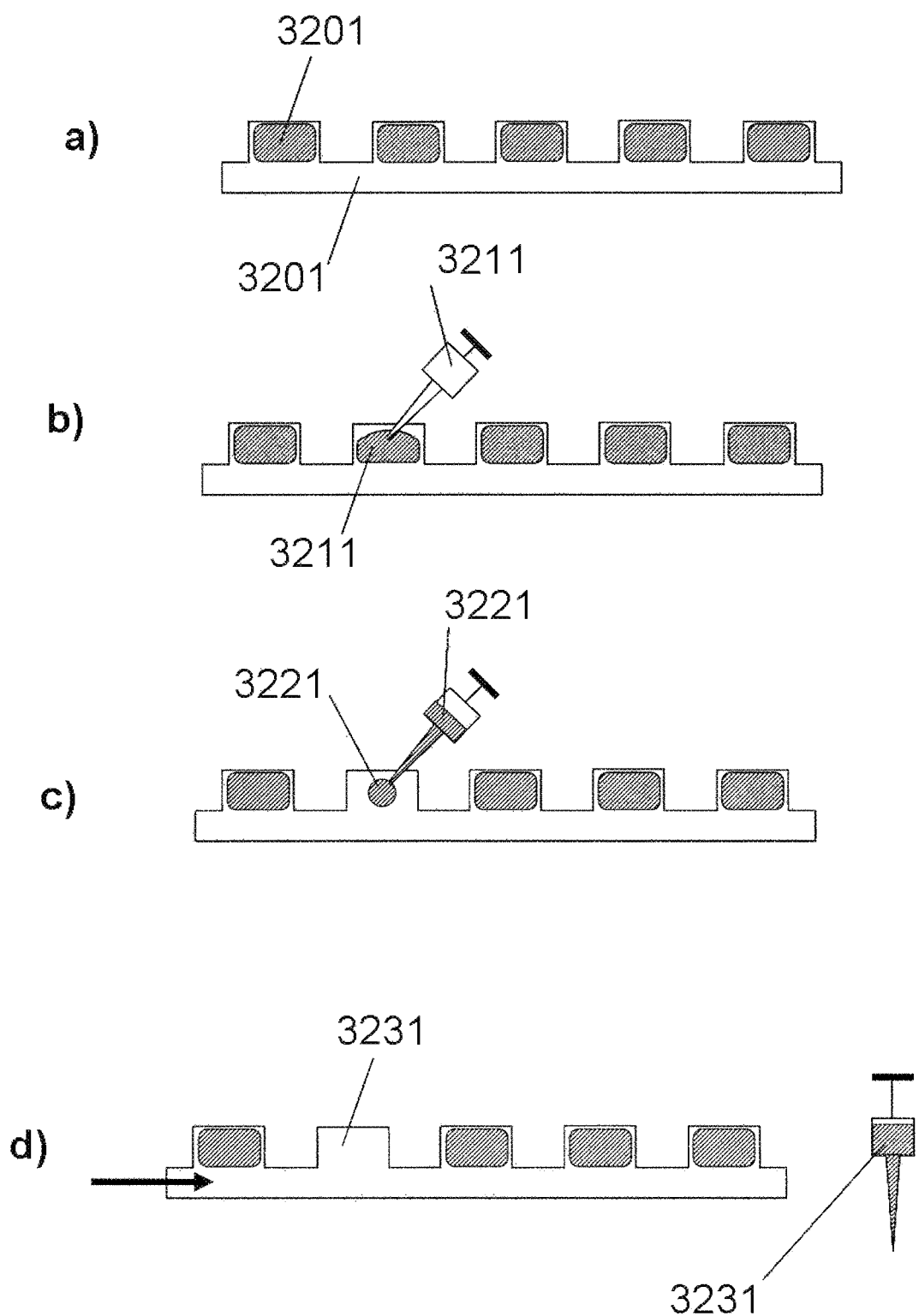
FIG. 32A. Individual release of packets from fluidic harbors by destruction of a wall.

In certain embodiments, fluidic packets are released from fluidic harbors by destruction of a wall. As illustrated in FIG. 32A, a fluidic lattice may be constructed out of a soft material such that fluidic packets may be released from a fluidic harbor by piercing the top or bottom of the harbor. In one embodiment, fluidic packets 3211 may be released from fluidic harbors by piercing with a small needle 3212. Through the aid of modern machine vision, alignment equipment, and identification marks next to each fluidic harbor, the needles could be positioned with a high degree of accuracy and fluidic packets could be extracted using programmable and automated actuators.

Extraction of the Sample Using Electrogenerated Droplets

Figure 34:
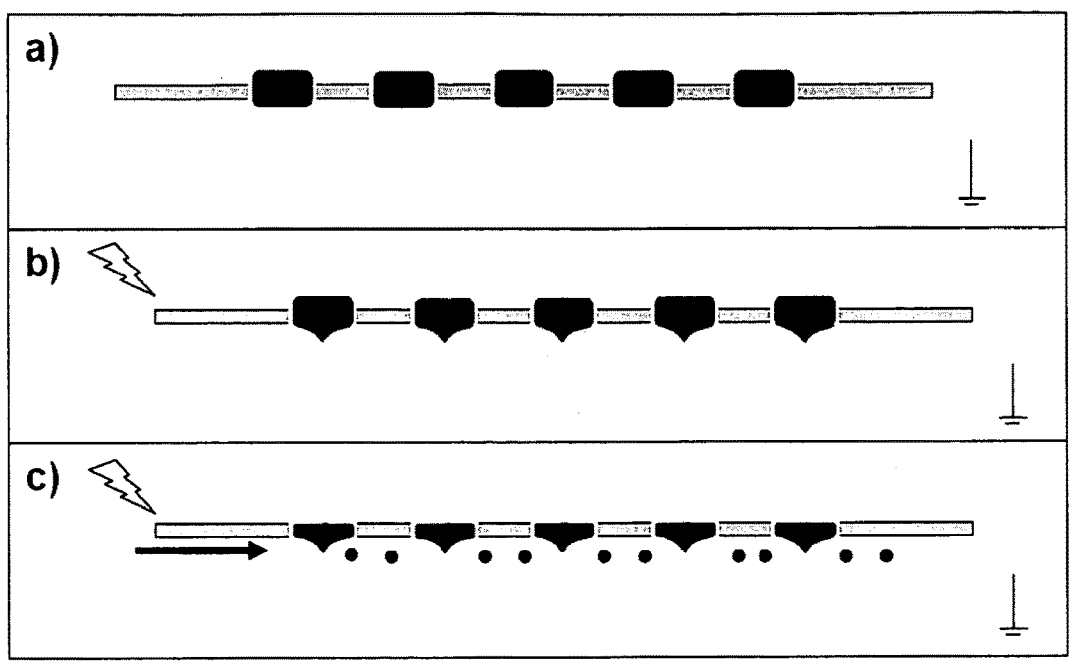
FIG. 34. Electrogeneration of droplets from within the array. a) samples are discretized into an array. b) application of a high voltage to the electrode in contact with the sample leads to formation of a Taylor cone. c) Pulsing of this high voltage supply allows for controlled droplet generation from the sample chambers.

Droplet generation has been demonstrated by applying an electrical pulse to an immiscible phase boundary. Using this methodology, electrogeneration of droplets from within the samples contained within the compartment is possible, portioning the sample volumes while still situated in the chambers. An example implementation is illustrated in FIG. 34, where the sample is compartmentalized into the array (FIG. 34(a)) and upon application of a high voltage to the electrode adjacent to the sample, a Taylor cone starts to form (FIG. 34(b)). Pulsing of this high voltage supply allows for controlled droplet generation from the sample wells, which can the flowed downstream for further analysis (FIG. 34(c)).

Figure 34A:
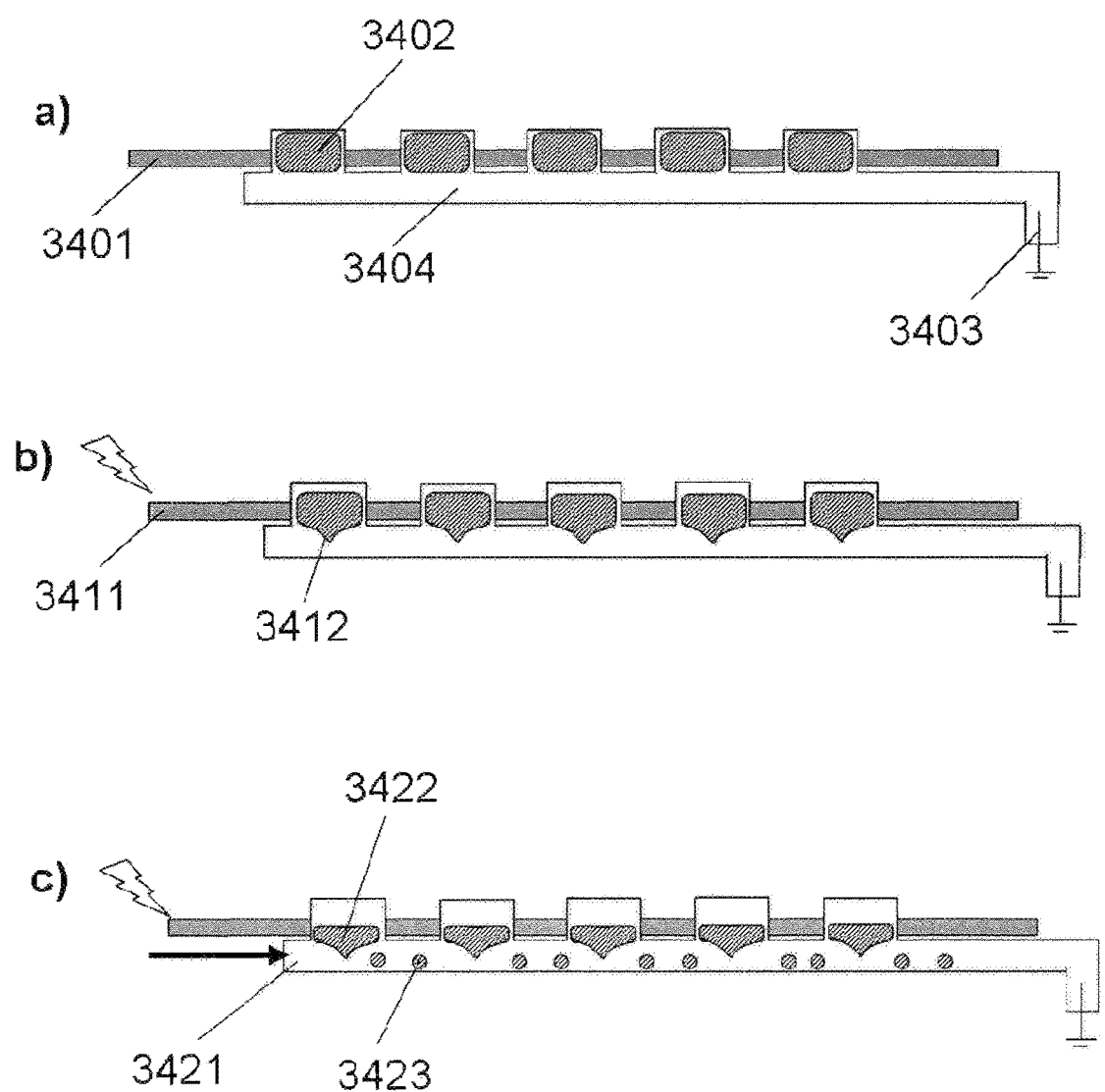
FIG. 34A. Schematic of releasing packets by electrogeneration of droplets.

In certain embodiments, fluidic packets are released from fluidic harbors by applying an electric field. As an example (FIG. 34A), fluidic packets may be released from fluidic harbors by disrupting the fluidic interface with a high voltage electrical pulse. A fluidic packet may be in contact with an electrode 3401 while the surrounding fluid may be in contact with another electrode 3403. As illustrated in FIG. 34A(a,b), upon applying a electrical potential difference across the two electrodes, a conical jet (Taylor cone) 3412 is formed at the fluidic packet/immiscible continuous fluid interface, and small droplets 3423 may be partitioned from the fluidic packet. Pulsing the electrical potential can offer a droplet controllably partitioned from fluidic packets, which can be flowed downstream for further analysis (FIG. 34A (c)).

Post Compartment Extraction and Further Manipulations

Example 14: Fluidic Packet Analysis after Releasing Fluidic Packets from Fluidic Harbors Once the sample has been removed from the array of sample compartments, and if flowing downstream the main channel, there are multiple handling methodologies downstream of the main channel. One method is transitioning the plug flowing through the channel into a droplet. Once the plug has been transferred to a larger flow region, its interface will relax thus forming a droplet and allowing for traditional droplet manipulations schemes to be implemented, including but not limited to, sorting (optical, hydrodynamic, electrokinetic), fusion (delivering or being delivered reactants), fission, mixing, docking, storage, freezing, heating, and interface fusion for integration into separation channels (e.g. capillary electrophoresis or capillary gel electrophoresis).

In certain embodiments, after fluidic packets are released from fluidic harbors, the released fluidic packets are subjected to further manipulation. As examples, a released fluidic packet may be subjected to sorting (using optical, hydrodynamic, or electrokinetic approaches), fusion with another fluidic packet to react chemically, fission into smaller packets, mixing, docking, freezing, heating, or fusing with another fluid for integration with other chemical separation techniques (e.g. capillary electrophoresis or capillary gel electrophoresis). FIG. 33A illustrates a sampling, of potential schemes in which fluidic packets, once released, may be manipulated: fluids may be injected from side channels 3325 and 3322 in FIG. 33A(c) and 3331 and 3334 in FIG. 33A(d) as a sheath flow (to control packet trajectory), as an accelerating flow (to control packet speed or spacing), or as a shearing flow to generate droplets 3342 from the fluidic packet (FIG. 33A(d)). Other schemes for manipulation of released fluidic packets are possible.

Further modifications can also be made to the stream as a whole, for example, for further thermal cycling in a semicontinuous fashion for applications involving PCR.

In certain embodiments, after fluidic packets are released from fluidic harbors said fluidic packets are subjected to a chemical reaction. As an example, a released fluidic packet containing genetic materials may be subjected to a series of thermal cycles in a polymerase chain reaction (PCR) to amplify the genetic materials.

Figure 33:
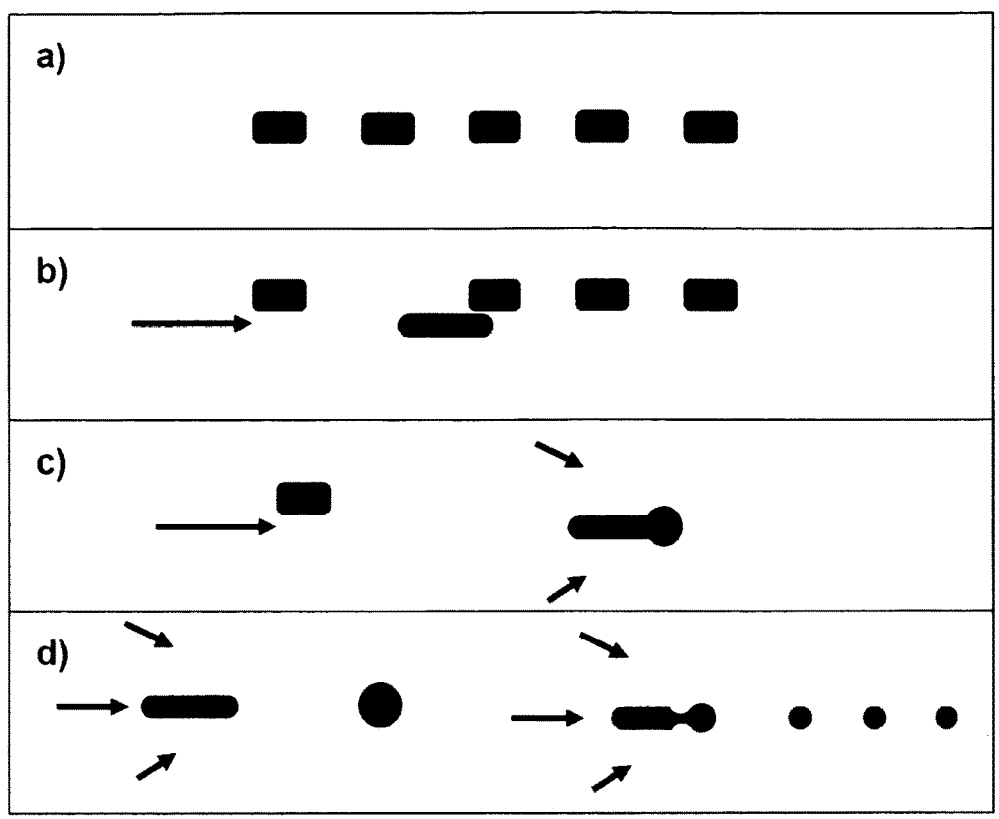
FIG. 33. Downstream sample transport scheme. a) Image of discretized samples. b) A representation of a sample plug in flow once removed from the compartment. c) The end of the discretization region connecting to a droplet flow zone with the addition of optional acceleration sheath flow (indicated flowing in above and below the main channel). d) Illustrates two possible processing into droplet techniques. Left, one plug from a single chamber forms one droplet. Right, the chamber volume is further partitioned using the sheath flow to break the plug into many droplets.
Figure 33A:
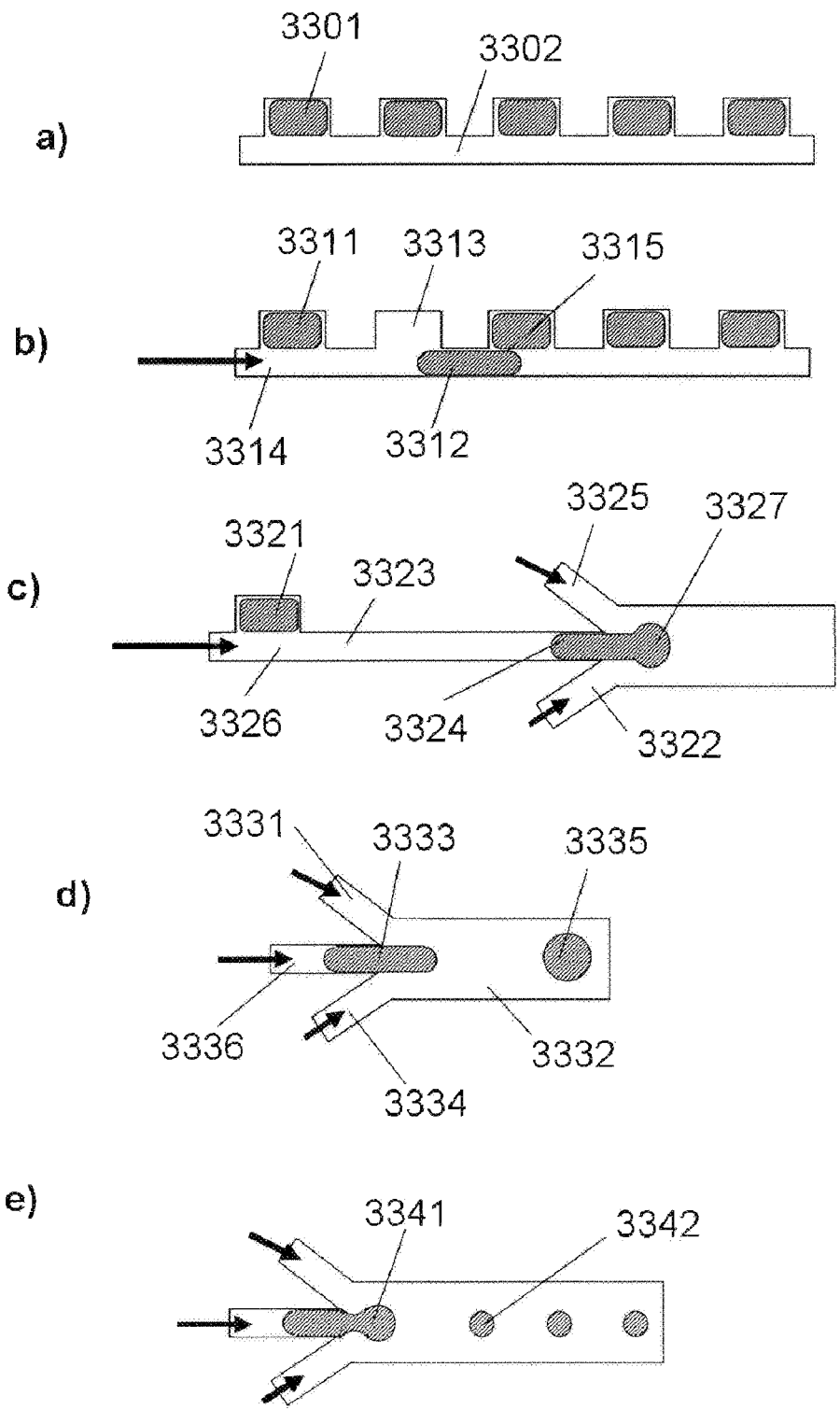
FIG. 33A. Schematics of subsequent manipulation after release of the fluidic packet.

The two common plug-to-droplet transfer schemes are illustrated in FIG. 33. Once the plug has transferred to the end of the continuous/immiscible phase flow channel, an optional acceleration or sheath flow (indicated flowing in above and below the main channel in FIG. 33(c) is introduced to separate the droplets as they enter the larger flow channel. An Illustration of two processing steps can be seen in FIG. 33(d), where the left pane shows one plug from a single chamber forming one droplet. The right pane shows the sample volume form a single chamber being partitioned using the sheath flow to break the plug into many droplets.

Besides the above manipulations, it is also possible to polymerize the aqueous-immiscible phase boundary such that the sample volumes are contained within a shell of interfacially polymerized polymers.

In certain embodiments, after fluidic packets are released from fluidic harbors said fluidic packets can be polymerized to form an encapsulated volume. As an example, the phase boundary between the two continuous fluids may be crosslinked into a contiguous membrane to form a solid boundary protecting the fluidic packet content. In another example, the entire fluidic packet may be crosslinked into a gel. In an embodiment, fluidic packets may be crosslinked into a gel without being released from fluidic harbors.

Applications

Example 15: Analysis of Fluidic Packets in Fluidic Harbors

Once the sample volumes have been discretized, embodiments of flexible methods and devices in accordance with the present invention are versatile for use in many areas, including but not limited to PCR, digital PCR, real time PCR, isothermal PCR, biological assays for diagnostics and prognostics, cancer diagnosis or cancer prognosis, disease diagnosis or disease prognosis, genetic screening, genotyping, determination of copy number variations, analysis of DNA methylation, high throughput screening, single molecule and single cell reactions or assays, single cell gene expression profiling, single organelle studies, single molecules and enzyme kinetics, single cell proteomic and "omic" studies, the study of crystallization and other statistical processes, protein crystallization, drug screening, environmental testing, synthesis of organic and inorganic molecules, synthesis of nanoparticles and capsules, and the coupling to a wide range of analytical detection techniques for biomedical assays and measurements. The minimal fluid interconnects and simple flow geometry makes the device easy to use and implement, and the material used to form the device may be optimized for the analysis or readout method of interest.

In certain embodiments, a fluidic harbor may be used to conduct biochemical analysis, including but not limited to: digital PCR, real-time PCR (RT-PCR), NASBA, single-cell imaging, single-cell identification or enumeration, biological assays for diagnostics and prognostics, high-throughput screening, single molecule or single cell reactions or assays, single molecules and enzyme kinetics, single cell proteomic or other "omic" studies, crystallization of proteins or other species, drug screening, environmental testing, statistical analysis, synthesis of organic and inorganic molecules, and synthesis of nanoparticles and nanocapsules.

Again, a particularly useful capability of the method and device is its ability to break up a sample into many distinctive aliquots prior to analysis. This method, once coupled to a separation or analysis technique, would allow for low volume samples to be aliquoted at or close to 100% efficiency, thereby reducing sample loss and having many aliquots of sample for parallel or repeated analysis or both.

In certain embodiments, a fluidic packet released from a fluidic harbor may be coupled to other analytical detection techniques for biomedical assays and measurements.

Polymerase Chain Reaction (PCR) and Genetic Analysis

Figure 35:
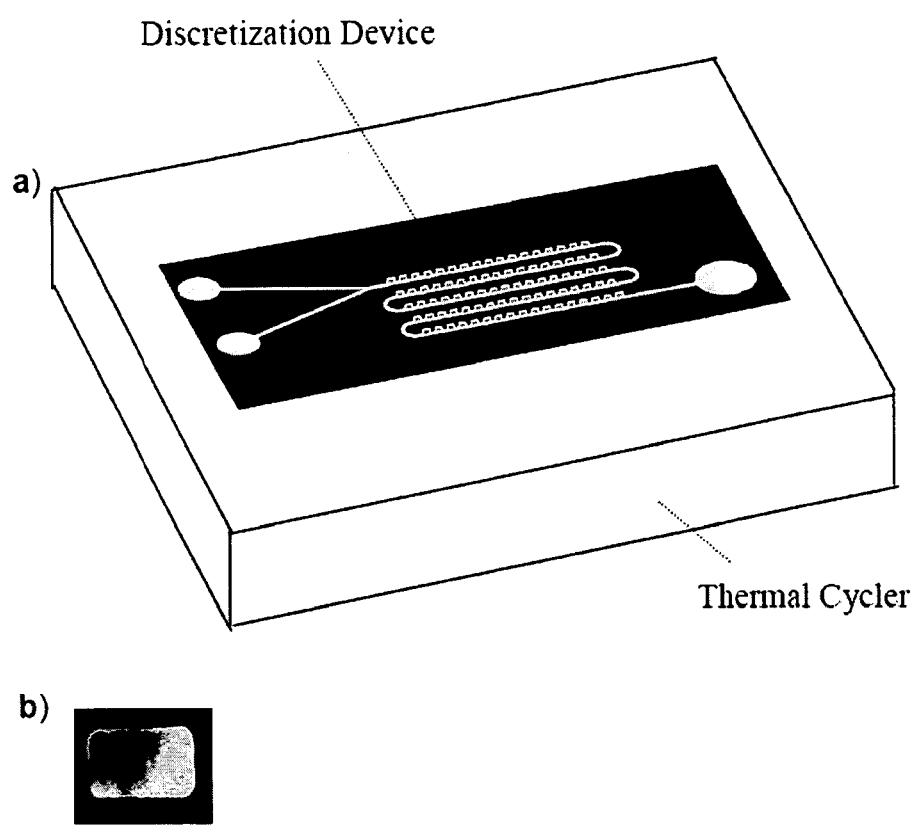
FIG. 35. a) Schematic for thermally cycling a discretization device. A device can be placed on or in a thermal cycler in order to perform polymerase chain reaction (PCR) on discretized samples. The discretized samples may also be imaged during thermal cycling in order to perform real time PCR or monitoring of signal increase. If the amount of template in the sample is diluted such that no sample compartment contains more than one template, the discretization device can be used to perform digital PCR. b) Image of the fluorescence from a discretized real time PCR sample that has undergone 40 cycles of thermal cycling. Besides the scheme depicted, many other methods of thermally cycling the discretization device for PCR is possible, such as the use of external lamps or integrated resistive heaters on chip, or simply use isothermal PCR schemes.

Example 16: Conducting Genetic Analysis within Fluidic Packets in Fluidic Harbors A device can easily be thermally cycled in order to perform PCR on discretized samples. The discretized samples may also be imaged during thermal cycling in order to perform real time PCR. If the amount of template in the sample is diluted such that no sample compartment contains more than one template, the discretization device can be used to perform digital PCR. The large array of discretized sample volumes can be formed using this technique and the device is ideally suited for digital PCR. FIG. 35 shows a schematic for using our invention to perform real time PCR. In FIG. 35(b) an image of the fluorescence from a discretized real time PCR sample that has undergone 40 cycles of thermal cycling is shown. Many other schemes can be implemented to couple our discretization device with digital PCR, including on-chip PCR using integrated resistive heaters or thermoelectric devices. Other off-chip schemes for thermal cycling are also possible, such as the use of heating lamps or other radiation sources to heat the sample volume for PCR applications.

In certain embodiments, a fluidic packet residing in a fluidic harbor may contain multiple copies of a genetic sequence (DNA or RNA). In an embodiment, a fluidic packet residing in a fluidic harbor may contain no more than one DNA molecule. In an embodiment, at least one fluidic packet residing in a fluidic harbor in a fluidic lattice may contain no DNA at all.

Figure 35A:
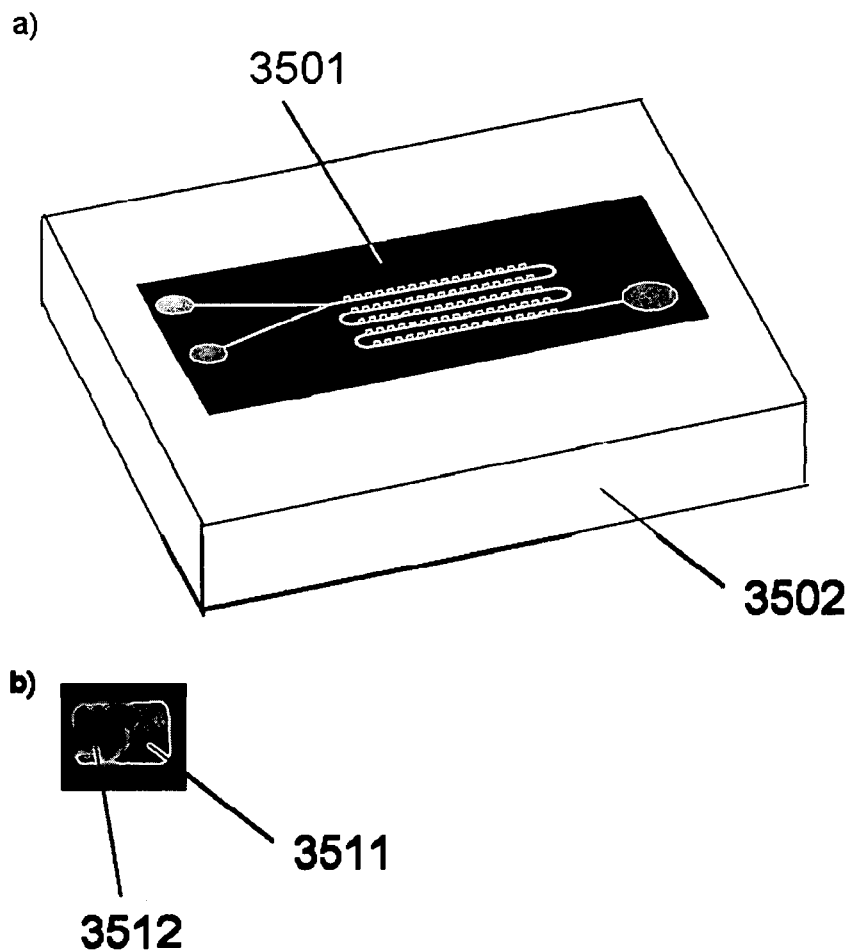
FIG. 35A. Schematics of using the invention to perform PCR.

As an example, a fluidic lattice containing fluidic packets residing in fluidic harbors may be thermally cycled to perform PCR. Each individual packet may be imaged during thermal cycling in order to perform real time PCR. If the amount of template in the specimen is diluted such that no packet contains more than one template, this fluidic lattice can be used to perform digital PCR (or digital real time PCR). A fluidic lattice can rapidly generate a large number of fluidic packets each containing no more than one copy of template and each uniquely identifiable according to the fluidic harbors they reside in. FIG. 35A shows a schematic of our invention to perform real time PCR (or any form of PCR). FIG. 35A(b) shows an image of the fluorescence from a fluidic packet containing real time PCR reagents that has undergone 40 cycles of thermal cycling.

In certain embodiments, a fluidic harbor with an integrated heater may be used to conduct digital PCR. An integrated heater may include resistive heaters, thermoelectric devices, metal pads, or diode-based radiation sources.

In certain embodiments, a fluidic harbor may be in contact with a heater to conduct digital PCR. A heater in contact may include heating lamps, conductive heaters, or radiation sources.

Figure 38:
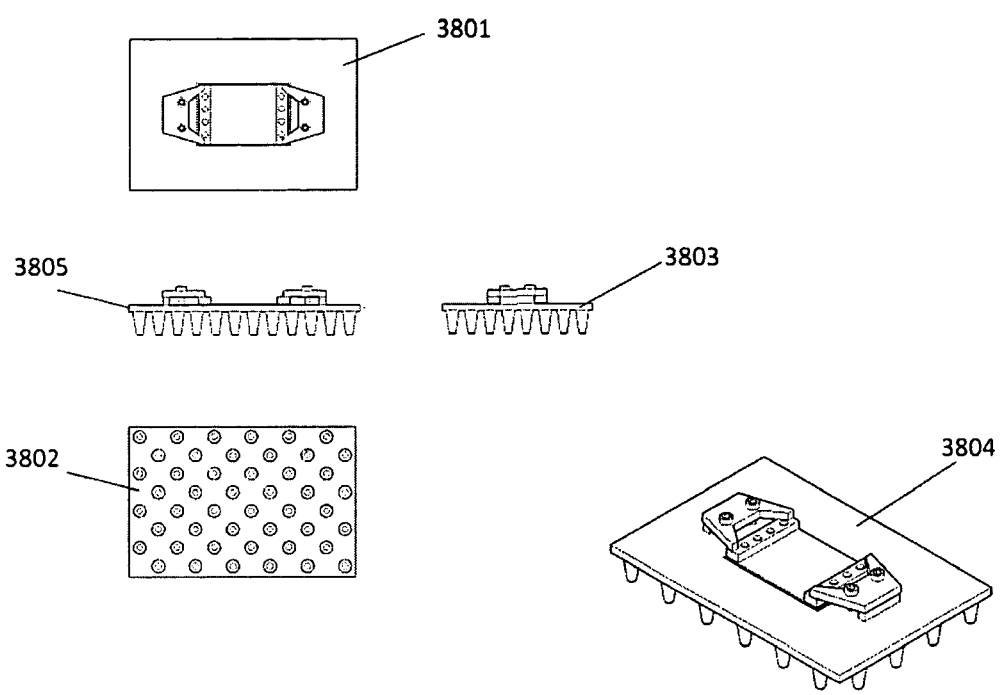
FIG. 38. Various views of a mechanical structure to interface a fluidic lattice with a DNA engine thermocycler.
Figure 39:
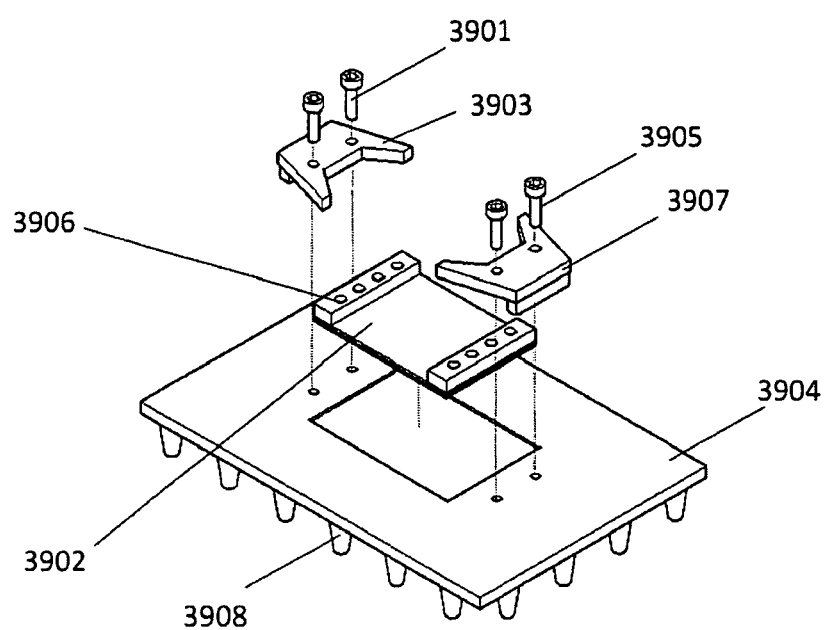
FIG. 39. Components of a mechanical structure to interface a fluidic lattice with a DNA engine thermocycler.

In certain embodiments, a fluidic lattice may be connected to a DNA engine thermocycler via a mechanical structure. FIG. 38 shows various views of such a mechanical structure intended to serve as a universal interface to connect a fluidic lattice to a commercial DNA engine thermocycler. In FIG. 38, this mechanical structure is shown in plane view (3801), reverse view (3802), end view (3803), angled view (3804), and side profile (3805). FIG. 39 illustrates various components of such a mechanical structure: the structure may consists of a thermally conductive copper top plate 3904 with copper fingers 3908 on one side, and chip holder clamps 3903 and 3907 on the other side holding a fluidic lattice 3902, and retaining bolts 3901 and 3905 to fasten the components. Fluids are delivered to the fluidic lattice by a tubing connected to fluidic ports 3906.

Figure 40:
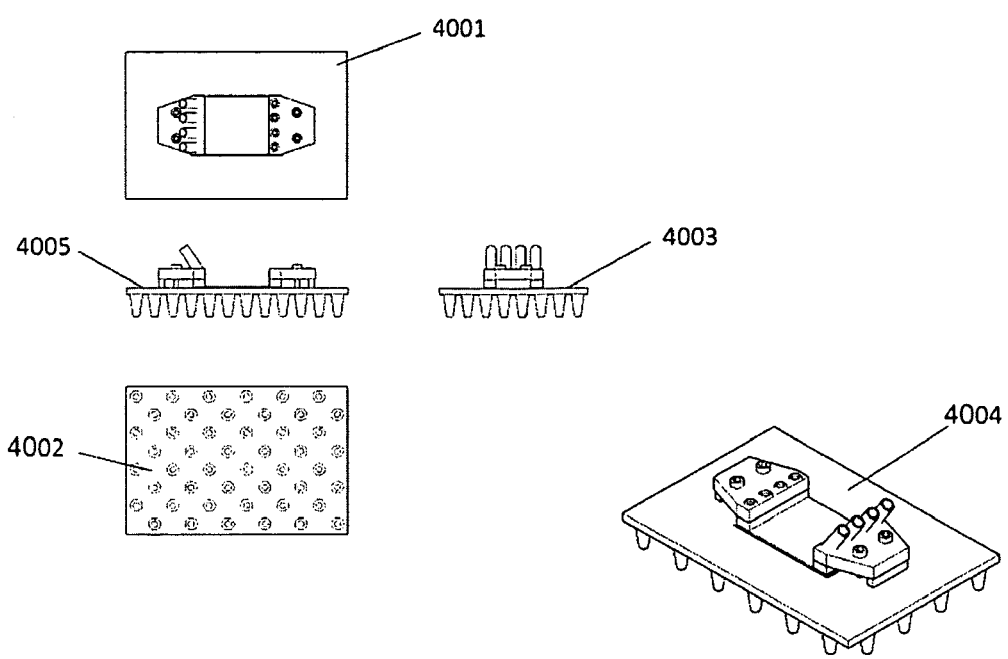
FIG. 40. Various views of a mechanical structure with valve connections to interface a fluidic lattice with a DNA engine thermocycler.
Figure 41:
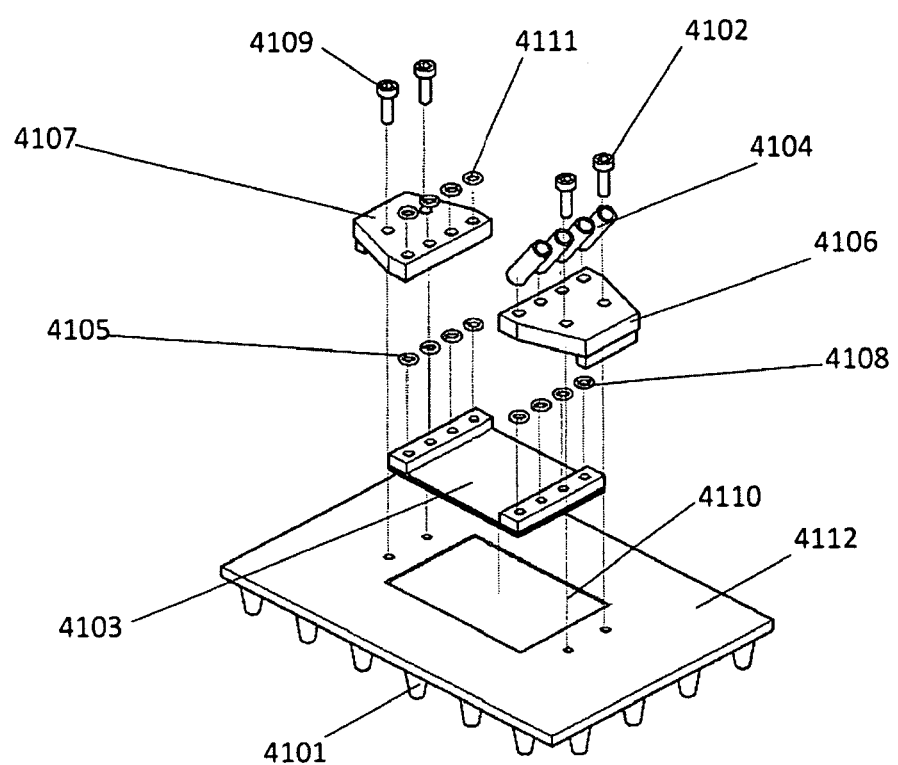
FIG. 41. Components of a mechanical structure with valve connections to interface a fluidic lattice with a DNA engine thermocycler.

FIG. 40 illustrates an alternate mechanical structure design incorporating valves and o-ring gaskets. In FIG. 40 the alternate mechanical structure is shown in plan view (4001), reverse view (4002), end view (4003), angled view (4004), and side view (4005). FIG. 41 illustrates various components of the alternate mechanical structure, which comprises a thermally conductive copper top plate 4112 with copper fingers 4101 on one side, and chip holder clamps 4106 and 4107 on the other side holding a fluidic lattice 4103 in a recessed receptacle 4110, and retaining bolts 4102 and 4109 to fasten the components. Valve connections 4104 and o-ring gaskets 4105, 4108, and 4111 are included to provide a robust fluidic seal and control.

Although digital PCR is ideally suited for use with the describe device and method, other types of PCR can be used, including but not limited to, standard PCR, real-time PCR, reverse-transcription PCR for analyzing RNAs and single cells, and various types of isothermal PCR.

In certain embodiments, a fluidic harbor may be used to conduct polymerase chain reaction (PCR). As an example, a fluidic lattice may be subjected to thermal cycling to amplify genetic materials in PCR reactions. Various modes of PCR are possible, including but not limited to digital PCR, discrete PCR, standard PCR, real-time PCR, reverse-transcription PCR for analyzing RNAs and single cells, and various types of isothermal PCR including but not limited to NASBA.

Under standard PCR operation, the chip containing the discretized sample is thermally cycled to amplify a DNA sequence of interest. Each sample volume containing a predefined number of target DNA is usually amplified through either a one (isothermal), two, or three temperature zone cycling.

Under standard PCR operation, a fluidic lattice containing fluidic packets is thermally cycled to amplify a genetic sequence of interest. Each fluidic packet containing a predefined number of target genetic sequence can be amplified by either a one (isothermal), two, or three temperature cycling protocol.

Under real time PCR operations, the chip is continually monitored using either large area fluorescence imaging or scanning a fluorescence confocal imaging through the array. This imaging is done at least once per cycle allowing for extrapolation of a threshold cycle and an exponential growth plot for each sample volume. By analyzing all of the discretized volumes independently, inhomogeneity in the sample can be recorded and quantified.

Under real time PCR operations, a fluidic lattice can be continually monitored using either large area fluorescence imaging or by confocal fluorescence scanning imaging through the fluidic lattice. This imaging is done at least once per cycle allowing for generation of an exponential growth fluorescence plot and for extrapolation of a threshold cycle for each fluidic packet. By analyzing all of the fluidic packets independently, inhomogeneity in the fluidic packets formed from a continuous fluid can be recorded and quantified.

Digital PCR implementation in the chip can be achieved using small chamber volumes and/or dilute samples. Having less than 1 copy of the target DNA in each compartment allows for variance in expression and sequence to be detected. Digital PCR can also be done in the chip by transferring whole cells and or subcellular components in the sample to the discretization compartments. A number of genetic analyses are possible with our device, such as genetic screening, genotyping, determination of copy number variations, analysis of DNA methylation, which are useful assays in disease diagnosis or prognosis, especially for cancer diagnosis or prognosis.

Digital PCR implementation in a fluidic lattice can be achieved using small fluidic harbors and/or dilute samples. Having less than 1 copy of the target DNA in each harbor allows for variance in expression and sequence to be detected. Digital PCR can also be done in a fluidic lattice by transferring materials that include but are not limited to biological fluids (e.g. blood, plasma, cerebral spinal fluids, lymph fluids, saliva, urine, etc.), whole cells, cell parts, and or subcellular components in the specimen to the fluidic harbors.

In PCR implementation, especially in digital PCR, it is becoming of interest to sequence the generated DNA directly after amplification. Our compartmentalization chip can contain a large array of samples where a fluorescent probe could be used to help identify target specific sample compartments of interest for sequencing. It also allows for an ordered removal of all compartments.

Due to our device simplicity and ease of design variance it is possible to incorporate various analytical techniques directly into the device. An example of which would be to include a gel electrophoresis separation channel downstream of the sample compartments. The samples could then be removed singly, in sequence, or in parallel and flowed to the separation channel as a droplet/plug. This can then be fused to the interface, in effect injecting the sample into the separation channel. Gel electrophoresis analysis thus can be used to sequence the amplified DNA in each sample volume/compartment. An example of a PCR device can be seen in FIG. 34, illustrating the simplicity of integration. FIG. 34(b) shows an image of an example PCR sample compartment after undergoing 40 thermal cycles.

In certain embodiments, a fluidic harbor may be used to conduct methylation analysis of DNA. The use of digital PCR is useful for a wide range of diagnostic, prognostic, and biomedical and biological assays. For example, the described device and method can be use to perform digital PCR of methylated DNA from patient blood samples, because epigenetic alterations of DNA, such as DNA hypermethylation and chromatin modification, have been demonstrated and established in human cancer. In this application, our device and method can be used to perform PCR amplification of bisulfite-converted DNA for DNA methylation analysis or use the traditional and commercially available MethylLight assays in a digital format, since our device and method efficiently discretizes the sample volume into a large array. Although these assays are best performed in a digital format, our device and method can be applied equally well in a non-digital format, and here, the partitioning of the original sample volume into many parallel discretized sample volumes is still highly advantageous.

Example 17: Crystallization within Fluidic Packets in Fluidic Harbors

In certain embodiments, fluidic packets residing in fluidic harbors may be used for crystallization. In some embodiment, fluidic packets residing in fluidic harbors may be used to conduct crystallization of proteins. In certain embodiments, fluidic packets residing in fluidic harbors may be used to conduct crystallization of small molecules.

Crystallization experiments that can be conducted in fluidic packets residing in fluidic harbors include, but are not limited to, polymorph screening, solvate screening, salt screening, co-crystallization, crystal dyeing, protein crystallization, chiral resolution, homogeneous crystallization, heterogeneous crystallization, and crystallization with 'tailor-made' additives.

Figure 36:
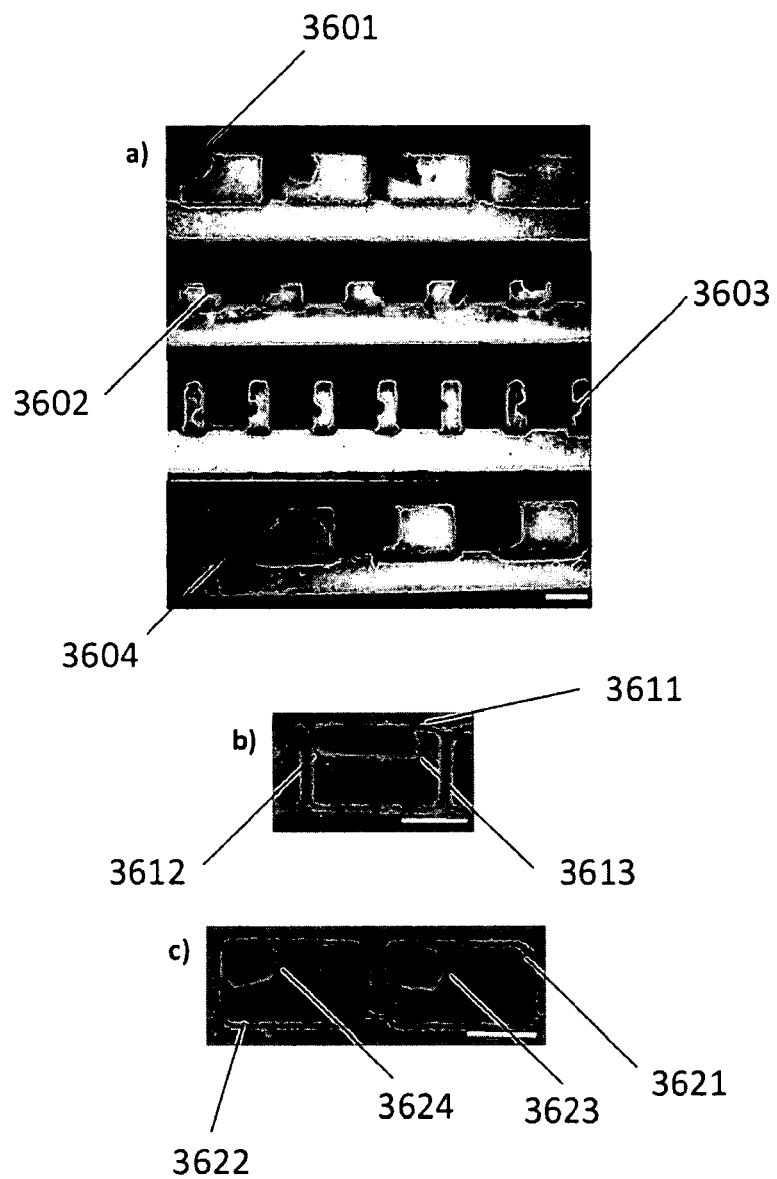
FIG. 36. Crystallization in fluidic packets.

In certain embodiments, fluidic packets residing in fluidic harbors in a permeable fluidic lattice may be used for crystallization. Fluidic packets formed from a continuous fluid that is saturated with an analyte of interest may be used to grow polymorphs of a small organic molecule in a fluidic harbor of a permeable fluidic lattice. A permeable fluidic lattice may be constructed from, for example, a gas- or solvent-permeable material, including but not limited to polydimethylsiloxane (PDMS), such that select components of a fluidic packet may evaporate through or become absorbed by (or dissolved into) the lattice material. These select components may include, but are not limited to, a solvent. The process of evaporation or absorption of solvents by fluidic lattice can enhance the crystallization process, allowing exquisite control of the crystal types grown. FIG. 36 displays images of crystals in fluidic harbors in a fluidic lattice, constructed out of glass and PDMS, that were formed when fluidic packets composed of $1\times10^{-2}$ M 2,5-dihydroxybenzoic acid (2,5-DHB) and $1\times10^{-5}$ M methyl red in 50% aqueous ethanol were held at room temperature for 2-3 days. The other continuous fluid was light mineral oil with 0.05% Span 80. All scale bars (FIGS. 36((a), (b), and (c)) refer to 100 μm.

In certain embodiments, fluidic harbors of various sizes may be used for crystallization. In another embodiment, fluidic harbors of various sizes may be simultaneously used to conduct parallel screening of multiple crystallization conditions in drug development. Sizes can refer to a dimension, a surface area, or a volume. FIG. 36 shows five sizes of fluidic harbors used to grow different crystals. Since the evaporation/absorption rate of permeable components vary as a function of the size of fluidic harbor, the analyte concentration can be varied and this can lead to preferential crystallization of some other mixture component(s), including the analyte(s) of interest. Modification of crystallization conditions can give rise to polymorphism, the ability of a solid material to exist in more than one form or crystal structure. The identification of polymorphs and other crystalline forms is extremely important in the pharmaceutical industry because each crystalline form must be patented individually (including crystals in which more than one species exist in the repeating unit cell, such as solvates or co-crystals). It is therefore necessary to identify as many crystalline forms as possible in the drug development stage. Here, the partitioning of a single continuous fluid into many parallel fluidic packets, each exposed to different crystallization conditions, would be a highly advantageous crystallization screening method. In addition, the small volume of a fluidic harbor is an appealing feature when only small amounts of a potential new drug have been synthesized.

FIG. 36 displays images of crystalline polymorphs residing in fluidic harbors in a fluidic lattice. In FIG. 36 (panel b), the crystal interfacial angles specified by 3612 and 3613 appear consistent with those that have been previously observed in Form I of 2,5-dihydroxybenzoic acid (2,5-DHB). In FIG. 36 (panel c), the interfacial angles specified by 3623 and 3624 appear consistent with those that have previously been observed in Form II of 2,5-DHB (a different polymorph than Form I 2,5-DHB). In addition, the colors of methyl red observed in FIG. 36 (panels (b) and (c)) appear consistent with those that have been previously observed for Forms I and II of 2,5-DHB, respectively. The volume of the fluidic harbor was larger in FIG. 36 (panel b) than in FIG. 36 (panel c).

In another embodiment, a fluidic lattice can be either cooled or heated at variable rates to induce crystallization. In another embodiment, a fluidic harbor may have a different heating or cooling rate from another fluidic harbor. By varying the heating and/or cooling rate, many crystallization conditions can be screened simultaneously within the same fluidic lattice. The heating or cooling rate of each individual fluidic harbor can be predefined and easily configured. Heating and cooling devices may include, but are not limited to, resistive heaters, thermoelectric devices, metal pads, heating lamps, conductive heaters, or radiation sources. It is possible that the heating and/or cooling device(s) may be computer controlled and easily adjustable.

Crystals that have grown in fluidic harbors may be analyzed by methods that include, but are not limited to light microscopy, electron microscopy, microscopy with polarized light, polarized absorption spectroscopy, absorption spectroscopy, raman microspectroscopy, infrared microspectroscopy, x-ray diffraction, thermal analysis, solid state NMR, particle size analysis, and melting point determination.

Example 18: Conducting Cellular Analysis within Fluidic Packets in Fluidic Harbors In certain embodiments, a fluidic packet in a fluidic harbor may contain a bioparticle or an analyte. In some embodiments, a fluidic packet in a fluidic harbor may contain a biological cell.

According to certain embodiments, a fluidic packet in a fluidic harbor may contain a rare cell. A rare cell may be nucleated or non-nucleated. Rare cells include, but are not limited to, the following cells: cells expressing a malignant phenotype; fetal cells, such as fetal cells in maternal peripheral blood; circulating endothelial cells; tumor cells, such as tumor cells which have been shed from tumor into blood or other bodily fluids or bone marrow; cells infected with a virus, such as cells infected by HIV, cells transfected with a gene of interest; and aberrant subtypes of T-cells or B-cells present in the peripheral blood of subjects afflicted with autoimmune or autoreactive disorders.

A cell may be considered as rare if its concentration is (1) less than 10% of the total cell population in a fluid sample; (2) less than 1% of the total cell population in a fluid sample; or (3) less than 1 million cells per milliliter of fluid sample.

Figure 37:
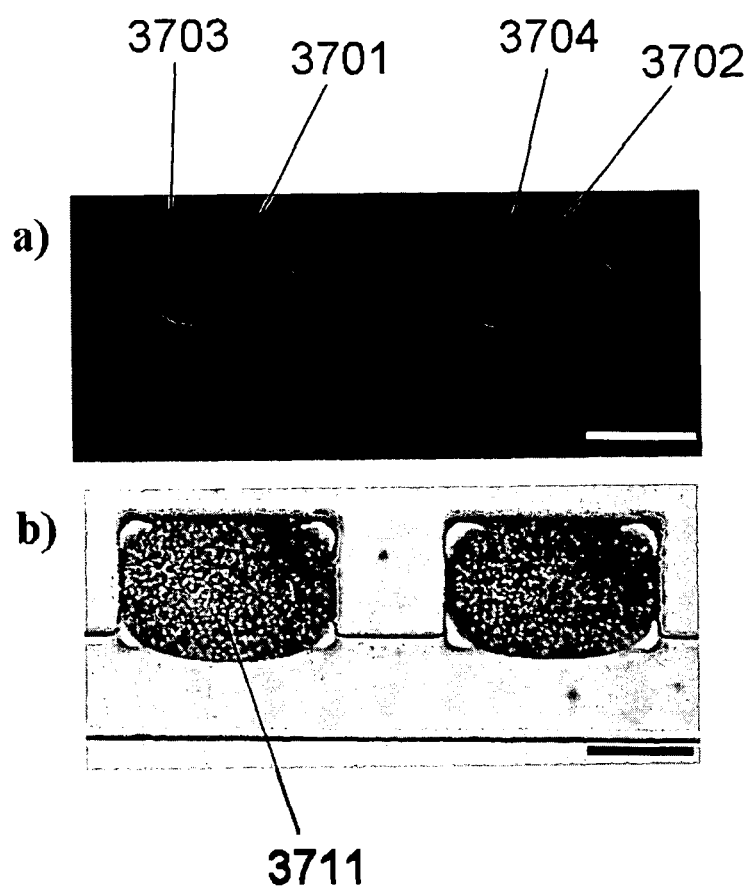
FIG. 37. Cell enumeration and blood analysis using fluidic packets.

In an embodiment, a fluidic harbor may be used to conduct analysis of biological particles. In another embodiment a fluidic harbor may be used conduct analysis of rare cells. For example, FIG. 37(a) is an image of a cell 3701 (and 3702) in rare concentration formed into fluidic packet 3703 (and 3704) residing in fluidic harbors. Fluidic packets inside orderly fluidic harbors allow easy visual identification, enumeration, and biochemical analysis of these partitioned rare cells. The analyte-containing fluid in this case consists of 95% growth media and 5% B-cell in volume.

FIG. 37(b) is an image of undiluted human blood consisting of white blood cells, red blood cells, platelets, and plasma formed into fluidic packet 3711 residing in a fluidic harbor. Thus fluidic packets inside orderly fluidic harbors can be further analyzed for biochemical content which can be correlated to human disease status or offer diagnostic or prognostic information.

Embodiments in accordance with the present invention may be used in a wide variety of applications in biology and diagnosis of disease, including capturing cancer cells or cancer stem cells from body fluids for cancer prognosis; circulating endothelial cells; subsets of immune cells; parasites such as *giardia* or *cryptosporidium* for water quality monitoring; malaria-infected erythrocytes for malaria diagnosis; lymphocytes and leucocytes for HIV monitoring; fetal cells in maternal blood for disease screening; stem cells for therapy; prion-infected cells for prion-related (e.g. mad cow) disease screening.

In one example, the present subject matter includes fluidic lattices fabricated from materials including, but not limited to, polymeric materials (polydimethylsiloxane (PDMS), polymethylmethacrylate (PMMA), polyethylene, polyester (PET), thermoset polyester (TPE), polytetrafluoroethylene (PTFE), polycarbonate, parylene, polyvinyl chloride, fluoroethylpropylene, lexan, polystyrene, cyclic olefin copolymers, polyurethane, polyurethane blended with polyacrylate, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide, polyimide), inorganic materials (glass, quartz, silicon, GaAs, silicon nitride), fused silica, ceramic, glass (organic), metals and/or other materials and combinations thereof.

In addition, the wall materials can be fabricated of porous membranes, woven or non-woven fibers (such as cloth or mesh) of wool, metal (e.g. stainless steel or Monel), glass, paper, or synthetic (e.g. nylon, polypropylene, polycarbonate, parylene, and various polyesters), sintered stainless steel and other metals, and porous inorganic materials such as alumina, silica or carbon.

The continuous fluid flow can be delivered by, for example, methods and devices that induce hydrodynamic fluidic pressure, which include but are not limited to those that operate on the basis of mechanical principles (e.g. external syringe pumps, pneumatic membrane pumps, vibrating membrane pumps, vacuum devices, centrifugal forces, and capillary action); electrical or magnetic principles (e.g. electroosmotic flow, electrokinetic pumps piezoelectric/ultrasonic pumps, ferrofluidic plugs, electrohydrodynamic pumps, and magnetohydrodynamic pumps); thermodynamic principles (e.g. gas bubble generation/phase-change-induced volume expansion) surface-wetting principles (e.g. electrowetting, chemically, thermally, and radioactively induced surface-tension gradient).

Additional methods for the generation of continuous fluid driving force can be provided by hydrodynamic pressure, gravity feed, surface tension (like capillary action), electrostatic forces (electrokinetic flow), centrifugal flow (substrate disposed on a compact disc and rotated), magnetic forces (oscillating ions causes flow), magnetohydrodynamic forces, and a vacuum or pressure differential, as well as other continuous fluid driving force generation methods.

What is claimed is:

1. An apparatus comprising:
   a flow channel having a flow axis, the flow channel being in selective fluid communication with a source of a continuous fluid comprising an aqueous solution;
   a first fluidic harbor offset from the flow axis and fluidically coupled to the flow channel at a first location of the flow channel and at a second location of the flow channel;
   a second fluidic harbor offset from the flow axis and fluidicially coupled to the flow channel at a first plurality of locations upstream of the first location along the flow channel;
   a third fluidic harbor offset from the flow axis and fluidically coupled to the flow channel at a second plurality of locations downstream of the second location along the flow channel; and
   a primer solution immiscible with the aqueous solution, the primer solution disposed within at least two of the fluidic harbors;
   wherein the first location is upstream of the second location along the flow channel.

2. The apparatus of claim 1 wherein the flow channel is in selective fluid communication with a source of a primer fluid.

3. The apparatus of claim 2 wherein the primer fluid contains a surfactant.

4. The apparatus of claim 2 wherein a surface of at least one of the fluidic harbors is modified to affect its interaction with the continuous fluid and/or the primer fluid.

5. The apparatus of claim 1 wherein the continuous fluid is an aqueous solution comprising an analyte.

6. The apparatus of claim 5 wherein the analyte is a nucleic acid.

7. The apparatus of claim 5 wherein the analyte is a biological cell.

8. The apparatus of claim 1 wherein the flow channel contains a primer fluid and the primer fluid contains a surfactant.

9. The apparatus of claim 1 wherein a shape of at least one of the plurality of fluidic harbors is other than spherical.

10. The apparatus of claim 1 wherein the plurality of fluidic harbors are arranged in series along the flow channel.

11. The apparatus of claim 1 further comprising a second channel in fluid communication with at least two fluidic harbors of the plurality of fluidic harbors.

12. The apparatus of claim 1 further comprising a second channel whose dimension is smaller than the flow channel.

13. The apparatus of claim 1 wherein a surface of at least one of the fluidic harbors is hydrophobic.

14. The apparatus of claim 1 wherein at least one of the fluidic harbors is oleophilic.

15. The apparatus of claim 1 wherein at least one of the fluidic harbors is located out of a plane defined by the flow channel.

16. The apparatus of claim 1 wherein the fluidic harbor comprises a nucleic acid.

17. An apparatus comprising:
   a flow channel having a flow axis, the flow channel being in selective fluid communication with a source of a first continuous liquid and in selective fluid communication with a source of a second continuous liquid immiscible with the first liquid;
   a first fluidic harbor offset from the flow axis and fluidically coupled to the flow channel at a first location of the flow channel and at a second location of the flow channel, wherein the first location is upstream of the second location along the flow channel;
   a second fluidic harbor offset from the flow axis and fluidically coupled to the flow channel at a first plurality of locations upstream of the first location along the flow channel;

a third fluidic harbor offset from the flow axis and fluidically coupled to the flow channel at a second plurality of locations downstream of the second location along the flow channel; and a primer fluid contained within at least one of the plurality of fluidic harbors, wherein the primer fluid is immiscible with the first continuous liquid.

18. The apparatus of claim 17 wherein the flow channel is in selective fluid communication with a source of a primer fluid.

19. The apparatus of claim 18 wherein the primer fluid contains a surfactant.

20. The apparatus of claim 17 wherein the flow channel contains a primer fluid.

21. The apparatus of claim 20 wherein the primer fluid contains a surfactant.

22. The apparatus of claim 17 wherein the first continuous liquid is an aqueous solution.

23. The apparatus of claim 22 wherein the aqueous solution contains an analyte.

24. The apparatus of claim 23 wherein the analyte is a nucleic acid.

25. The apparatus of claim 23 wherein the analyte is a biological cell.

26. The apparatus of claim 17 wherein the second continuous liquid contains a surfactant.

27. The apparatus of claim 17 wherein a shape of at least one of the plurality of fluidic harbors is other than spherical.

28. The apparatus of claim 27 wherein a cross-section of at least one of the fluidic harbors is T-shaped, L-shaped, triangular, rectangular, or square.

29. The apparatus of claim 17 wherein a surface of at least one of the fluidic harbors is modified to affect its interaction with the first liquid and/or the second liquid.

30. The apparatus of claim 17 wherein the plurality of fluidic harbors are arranged in series along the flow channel.

31. The apparatus of claim 17 further comprising a second channel in fluid communication with at least two fluidic harbors of the plurality of fluidic harbors.

32. The apparatus of claim 17 wherein a surface of at least one of the fluidic harbors is hydrophobic.

33. The apparatus of claim 17 wherein at least one of the fluidic harbors is oleophilic.

34. The apparatus of claim 17 wherein at least one of the fluidic harbors is located out of a plane defined by the flow channel.

35. The apparatus of claim 34 wherein at least one fluidic harbor has a height taller than the height of the flow channel.

36. The apparatus of claim 17 wherein the fluidic harbor comprises a nucleic acid.

37. The apparatus of claim 17 wherein the primer fluid and the second continuous liquid comprise the same fluid.

* * * * *